United States Patent
Hartman et al.

(10) Patent No.: US 9,527,845 B2
(45) Date of Patent: Dec. 27, 2016

(54) DERIVATIVES AND METHODS OF TREATING HEPATITIS B INFECTIONS

(71) Applicant: Novira Therapeutics, Inc., Doylestown, PA (US)

(72) Inventors: George D. Hartman, Lansdale, PA (US); Scott Kuduk, Harleysville, PA (US)

(73) Assignee: NOVIRA THERAPEUTICS, INC., Doylestown, PA (US)

(*) Notice: Subject to any disclaimer, the term of this patent is extended or adjusted under 35 U.S.C. 154(b) by 0 days.

(21) Appl. No.: 14/984,293

(22) Filed: Dec. 30, 2015

(65) Prior Publication Data

US 2016/0185777 A1 Jun. 30, 2016

Related U.S. Application Data

(60) Provisional application No. 62/097,835, filed on Dec. 30, 2014, provisional application No. 62/163,150, filed on May 18, 2015.

(51) Int. Cl.

| | | |
|---|---|---|
| *C07D 513/02* | (2006.01) | |
| *C07D 471/04* | (2006.01) | |
| *A61K 38/21* | (2006.01) | |
| *A61K 39/29* | (2006.01) | |
| *C12N 7/00* | (2006.01) | |
| *A61K 31/437* | (2006.01) | |
| *A61K 31/5377* | (2006.01) | |
| *A61K 45/06* | (2006.01) | |
| *A61K 31/501* | (2006.01) | |

(52) U.S. Cl.
CPC ........... *C07D 471/04* (2013.01); *A61K 31/437* (2013.01); *A61K 31/501* (2013.01); *A61K 31/5377* (2013.01); *A61K 38/212* (2013.01); *A61K 39/292* (2013.01); *A61K 45/06* (2013.01); *C12N 7/00* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| 8,273,765 B2 | 9/2012 | Fancelli et al. |
|---|---|---|
| 8,288,425 B2 | 10/2012 | Edwards et al. |
| 2014/0330009 A1 | 11/2014 | Bialy et al. |
| 2016/0046648 A1* | 2/2016 | Petrukhin ............ C07D 471/04 514/215 |
| 2016/0185778 A1 | 6/2016 | Hartman et al. |
| 2016/0185779 A1 | 6/2016 | Hartman et al. |

FOREIGN PATENT DOCUMENTS

| WO | 2004/014374 A1 | 2/2004 |
|---|---|---|
| WO | 2010/060854 A1 | 6/2010 |
| WO | 2012/036997 A1 | 3/2012 |
| WO | 2014/152013 A1 | 9/2014 |
| WO | 2016/109663 A2 | 7/2016 |
| WO | 2016/109684 A2 | 7/2016 |
| WO | 2016/109689 A2 | 7/2016 |
| WO | 2016/113273 A1 | 7/2016 |

OTHER PUBLICATIONS

SciFinder Database. CAS Registration No. 1516653-16-9. Chemical Abstract Services. American Chemical Society. [Last Accessed Jul. 25, 2016].
SciFinder Database. CAS Registration No. 1522224-86-7. Chemical Abstract Services. American Chemical Society. [Last Accessed Jul. 25, 2016].
SciFinder Database. CAS Registration No. 1567296-86-9. Chemical Abstract Services. American Chemical Society. [Last Accessed Jul. 25, 2016].
SciFinder Database. CAS Registration No. 1567311-64-1. Chemical Abstract Services. American Chemical Society. [Last Accessed Jul. 25, 2016].
SciFinder Database. CAS Registration No. 1567490-89-4. Chemical Abstract Services. American Chemical Society. [Last Accessed Jul. 25, 2016].
SciFinder Database. CAS Registration No. 1574576-07-0. Chemical Abstract Services. American Chemical Society. [Last Accessed Jul. 25, 2016].
SciFinder Database. CAS Registration No. 1574592-26-9. Chemical Abstract Services. American Chemical Society. [Last Accessed Jul. 25, 2016].
SciFinder Database. CAS Registration No. 1574626-86-0. Chemical Abstract Services. American Chemical Society. [Last Accessed Jul. 25, 2016].
SciFinder Database. CAS Registration No. 1574640-97-3. Chemical Abstract Services. American Chemical Society. [Last Accessed Jul. 25, 2016].
SciFinder Database. CAS Registration No. 1609742-77-9. Chemical Abstract Services. American Chemical Society. [Last Accessed Jul. 25, 2016].
International Search Report with Written Opinion corresponding to International Patent Application No. PCT/US2015/068059, mailed Jun. 29, 2016.
International Search Report with Written Opinion corresponding to International Patent Application No. PCT/US2015/068091, mailed Jun. 29, 2016.
International Search Report with Written Opinion corresponding to International Patent Application No. PCT/US2015/068099, mailed Jun. 29, 2016.
Samala et al. (Sep. 12, 2013) "Development of 3-phenyl-4,5,6,7-tetrahydro-1H-pyrazolo[4,3-c]pyridine derivatives as novel *Mycobacterium tuberculosis* pantothenate synthetase inhibitors," Eur. J. Med. Chem. 9:356-364.
SciFinder Database. CAS Registration No. 895821-52-0. Chemical Abstract Services. American Chemical Society. [Last Accessed Jul. 25, 2016].

(Continued)

*Primary Examiner* — Heidi Reese
(74) *Attorney, Agent, or Firm* — Brian C. Trinque; Lathrop & Gage LLP

(57) ABSTRACT

Provided herein are compounds useful for the treatment of HBV infection in a subject in need thereof, pharmaceutical compositions thereof, and methods of inhibiting, suppressing, or preventing HBV infection in the subject.

19 Claims, No Drawings

(56) References Cited

OTHER PUBLICATIONS

SciFinder Database. CAS Registration No. 895828-24-7. Chemical Abstract Services. American Chemical Society. [Last Accessed Jul. 25, 2016].
SciFinder Database. CAS Registration No. 895835-76-4. Chemical Abstract Services. American Chemical Society. [Last Accessed Jul. 25, 2016].
SciFinder Database. CAS Registration No. 895842-18-9. Chemical Abstract Services. American Chemical Society. [Last Accessed Jul. 25, 2016].
SciFinder Database. CAS Registration No. 899378-47-3. Chemical Abstract Services. American Chemical Society. [Last Accessed Jul. 25, 2016].
SciFinder Database. CAS Registration No. 903199-10-0. Chemical Abstract Services. American Chemical Society. [Last Accessed Jul. 25, 2016].
SciFinder Database. CAS Registration No. 903585-33-1. Chemical Abstract Services. American Chemical Society. [Last Accessed Jul. 25, 2016].
SciFinder Database. CAS Registration No. 903853-89-4. Chemical Abstract Services. American Chemical Society. [Last Accessed Jul. 25, 2016].
SciFinder Database. CAS Registration No. 903867-06-1. Chemical Abstract Services. American Chemical Society. [Last Accessed Jul. 25, 2016].
SciFinder Database. CAS Registration No. 903867-67-4. Chemical Abstract Services. American Chemical Society. [Last Accessed Jul. 25, 2016].
SciFinder Database. CAS Registration No. 906757-81-1. Chemical Abstract Services. American Chemical Society. [Last Accessed Jul. 25, 2016].
SciFinder Database. CAS Registration No. 906762-37-6. Chemical Abstract Services. American Chemical Society. [Last Accessed Jul. 25, 2016].
SciFinder Database. CAS Registration No. 1061115-87-4. Chemical Abstract Services. American Chemical Society. [Last Accessed Jul. 25, 2016].
SciFinder Database. CAS Registration No. 1067040-18-9. Chemical Abstract Services. American Chemical Society. [Last Accessed Jul. 25, 2016].
SciFinder Database. CAS Registration No. 1069950-13-5. Chemical Abstract Services. American Chemical Society. [Last Accessed Jul. 25, 2016].
SciFinder Database. CAS Registration No. 1070212-99-5. Chemical Abstract Services. American Chemical Society. [Last Accessed Jul. 25, 2016].
SciFinder Database. CAS Registration No. 1070291-29-0. Chemical Abstract Services. American Chemical Society. [Last Accessed Jul. 25, 2016].
SciFinder Database. CAS Registration No. 1087421-81-5. Chemical Abstract Services. American Chemical Society. [Last Accessed Jul. 25, 2016].
SciFinder Database. CAS Registration No. 1087511-95-2. Chemical Abstract Services. American Chemical Society. [Last Accessed Jul. 25, 2016].
SciFinder Database. CAS Registration No. 1087555-42-7. Chemical Abstract Services. American Chemical Society. [Last Accessed Jul. 25, 2016].
SciFinder Database. CAS Registration No. 1172227-82-5. Chemical Abstract Services. American Chemical Society. [Last Accessed Jul. 25, 2016].
SciFinder Database. CAS Registration No. 1172868-89-1. Chemical Abstract Services. American Chemical Society. [Last Accessed Jul. 25, 2016].
SciFinder Database. CAS Registration No. 1279839-42-7. Chemical Abstract Services. American Chemical Society. [Last Accessed Jul. 25, 2016].
SciFinder Database. CAS Registration No. 1279878-41-9. Chemical Abstract Services. American Chemical Society. [Last Accessed Jul. 25, 2016].
SciFinder Database. CAS Registration No. 1279879-10-5. Chemical Abstract Services. American Chemical Society. [Last Accessed Jul. 25, 2016].
SciFinder Database. CAS Registration No. 1279891-91-6. Chemical Abstract Services. American Chemical Society. [Last Accessed Jul. 25, 2016].
SciFinder Database. CAS Registration No. 1279891-93-8. Chemical Abstract Services. American Chemical Society. [Last Accessed Jul. 25, 2016].
SciFinder Database. CAS Registration No. 1331941-88-8. Chemical Abstract Services. American Chemical Society. [Last Accessed Jul. 25, 2016].
SciFinder Database. CAS Registration No. 1332163-49-1. Chemical Abstract Services. American Chemical Society. [Last Accessed Jul. 25, 2016].
SciFinder Database. CAS Registration No. 1332212-51-7. Chemical Abstract Services. American Chemical Society. [Last Accessed Jul. 25, 2016].
SciFinder Database. CAS Registration No. 1333648-57-9. Chemical Abstract Services. American Chemical Society. [Last Accessed Jul. 25, 2016].
SciFinder Database. CAS Registration No. 1333801-98-1. Chemical Abstract Services. American Chemical Society. [Last Accessed Jul. 25, 2016].
SciFinder Database. CAS Registration No. 1333912-79-0. Chemical Abstract Services. American Chemical Society. [Last Accessed Jul. 25, 2016].
SciFinder Database. CAS Registration No. 1340862-20-5. Chemical Abstract Services. American Chemical Society. [Last Accessed Jul. 25, 2016].
SciFinder Database. CAS Registration No. 1340896-72-1. Chemical Abstract Services. American Chemical Society. [Last Accessed Jul. 25, 2016].
SciFinder Database. CAS Registration No. 1341016-11-2. Chemical Abstract Services. American Chemical Society. [Last Accessed Jul. 25, 2016].
SciFinder Database. CAS Registration No. 1355539-18-2. Chemical Abstract Services. American Chemical Society. [Last Accessed Jul. 25, 2016].
SciFinder Database. CAS Registration No. 1355607-29-2. Chemical Abstract Services. American Chemical Society. [Last Accessed Jul. 25, 2016].
SciFinder Database. CAS Registration No. 1355640-11-7. Chemical Abstract Services. American Chemical Society. [Last Accessed Jul. 25, 2016].
SciFinder Database. CAS Registration No. 1355842-55-5. Chemical Abstract Services. American Chemical Society. [Last Accessed Jul. 25, 2016].
SciFinder Database. CAS Registration No. 1355890-97-9. Chemical Abstract Services. American Chemical Society. [Last Accessed Jul. 25, 2016].
SciFinder Database. CAS Registration No. 1360376-35-7. Chemical Abstract Services. American Chemical Society. [Last Accessed Jul. 25, 2016].
SciFinder Database. CAS Registration No. 1368359-39-0. Chemical Abstract Services. American Chemical Society. [Last Accessed Jul. 25, 2016].
SciFinder Database. CAS Registration No. 1369082-23-4. Chemical Abstract Services. American Chemical Society. [Last Accessed Jul. 25, 2016].
SciFinder Database. CAS Registration No. 1497548-79-4. Chemical Abstract Services. American Chemical Society. [Last Accessed Jul. 25, 2016].
SciFinder Database. CAS Registration No. 1497623-25-2. Chemical Abstract Services. American Chemical Society. [Last Accessed Jul. 25, 2016].
SciFinder Database. CAS Registration No. 1497669-55-2. Chemical Abstract Services. American Chemical Society. [Last Accessed Jul. 25, 2016].
SciFinder Database. CAS Registration No. 1501166-65-9. Chemical Abstract Services. American Chemical Society. [Last Accessed Jul. 25, 2016].

(56) References Cited

OTHER PUBLICATIONS

SciFinder Database. CAS Registration No. 1511831-42-7. Chemical Abstract Services. American Chemical Society. [Last Accessed Jul. 25, 2016].

* cited by examiner

DERIVATIVES AND METHODS OF TREATING HEPATITIS B INFECTIONS

RELATED APPLICATIONS

This application claims priority to U.S. Provisional Application No. 62/097,835, filed Dec. 30, 2014, and U.S. Provisional Application No. 62/163,150, filed May 18, 2015. The contents of these provisional applications are incorporated herein by reference in their entirety.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to sub-optimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for therapeutic agents that can increase the suppression of virus production and that can treat, ameliorate, and/or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

SUMMARY

Provided herein are compounds useful for the treatment of HBV infection in a subject in need thereof, having the structure:

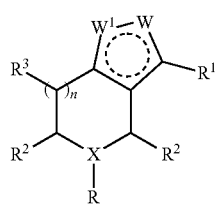

or a pharmaceutically acceptable salt thereof.

In one aspect, provided herein is a compound of Formula I:

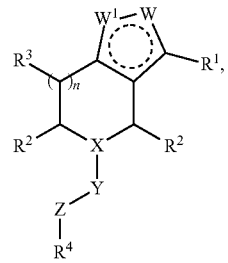

or a pharmaceutically acceptable salt thereof.

In an embodiment, the compound of Formula I is a compound of Formula II:

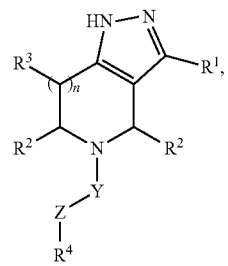

or a pharmaceutically acceptable salt thereof.

In another embodiment, the compound of Formula I is a compound of Formula III:

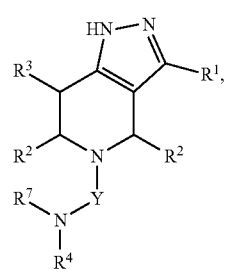

or a pharmaceutically acceptable salt thereof.

In another embodiment, the compound of Formula I is a compound of Formula IV:

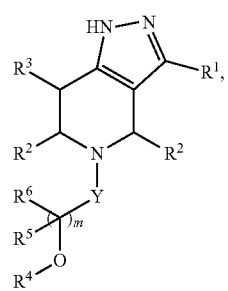

or a pharmaceutically acceptable salt thereof.

In another aspect, provided herein are pharmaceutical compositions comprising a compound of Formula I, II, III, or IV, or a pharmaceutically acceptable salt thereof, together with a pharmaceutically acceptable carrier.

In one aspect, provided herein is a method of treating an HBV infection in an individual in need thereof, comprising administering to the individual a therapeutically effective amount of a compound of Formula I, II, III, or IV, or a pharmaceutically acceptable salt thereof.

In another aspect, provided herein is a method of eradicating an HBV infection in an individual in need thereof, comprising administering to the individual a therapeutically effective amount of a compound of Formula I, II, III, or IV, or a pharmaceutically acceptable salt thereof.

In another aspect, provided herein is a method of reducing the viral load associated with an HBV infection in an individual in need thereof, comprising administering to the individual a therapeutically effective amount of a compound of Formula I, II, III, or IV, or a pharmaceutically acceptable salt thereof.

In another aspect, provided herein is a method of reducing reoccurrence of an HBV infection in an individual in need thereof, comprising administering to the individual a therapeutically effective amount of a compound of Formula I, II, III, or IV, or a pharmaceutically acceptable salt thereof.

In another aspect, provided herein is a method of inhibiting or reducing the formation or presence of HBV DNA-containing particles or HBV RNA-containing particles in an individual in need thereof, comprising administering to the individual a therapeutically effective amount of a compound of Formula I, II, III, or IV, or a pharmaceutically acceptable salt thereof.

In another aspect, provided herein is a method of reducing an adverse physiological impact of an HBV infection in an individual in need thereof, comprising administering to the individual a therapeutically effective amount of a compound of Formula I, II, III, or IV, or a pharmaceutically acceptable salt thereof.

In another aspect, provided herein is a method of inducing remission of hepatic injury from an HBV infection in an individual in need thereof, comprising administering to the individual a therapeutically effective amount of a compound of Formula I, II, III, or IV, or a pharmaceutically acceptable salt thereof.

In another aspect, provided herein is a method of reducing the physiological impact of long-term antiviral therapy for HBV infection in an individual in need thereof, comprising administering to the individual a therapeutically effective amount of a compound of Formula I, II, III, or IV, or a pharmaceutically acceptable salt thereof.

In another aspect, provided herein is a method of prophylactically treating an HBV infection in an individual in need thereof, wherein the individual is afflicted with a latent HBV infection, comprising administering to the individual a therapeutically effective amount of a compound of Formula I, II, III, or IV, or a pharmaceutically acceptable salt thereof.

In an embodiment, the methods provided herein can further comprise administering to the individual at least one additional therapeutic agent selected from the group consisting of an HBV polymerase inhibitor, immunomodulatory agents, pegylated interferon, viral entry inhibitor, viral maturation inhibitor, literature-described capsid assembly modulator, reverse transcriptase inhibitor, a cyclophilin/TNF inhibitor, a TLR-agonist, an HBV vaccine, agents of distinct or unknown mechanism, and a combination thereof. In a further embodiment, the methods provided herein allow for administering of the at least one additional therapeutic agent at a lower dose or frequency as compared to the administering of the at least one additional therapeutic agent alone that is required to achieve similar results in prophylactically treating an HBV infection in an individual in need thereof.

In another embodiment, the methods provided herein reduce the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In another embodiment, the methods provided herein cause a lower incidence of viral mutation and/or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In another embodiment, the methods provided herein further comprise administering to the individual at least one HBV vaccine, a nucleoside HBV inhibitor, an interferon, or any combination thereof.

In an aspect, provided herein is a method of treating an HBV infection in an individual in need thereof, comprising reducing the HBV viral load by administering to the individual a therapeutically effective amount of a compound of Formula I, II, III, or IV, or a pharmaceutically acceptable salt thereof, alone or in combination with a reverse transcriptase inhibitor; and further administering to the individual a therapeutically effective amount of HBV vaccine.

In an embodiment, the methods provided herein further comprise monitoring the HBV viral load of the subject, wherein the method is carried out for a period of time such that the HBV virus is undetectable.

DETAILED DESCRIPTION

Provided herein are compounds, e.g., the compounds of Formulas I, II, III, or IV, or pharmaceutically acceptable salts thereof, that are useful in the treatment and prevention of HBV infection in subject. In a non-limiting aspect, these compounds may modulate or disrupt HBV assembly and other HBV core protein functions necessary for HBV replication or the generation of infectious particles, may inhibit the production of infectious virus particles or infection, or may interact with HBV capsid to afford defective viral particles with greatly reduced infectivity or replication capacity. In other words, the compounds provided herein may act as capsid assembly modulators. The compounds provided herein have potent antiviral activity, exhibit favorable metabolic properties, tissue distribution, safety and pharmaceutical profiles, and are suitable for use in humans.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, the appropriate timing of capsid assembly and disassembly, the appropriate capsid stability and the function of core protein have been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The high functional constraints on the multi-functional HBV core/capsid protein is consistent with a high sequence conservation, as many mutations are deleterious to function. Indeed, the core/capsid protein sequences are >90% identical across HBV genotypes and show only a small number of polymorphic residues. Resistance selection to HBV core/capsid protein binding compounds may therefore be difficult to select without large impacts on virus replication fitness.

Reports describing compounds that bind viral capsids and inhibit replication of HIV, rhinovirus and HBV provide strong pharmacological proof of concept for viral capsid proteins as antiviral drug targets.

In one aspect, the compounds provided herein are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, virus egress and/or infection of target cells. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds provided herein cause failure of the formation of capsids of optimal stability, affecting efficient uncoating and/or disassembly of viruses (e.g., during infectivity).

In one embodiment, the compounds provided herein disrupt and/or accelerate capsid assembly and/or disassembly when the capsid protein is immature. In another embodiment, the compounds provided herein disrupt and/or accelerate capsid assembly and/or disassembly when the capsid protein is mature. In yet another embodiment, the compounds provided herein disrupt and/or accelerate capsid assembly and/or disassembly during viral infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds proided herein can be used in methods of modulating (e.g., inhibiting or disrupting) the activity, stability, function, and viral replication properties of HBV cccDNA. In yet another embodiment, the compounds of the invention can be used in methods of diminishing or preventing the formation of HBV cccDNA.

In another embodiment, the the compounds provided herein can be used in methods of modulating (e.g., inhibiting or disrupting) the activity of HBV cccDNA. In yet another embodiment, the compounds of the invention can be used in methods of diminishing the formation of HBV cccDNA.

In another embodiment, the the compounds provided herein can be used in methods of modulating, inhibiting, or disrupting the generation or release of HBV RNA particles from within the infected cell. In a further embodiment, the total burden (or concentration) of HBV RNA particles is modulated. In a preferred embodiment, the total burden of HBV RNA is diminished.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity and/or is lethal to the virus.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_6$-alkyl means one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkenyl," denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "haloalkyl" refers to alkyl radicals wherein any one or more of the alkyl carbon atoms is substituted with halo as defined above. Haloalkyl embraces monohaloalkyl, dihaloalkyl, and polyhaloalkyl radicals. The term "haloalkyl" includes, but is not limited to, fluoromethyl, difluoromethyl, trifluoromethyl, chloromethyl, dichloromethyl, trichloromethyl, and pentafluoroethyl.

As used herein, the term "cycloalkyl" refers to a mono cyclic or polycyclic nonaromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_3$-$C_{10}$-cycloalkyl), groups having 3 to 8 ring atoms ($C_3$-$C_8$-cycloalkyl), groups having 3 to 7 ring atoms ($C_3$-$C_7$-cycloalkyl), and groups having 3 to 6 ring atoms ($C_3$-$C_6$-cycloalkyl). Illustrative examples of cycloalkyl groups include, but are not limited to, the following moieties:

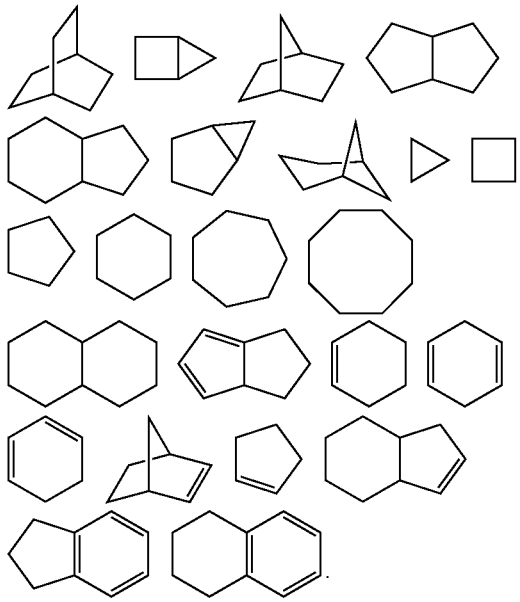

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S, and N. In one embodiment, each heterocyclyl group has from 3 to 10 atoms in its ring system, with the proviso that the ring of said group does not contain two adjacent O or S atoms. Heterocyclyl substituents may be alternatively defined by the number of carbon atoms, e.g., $C_2$-$C_8$-heterocyclyl indicates the number of carbon atoms contained in the heterocyclic group without including the number of heteroatoms. For example, a $C_2$-$C_8$-heterocyclyl will include an additional one to four heteroatoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

An example of a 3-membered heterocyclyl group includes, and is not limited to, aziridine. Examples of 4-membered heterocycloalkyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups are:

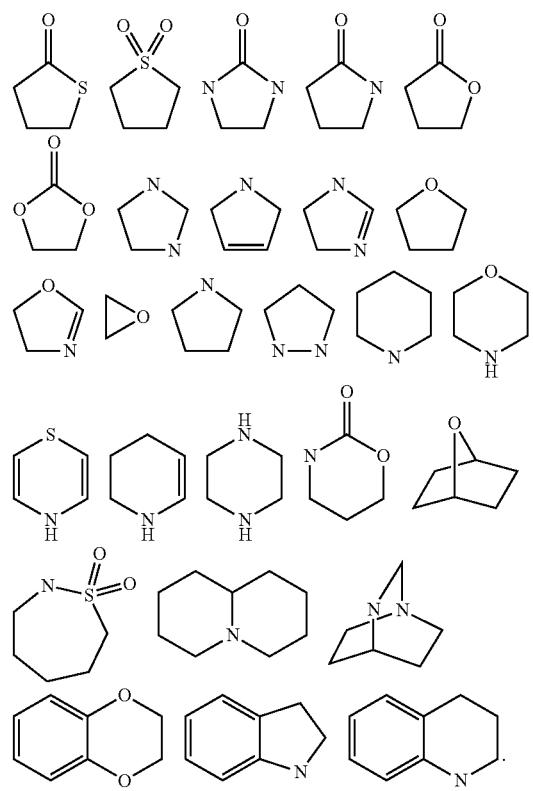

Examples of heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. A polycyclic heteroaryl may include one or more rings that are partially saturated. Non-limiting examples of heteroaryls include:

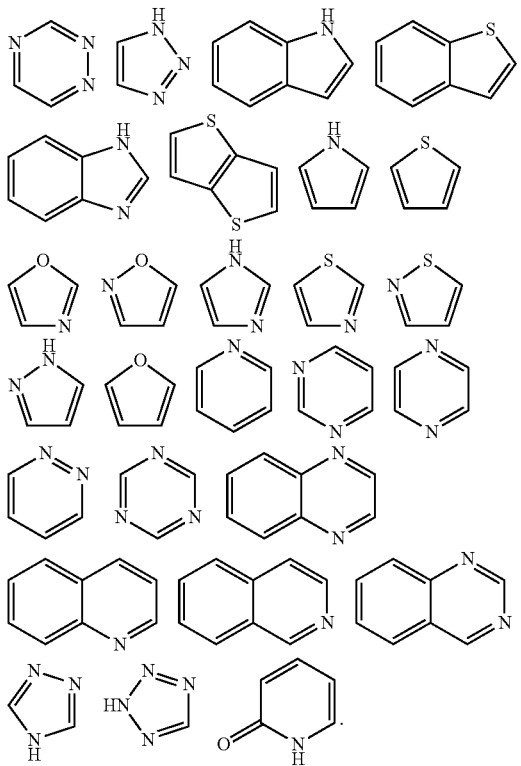

Additional non-limiting examples of heteroaryl groups include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

Compounds of the Invention

Provided herein are compounds useful for the treatment of HBV infection in a subject in need thereof, having the structure:

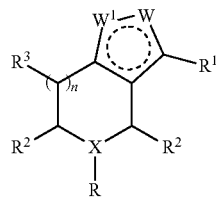

or pharmaceutically acceptable salts thereof.

In one aspect, provided herein is a compound of Formula Ia

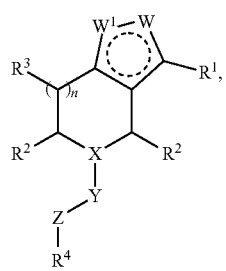

Ia or a pharmaceutically acceptable salt thereof,
wherein
$W^1$ and W are each independently selected from N, $NR^a$, and $CR^a$, wherein one of $W^1$ and W is $NR^a$;
X is N or $CR^b$;
Y is selected from a bond, —C(O)—, and —$SO_2$—;
Z is selected from —$(CR^5R^6)_m$—, —$(CR^5R^6)_mO$—, —$(CR^5R^6)_mCR^5$=$CR^5$—, —$(CR^5R^6)_m$—$C_3$-$C_6$-cycloalkylene-, and —$(CR^5R^6)_m$—$NR^7$—;
$R^1$ is selected from $C_6$-$C_{12}$-aryl, $C_1$-$C_9$-heteroaryl, $C_3$-$C_8$-cycloalkyl, $C_2$-$C_8$-heterocyclyl, —$OR^c$, $C_1$-$C_6$-alkyl, C(O)OR$^c$, C(O)R$^c$, C(O)NR$^d$R$^e$, NR$^d$C(O)R$^c$, —OC(O)R$^c$, halo, and $C_2$-$C_8$-alkenyl, wherein alkyl, aryl, heteroaryl, cycloalkyl, heterocyclyl, and alkenyl are optionally substituted with 1, 2, 3, or 4 groups each independently selected from —OH, halo, $C_1$-$C_6$-alkyl, $C_1$-$C_6$-haloalkyl, —O—$C_1$-$C_6$-alkyl, and $C_1$-$C_6$-alkyl-OH;
$R^2$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;
$R^3$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $C_1$-$C_6$-alkyl, $(CR^8R^9)_p$—$C_3$-$C_8$-cycloalkyl, $(CR^8R^9)_p$—$C_2$-$C_8$-heterocyclyl, $(CR^8R^9)_p$—$C_6$-$C_{12}$-aryl, and $(CR^8R^9)_p$—$C_1$-$C_9$-heteroaryl, wherein alkyl, cycloalkyl, heterocyclyl, aryl, heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, C(O)N(R$^f$)$_2$, C(O)OR$^f$, —OCH$_2$C(O)OR$^f$, —SO$_2$R$^f$, $C_1$-$C_6$-alkyl-OH, and $C_3$-$C_8$-cycloalkyl;

$R^5$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

alternatively, $R^4$ and $R^5$ are optionally joined to form a heterocyclic ring;

$R^6$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^7$ is selected from H, $C_1$-$C_6$-alkyl, and $C_1$-$C_6$-alkyl-OH;

$R^8$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^9$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^a$ is selected from H, $C_1$-$C_6$-alkyl, and $C_1$-$C_6$-alkyl-OH;
$R^b$ is selected from H and $C_1$-$C_6$-alkyl;
$R^c$ is selected from H, $C_1$-$C_6$-alkyl, $C_1$-$C_6$-alkyl-OH, $C_3$-$C_8$-cycloalkyl, $C_2$-$C_8$-heterocyclyl, $C_6$-$C_{12}$-aryl, and $C_1$-$C_9$-heteroaryl;
$R^d$ is selected from H, $C_1$-$C_6$-alkyl, and $C_1$-$C_6$-alkyl-OH;
$R^e$ is selected from H, $C_1$-$C_6$-alkyl, $C_1$-$C_6$-alkyl-OH, $C_3$-$C_8$-cycloalkyl, $C_2$-$C_8$-heterocyclyl, $C_6$-$C_{12}$-aryl, $C_1$-$C_9$-heteroaryl, and —O—$C_1$-$C_6$-alkyl;

alternatively, $R^d$ and $R^e$ are optionally joined to form a heterocyclic ring;

$R^f$ is, at each occurrence, independently selected from H and $C_1$-$C_6$-alkyl;

m is 0, 1, 2, 3, or 4;
n is 0, 1, 2, or 3; and
p is 0, 1, 2, 3, or 4.

In another aspect, provided herein is a compound of Formula I or a pharmaceutically acceptable salt thereof,
wherein
$W^1$ and W are each independently selected from N, NR$^a$, and CR$^a$, wherein one of $W^1$ and W is NR$^a$;
X is N or CR$^b$;
Y is selected from a bond, —C(O)—, and —SO$_2$—;
Z is selected from —(CR$^5$R$^6$)$_m$—, —(CR$^5$R$^6$)$_m$O—, —(CR$^5$R$^6$)$_m$CR$^5$=CR$^5$—, —(CR$^5$R$^6$)$_m$—$C_3$-$C_6$-cycloalkylene-, and —(CR$^5$R$^6$)$_m$—NR$^7$—;
$R^1$ is selected from C(O)OR$^c$, C(O)R$^c$, C(O)NR$^d$R$^e$, NR$^d$C(O)R$^c$, —OC(O)R$^c$, —C(O)NR$^d$OR$^e$; and —C(O)NR$^d$N(R$^d$)$_2$;

$R^2$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^3$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $C_1$-$C_6$-alkyl, $(CR^8R^9)_p$—$C_3$-$C_8$-cycloalkyl, $(CR^8R^9)_p$—$C_2$-$C_8$-heterocyclyl, $(CR^8R^9)_p$—$C_6$-$C_{12}$-aryl, and $(CR^8R^9)_p$—$C_1$-$C_9$-heteroaryl, wherein alkyl, cycloalkyl, heterocyclyl, aryl, heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, C(O)N(R$^f$)$_2$, C(O)OR$^f$, —OCH$_2$C(O)OR$^f$, —SO$_2$R$^f$, and $C_1$-$C_6$-alkyl-OH;

$R^5$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

alternatively, $R^4$ and $R^5$ are optionally joined to form a heterocyclic ring;

$R^6$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^7$ is selected from H, $C_1$-$C_6$-alkyl, and $C_1$-$C_6$-alkyl-OH;

$R^8$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^9$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^a$ is selected from H, $C_1$-$C_6$-alkyl, and $C_1$-$C_6$-alkyl-OH;
$R^b$ is selected from H and $C_1$-$C_6$-alkyl;
$R^c$ is selected from H, $C_1$-$C_6$-alkyl, $C_1$-$C_6$-alkyl-OH, $C_0$-$C_6$-alkyl-$C_3$-$C_8$-cycloalkyl, $C_2$-$C_8$-heterocyclyl, $C_6$-$C_{12}$-aryl, and $C_1$-$C_9$-heteroaryl, wherein cycloalkyl, heterocyclyl, aryl, and heteroaryl are optionally substituted with 1, 2, or 3 groups, each independently selected from —OH, halo, CN, $C_1$-$C_6$-alkyl, $C_1$-$C_6$-haloalkyl, and —O—$C_1$-$C_6$-alkyl;

$R^d$ is selected from H, $C_1$-$C_6$-alkyl, and $C_1$-$C_6$-alkyl-OH;
$R^e$ is selected from H, $C_1$-$C_6$-alkyl, $C_1$-$C_6$-alkyl-OH, $C_1$-$C_6$-alkyl-OC$_1$-$C_6$-alkyl, $C_0$-$C_6$-alkyl-$C_3$-$C_8$-cycloalkyl, $C_2$-$C_8$-heterocyclyl, $C_6$-$C_{12}$-aryl, and $C_1$-$C_9$-heteroaryl, wherein cycloalkyl, heterocyclyl, aryl, and heteroaryl are optionally substituted with 1, 2, or 3 groups, each independently selected from —OH, halo, CN, $C_1$-$C_6$-alkyl, $C_1$-$C_6$-haloalkyl, and —O—$C_1$-$C_6$-alkyl;

alternatively, $R^d$ and $R^e$ are optionally joined to form a heterocyclic ring, which is optionally substituted with 1, 2, or 3 groups, each independently selected from —OH, halo, CN, $C_1$-$C_6$-alkyl, $C_1$-$C_6$-haloalkyl, and —O—$C_1$-$C_6$-alkyl;

$R^f$ is, at each occurrence, independently selected from H and $C_1$-$C_6$-alkyl;

m is 0, 1, 2, 3, or 4;
n is 0, 1, 2, or 3; and
p is 0, 1, 2, 3, or 4.

In an embodiment of the compound of Formula I,
$W^1$ and W are each independently selected from N, NR$^a$, and CR$^a$, wherein one of $W^1$ and W is NR$^a$;
X is N or CR$^b$;
Y is selected from a bond, —C(O)—, and —SO$_2$—;
Z is selected from —(CR$^5$R$^6$)$_m$—, —(CR$^5$R$^6$)$_m$O—, —(CR$^5$R$^6$)$_m$CR$^5$=CR$^5$—, —(CR$^5$R$^6$)$_m$—$C_3$-$C_6$-cycloalkylene-, and —(CR$^5$R$^6$)$_m$—NR$^7$—;
$R^1$ is selected from C(O)OR$^c$, C(O)R$^c$, C(O)NR$^d$R$^e$, NR$^d$C(O)R$^c$, —OC(O)R$^c$, —C(O)NR$^d$OR$^e$, and —C(O)NR$^d$N(R$^d$)$_2$;

$R^2$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^3$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $C_1$-$C_6$-alkyl, $(CR^8R^9)_p$—$C_3$-$C_8$-cycloalkyl, $(CR^8R^9)_p$—$C_2$-$C_8$-heterocyclyl, $(CR^8R^9)_p$—$C_6$-$C_{12}$-aryl, and $(CR^8R^9)_p$—$C_1$-$C_9$-heteroaryl, wherein alkyl, cycloalkyl, heterocyclyl, aryl, heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —$OCH_2C(O)OR^f$, —$SO_2R^f$, and $C_1$-$C_6$-alkyl-OH;

$R^5$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

alternatively, $R^4$ and $R^5$ are optionally joined to form a heterocyclic ring;

$R^6$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^7$ is selected from H, $C_1$-$C_6$-alkyl, and $C_1$-$C_6$-alkyl-OH;

$R^8$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^9$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^a$ is selected from H, $C_1$-$C_6$-alkyl, and $C_1$-$C_6$-alkyl-OH;

$R^b$ is selected from H and $C_1$-$C_6$-alkyl;

$R^c$ is selected from H, $C_1$-$C_6$-alkyl, $C_1$-$C_6$-alkyl-OH, $C_1$-$C_6$-alkyl-$C_3$-$C_8$-cycloalkyl, $C_2$-$C_8$-heterocyclyl, $C_6$-$C_{12}$-aryl, and $C_1$-$C_9$-heteroaryl, wherein cycloalkyl, heterocyclyl, aryl, and heteroaryl are optionally substituted with 1, 2, or 3 groups, each independently selected from —OH, halo, CN, $C_1$-$C_6$-alkyl, $C_1$-$C_6$-haloalkyl, and —O—$C_1$-$C_6$-alkyl;

$R^d$ is selected from H, $C_1$-$C_6$-alkyl, and $C_1$-$C_6$-alkyl-OH;

$R^e$ is selected from H, $C_1$-$C_6$-alkyl, $C_1$-$C_6$-alkyl-OH, $C_1$-$C_6$-alkyl-$OC_1$-$C_6$-alkyl, $C_0$-$C_6$-alkyl-$C_3$-$C_8$-cycloalkyl, $C_2$-$C_8$-heterocyclyl, $C_6$-$C_{12}$-aryl, and $C_1$-$C_9$-heteroaryl, wherein cycloalkyl, heterocyclyl, aryl, and heteroaryl are optionally substituted with 1, 2, or 3 groups, each independently selected from —OH, halo, CN, $C_1$-$C_6$-alkyl, $C_1$-$C_6$-haloalkyl, and —O—$C_1$-$C_6$-alkyl;

alternatively, $R^d$ and $R^e$ are optionally joined to form a heterocyclic ring, which is optionally substituted with 1 or 2 groups, each independently selected from —OH, halo, CN, $C_1$-$C_6$-alkyl, $C_1$-$C_6$-haloalkyl, and —O—$C_1$-$C_6$-alkyl;

$R^f$ is, at each occurrence, independently selected from H and $C_1$-$C_6$-alkyl;

m is 0, 1, 2, 3, or 4;

n is 0, 1, 2, or 3; and p is 0, 1, 2, 3, or 4.

In another embodiment of the compound of Formula I, $W^1$ is $NR^a$ and W is N or $CR^a$. In a further embodiment, $W^1$ is NH.

In another embodiment of the compound of Formula I, $W^1$ is N or $CR^a$ and W is $NR^a$.

In another embodiment of the compound of Formula I, X is N.

In an embodiment of the compound of Formula I, Y is —C(O)— or —$SO_2$—.

In a further embodiment of the compound of Formula I, Z is —$(CR^5R^6)_m$—, —$(CR^5R^6)_mO$—, or —$(CR^5R^6)_m$—$NR^7$—.

In an embodiment of the compound of Formula I, m is 0 or 1;

$R^5$ is H, —OH, or $C_1$-$C_6$-alkyl;

$R^6$ is H or $C_1$-$C_6$-alkyl; and $R^7$ is H or $C_1$-$C_6$-alkyl.

In another embodiment of the compound of Formula I, $R^1$ is $C(O)OR^c$, $C(O)R^c$, $C(O)NR^dR^e$, —$C(O)NR^dOR^e$, or —$C(O)NR^dN(R^d)_2$.

In an embodiment of the compound of Formula I, $R^1$ is $C(O)NR^dR^e$, wherein $R^d$ is selected from H, $C_1$-$C_6$-alkyl, and $C_1$-$C_6$-alkyl-OH and $R^e$ is selected from H, $C_1$-$C_6$-alkyl, $C_1$-$C_6$-alkyl-OH, $C_3$-$C_8$-cycloalkyl, $C_2$-$C_8$-heterocyclyl, $C_6$-$C_{12}$-aryl, $C_1$-$C_9$-heteroaryl, and —O—$C_1$-$C_6$-alkyl alternatively wherein $R^d$ and $R^e$ optionally form a heterocyclic ring; or $R^1$ is $C(O)NR^dOR^e$, wherein $R^d$ is selected from H, $C_1$-$C_6$-alkyl, and $C_1$-$C_6$-alkyl-OH and $R^e$ is selected from, $C_1$-$C_6$-alkyl-$OC_1$-$C_6$-alkyl, $C_0$-$C_6$-alkyl-$C_3$-$C_8$-cycloalkyl, $C_2$-$C_8$-heterocyclyl, $C_6$-$C_{12}$-aryl, and $C_1$-$C_9$-heteroaryl, wherein cycloalkyl, heterocyclyl, aryl, and heteroaryl are optionally substituted with 1, 2, or 3 groups, each independently selected from —OH, halo, CN, $C_1$-$C_6$-alkyl, $C_1$-$C_6$-haloalkyl, and —O—$C_1$-$C_6$-alkyl.

In an embodiment of the compound of Formula I, $R^d$ and $R^e$ are optionally joined to form a $C_3$-$C_5$ heterocyclic ring.

In an embodiment of the compound of Formula I, each $R^2$ is independently selected from H or $C_1$-$C_6$-alkyl. In a further embodiment of the compound of Formula I, $R^2$ is H.

In an embodiment of the compound of Formula I, $R^3$ is H.

In an embodiment of the compound of Formula I, $R^4$ is $(CR^8R^9)_p$—$C_3$-$C_8$-cycloalkyl, $(CR^8R^9)_p$—$C_2$-$C_8$-heterocyclyl, $(CR^8R^9)_p$—$C_6$-$C_{12}$-aryl, or $(CR^8R^9)_p$—$C_1$-$C_9$-heteroaryl, wherein cycloalkyl, heterocyclyl, aryl, and heteroaryl are optionally substituted with 1, 2, 3, or 4 groups each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —$OCH_2C(O)OR^f$, —$SO_2R^f$, and $C_1$-$C_6$-alkyl-OH.

In another embodiment of the compound of Formula I, $R^4$ is $(CR^8R^9)_p$—$C_6$-$C_{12}$-aryl, or $(CR^8R^9)_p$—$C_1$-$C_9$-heteroaryl, wherein aryl, and heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —$OCH_2C(O)OR^f$, —$SO_2R^f$, and $C_1$-$C_6$-alkyl-OH.

In another embodiment of the compound of Formula I, p is 0 or 1;

$R^8$ is H, —OH, or $C_1$-$C_6$-alkyl; and $R^9$ is H or $C_1$-$C_6$-alkyl.

In an embodiment of the compound of Formula I, n is 1.

In another embodiment of the compound of Formula I,

X is N;

Y is —C(O)—;

Z is $NR^7$; and $R^7$ is H or $C_{1-4}$-alkyl.

In a further embodiment of the compound of Formula I,

X is N;

Y is —C(O)—;

Z is $NR^7$;

$R^7$ is H or $C_{1-4}$-alkyl; and n is 1.

Also provided herein is a compound of Formula I, having the structure of Formula II (also referred to as "a compound of Formula II"):

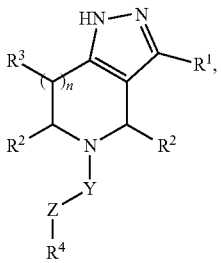

II or a pharmaceutically acceptable salt thereof.

In an embodiment of the compound of Formula II, Y is —C(O)— or —SO$_2$—.

In an embodiment of the compound of Formula II, Z is —(CR$^5$R$^6$)$_m$—, —(CR$^5$R$^6$)$_m$O— or —(CR$^5$R$^6$)$_m$—NR$^7$—.

In an embodiment of the the compound of Formula II,
m is 0 or 1;
R$^5$ is H, —OH, or C$_1$-C$_6$-alkyl;
R$^6$ is H or C$_1$-C$_6$-alkyl; and
R$^7$ is H or C$_1$-C$_6$-alkyl.

In an embodiment of the compound of Formula II, R$^1$ is C(O)OR$^c$, C(O)R$^c$, C(O)NR$^d$R$^e$, —C(O)NR$^d$OR$^e$, or —C(O)NR$^d$N(R$^d$)$_2$.

In an embodiment of the compound of Formula II, R$^1$ is C(O)NR$^d$R$^e$, wherein R$^d$ is selected from H, C$_1$-C$_6$-alkyl, and C$_1$-C$_6$-alkyl-OH and R$^e$ is selected from H, C$_1$-C$_6$-alkyl, C$_1$-C$_6$-alkyl-OH, C$_3$-C$_8$-cycloalkyl, C$_2$-C$_8$-heterocyclyl, C$_6$-C$_{12}$-aryl, C$_1$-C$_9$-heteroaryl, and —O—C$_1$-C$_6$-alkyl alternatively wherein R$^d$ and R$^e$ optionally form a heterocyclic ring; or R$^1$ is C(O)NR$^d$OR$^e$, wherein R$^d$ is selected from H, C$_1$-C$_6$-alkyl, and C$_1$-C$_6$-alkyl-OH and R$^e$ is selected from, C$_1$-C$_6$-alkyl-OC$_1$-C$_6$-alkyl, C$_0$-C$_6$-alkyl-C$_3$-C$_8$-cycloalkyl, C$_2$-C$_8$-heterocyclyl, C$_6$-C$_{12}$-aryl, and C$_1$-C$_9$-heteroaryl, wherein cycloalkyl, heterocyclyl, aryl, and heteroaryl are optionally substituted with 1, 2, or 3 groups, each independently selected from —OH, halo, CN, C$_1$-C$_6$-alkyl, C$_1$-C$_6$-haloalkyl, and —O—C$_1$-C$_6$-alkyl.

In an embodiment of the compound of Formula II, R$^d$ and R$^e$ are optionally joined to form a C$_3$-C$_5$ heterocyclic ring.

In an embodiment of the compound of Formula II, each R$^2$ is independently selected from H or C$_1$-C$_4$-alkyl. In a further embodiment of the compound of Formula II, R$^2$ is H.

In an embodiment of the compound of Formula II R$^3$ is H.

In an embodiment of the compound of Formula II, R$^4$ is (CR$^8$R$^9$)$_p$—C$_3$-C$_8$-cycloalkyl, (CR$^8$R$^9$)$_p$—C$_2$-C$_8$-heterocyclyl, (CR$^8$R$^9$)$_p$—C$_6$-C$_{12}$-aryl, or (CR$^8$R$^9$)$_p$—C$_1$-C$_9$-heteroaryl, wherein cycloalkyl, heterocyclyl, aryl, and heteroaryl are optionally substituted with 1, 2, 3, or 4 groups, each independently selected from —OH, halo, CN, C$_1$-C$_6$-alkyl, C$_1$-C$_6$-haloalkyl, —O—C$_1$-C$_6$-alkyl, C(O)N(R$^f$)$_2$, C(O)OR$^f$, —OCH$_2$C(O)OR$^f$, —SO$_2$R$^f$, and C$_1$-C$_6$-alkyl-OH.

In an embodiment of the compound of Formula II, R$^4$ is (CR$^8$R$^9$)$_p$—C$_6$-C$_{12}$-aryl, or (CR$^8$R$^9$)$_p$—C$_1$-C$_9$-heteroaryl, and wherein aryl and heteroaryl are optionally substituted with 1, 2, 3, or 4 groups, each independently selected from —OH, halo, CN, C$_1$-C$_6$-alkyl, C$_1$-C$_6$-haloalkyl, —O—C$_1$-C$_6$-alkyl, C(O)N(R$^f$)$_2$, C(O)OR$^f$, —OCH$_2$C(O)OR$^f$, —SO$_2$R$^f$, and C$_1$-C$_6$-alkyl-OH.

In an embodiment of the compound of Formula II, R$^4$ is (CR$^8$R$^9$)$_p$—C$_6$-C$_{12}$-aryl, or (CR$^8$R$^9$)$_p$—C$_1$-C$_9$-heteroaryl, and wherein aryl and heteroaryl are optionally substituted with 1 or 2 groups, each independently selected from —OH, halo, CN, C$_1$-C$_6$-alkyl, C$_1$-C$_6$-haloalkyl, —O—C$_1$-C$_6$-alkyl, and C$_1$-C$_6$-alkyl-OH.

In a further embodiment of the compound of Formula II, R$^4$ is C$_6$-C$_{12}$-aryl, wherein aryl is optionally substituted with 1 or 2 groups, each independently selected from —OH, halo, CN, C$_1$-C$_6$-alkyl, C$_1$-C$_6$-haloalkyl, —O—C$_1$-C$_6$-alkyl, and C$_1$-C$_6$-alkyl-OH.

In an embodiment of the compound of Formula II,
Y is —C(O)—;
Z is —(CR$^5$R$^6$)$_m$—, —(CR$^5$R$^6$)$_m$O— or —(CR$^5$R$^6$)$_m$—NR$^7$—;
R$^1$ is C(O)OR$^c$, C(O)R$^c$, C(O)NR$^d$R$^e$, —C(O)NR$^d$OR$^e$, or —C(O)NR$^d$N(R$^d$)$_2$;
each R$^2$ is independently selected from H or C$_1$-C$_4$-alkyl; and
R$^3$ is H;
R$^4$ is (CR$^8$R$^9$)$_p$—C$_6$-C$_{12}$-aryl, or (CR$^8$R$^9$)$_p$—C$_1$-C$_9$-heteroaryl, and wherein aryl and heteroaryl are optionally substituted with 1, 2, 3, or 4 groups, each independently selected from —OH, halo, CN, C$_1$-C$_6$-alkyl, C$_1$-C$_6$-haloalkyl, —O—C$_1$-C$_6$-alkyl, C(O)N(R$^f$)$_2$, C(O)OR$^f$, —OCH$_2$C(O)OR$^f$, —SO$_2$R$^f$, and C$_1$-C$_6$-alkyl-OH;
R$^5$ is H, —OH, or C$_1$-C$_6$-alkyl;
R$^6$ is H or C$_1$-C$_6$-alkyl;
R$^7$ is H or C$_1$-C$_6$-alkyl;
R$^8$ is, at each occurrence, independently selected from H, —OH, halo, and C$_1$-C$_6$-alkyl;
R$^9$ is, at each occurrence, independently selected from H, —OH, halo, and C$_1$-C$_6$-alkyl;
R$^c$ is C$_1$-C$_6$-alkyl;
R$^d$ is selected from H, C$_1$-C$_6$-alkyl, and C$_1$-C$_6$-alkyl-OH;
R$^e$ is selected from H, C$_1$-C$_6$-alkyl, C$_1$-C$_6$-alkyl-OH, C$_1$-C$_6$-alkyl-OC$_1$-C$_6$-alkyl, C$_0$-C$_6$-alkyl-C$_3$-C$_8$-cycloalkyl, and C$_2$-C$_8$-heterocyclyl, wherein cycloalkyl and heterocyclyl are optionally substituted with 1 or 2 groups, each independently selected from —OH, halo, CN, C$_1$-C$_6$-alkyl, C$_1$-C$_6$-haloalkyl, and —O—C$_1$-C$_6$-alkyl;
alternatively, R$^d$ and R$^e$ are optionally joined to form a heterocyclic ring, which is optionally substituted with 1, 2, or 3 groups, each independently selected from —OH, halo, CN, C$_1$-C$_6$-alkyl, C$_1$-C$_6$-haloalkyl, and —O—C$_1$-C$_6$-alkyl.
R$^f$ is, at each occurrence, independently selected from H and C$_1$-C$_6$-alkyl;
m is 0 or 1;
n is 1; and
p is 0, 1, or 2.

In an embodiment of this embodiment, R$^1$ is C(O)OR$^c$, C(O)R$^c$, C(O)NR$^d$R$^e$, or —C(O)NR$^d$OR$^e$.

In yet a further embodiment of this embodiment, R$^1$ is C(O)NR$^d$R$^e$, or —C(O)NR$^d$OR$^e$.

In an embodiment of this embodiment, R$^4$ is (CR$^8$R$^9$)$_p$—C$_6$-C$_{12}$-aryl, or (CR$^8$R$^9$)$_p$—C$_1$-C$_9$-heteroaryl, and wherein aryl and heteroaryl are optionally substituted with 1, 2, or 3 groups, each independently selected from —OH, halo, CN, C$_1$-C$_6$-alkyl, C$_1$-C$_6$-haloalkyl, —O—C$_1$-C$_6$-alkyl, and C$_1$-C$_6$-alkyl-OH.

In an embodiment of the compound of Formula II,
p is 0 or 1;
R$^8$ is independently selected from H, —OH, and C$_1$-C$_6$-alkyl; and
R$^9$ is independently selected from H and C$_1$-C$_6$-alkyl.

In an embodiment of the compound of Formula II, n is 1.
In an embodiment of the compound of Formula II,
Y is —C(O)—;
Z is NR$^7$; and
R$^7$ is H or C$_{1-4}$-alkyl.

In an embodiment of the compound of Formula II,
Y is —C(O)—;
Z is NR$^7$;
R$^7$ is H or C$_{1-4}$-alkyl; and
n is 1.

Also provided herein is a compound of Formula I, having the structure of Formula III (also referred to as "a compound of Formula III"):

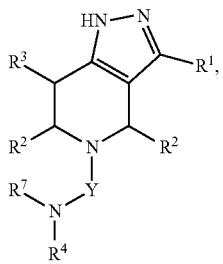

III or a pharmaceutically acceptable salt thereof, wherein
Y is —C(O)— or —SO$_2$—;
R$^1$ is C(O)OR$^c$, C(O)R$^c$, C(O)NR$^d$R$^e$, —C(O)NR$^d$OR$^e$, or —C(O)NR$^d$N(R$^d$)$_2$;
R$^2$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^3$ is selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^4$ is selected from (CR$^8$R$^9$)$_p$—C$_1$-C$_9$-heteroaryl, (CR$^8$R$^9$)$_p$—C$_6$-C$_{12}$-aryl, and C$_3$-C$_8$-cycloalkyl wherein heteroaryl, aryl, and cycloalkyl are optionally substituted with 1, 2, or 3 groups, each independently selected from —OH, halo, CN, C$_1$-C$_6$-alkyl, C$_1$-C$_6$-haloalkyl, —O—C$_1$-C$_6$-alkyl, C$_1$-C$_6$-alkyl-OH, and C$_3$-C$_8$-cycloalkyl.
R$^7$ is selected from H, C$_1$-C$_6$-alkyl, and C$_1$-C$_6$-alkyl-OH;
R$^8$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^9$ is, at each occurrence, independently selected from H and C$_1$-C$_6$-alkyl; and
p is 0, 1, 2, 3, or 4.

In an embodiment of the Compound of Formula III,
Y is —C(O)— or —SO$_2$—;
R$^1$ is C(O)R$^c$, C(O)NR$^d$R$^e$, —C(O)NR$^d$OR$^e$, or —C(O)NR$^d$N(R$^d$)$_2$;
R$^2$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^3$ is selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^4$ is selected from (CR$^8$R$^9$)$_p$—C$_1$-C$_9$-heteroaryl and (CR$^8$R$^9$)$_p$—C$_6$-C$_{12}$-aryl, wherein heteroaryl and aryl are optionally substituted with 1, 2, or 3 groups, each independently selected from —OH, halo, CN, C$_1$-C$_6$-alkyl, C$_1$-C$_6$-haloalkyl, —O—C$_1$-C$_6$-alkyl, and C$_1$-C$_6$-alkyl-OH.
R$^7$ is selected from H, C$_1$-C$_6$-alkyl, and C$_1$-C$_6$-alkyl-OH;
R$^8$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^9$ is, at each occurrence, independently selected from H and C$_1$-C$_6$-alkyl; and
p is 0, 1, 2, 3, or 4.

In an embodiment of the compound of Formula III, Y is —C(O)—.

In an embodiment of the compound of Formula III, R$^1$ is C(O)NR$^d$R$^e$, —C(O)NR$^d$OR$^e$, or —C(O)NR$^d$N(R$^d$)$_2$;
R$^d$ is selected from H, C$_1$-C$_6$-alkyl, and C$_1$-C$_6$-alkyl-OH;
R$^e$ is selected from H, C$_1$-C$_6$-alkyl, C$_1$-C$_6$-alkyl-OH, C$_1$-C$_6$-alkyl-OC$_1$-C$_6$-alkyl, C$_0$-C$_6$-alkyl-C$_3$-C$_8$-cycloalkyl, and C$_2$-C$_8$-heterocyclyl, wherein cycloalkyl and heterocyclyl are optionally substituted with 1 or 2 groups, each independently selected from —OH, halo, CN, C$_1$-C$_6$-alkyl, C$_1$-C$_6$-haloalkyl, and —O—C$_1$-C$_6$-alkyl; and
alternatively, R$^d$ and R$^e$ are optionally joined to form a heterocyclic ring, which is optionally substituted with 1 or 2 groups, each independently selected from —OH, halo, CN, C$_1$-C$_6$-alkyl, C$_1$-C$_6$-haloalkyl, and —O—C$_1$-C$_6$-alkyl.

In an embodiment of the compound of Formula III, R$^1$ is C(O)NR$^d$R$^e$, wherein R$^d$ is selected from H, C$_1$-C$_6$-alkyl, and C$_1$-C$_6$-alkyl-OH and R$^e$ is selected from H, C$_1$-C$_6$-alkyl, C$_1$-C$_6$-alkyl-OH, C$_3$-C$_8$-cycloalkyl, C$_2$-C$_8$-heterocyclyl, C$_6$-C$_{12}$-aryl, C$_1$-C$_9$-heteroaryl, and —O—C$_1$-C$_6$-alkyl alternatively wherein R$^d$ and R$^e$ optionally form a heterocyclic ring; or
R$^1$ is C(O)NR$^d$OR$^e$, wherein R$^d$ is selected from H, C$_1$-C$_6$-alkyl, and C$_1$-C$_6$-alkyl-OH and R$^e$ is selected from, C$_1$-C$_6$-alkyl-OC$_1$-C$_6$-alkyl, C$_0$-C$_6$-alkyl-C$_3$-C$_8$-cycloalkyl, C$_2$-C$_8$-heterocyclyl, C$_6$-C$_{12}$-aryl, and C$_1$-C$_9$-heteroaryl, wherein cycloalkyl, heterocyclyl, aryl, and heteroaryl are optionally substituted with 1, 2, or 3 groups, each independently selected from —OH, halo, CN, C$_1$-C$_6$-alkyl, C$_1$-C$_6$-haloalkyl, and —O—C$_1$-C$_6$-alkyl.

In an embodiment of the compound of Formula III, R$^d$ and R$^e$ are optionally joined to form a C$_3$-C$_5$ heterocyclic ring.

In another embodiment of the compound of Formula III, each R$^2$ is independently selected from H or C$_1$-C$_4$-alkyl. In a further embodiment of the compound of Formula III, R$^2$ is H.

In an embodiment of the compound of Formula III, R$^3$ is H.

In an embodiment of the compound of Formula III, R$^7$ is H or C$_1$-C$_4$-alkyl. In a further embodiment, R$^7$ is H or —CH$_3$. In yet another embodiment, R$^7$ is H.

In an embodiment of the compound of Formula III, R$^4$ is (CR$^8$R$^9$)$_p$—C$_1$-C$_5$-heteroaryl or (CR$^8$R$^9$)$_p$—C$_6$-aryl, or C$_3$-C$_8$-cycloalkyl, wherein heteroaryl, aryl and cycloalkyl are optionally substituted with 1, 2, or 3 groups, each independently selected from —OH, halo, CN, and C$_1$-C$_6$-alkyl;
R$^8$ is H or C$_1$-C$_6$-alkyl;
R$^9$ is H or C$_1$-C$_6$-alkyl; and
p is 0 or 1.

In an embodiment of the compound of Formula III, R$^4$ is (CR$^8$R$^9$)$_p$—C$_1$-C$_5$-heteroaryl or (CR$^8$R$^9$)$_p$—C$_6$-aryl, wherein heteroaryl and aryl are optionally substituted with 1, 2, or 3 groups, each independently selected from —OH, halo, CN, and C$_1$-C$_6$-alkyl;
R$^8$ is H or C$_1$-C$_6$-alkyl;
R$^9$ is H or C$_1$-C$_6$-alkyl; and
p is 0 or 1.

In a particular embodiment of the compound of Formula III, R$^4$ is

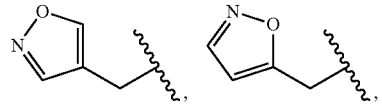

-continued
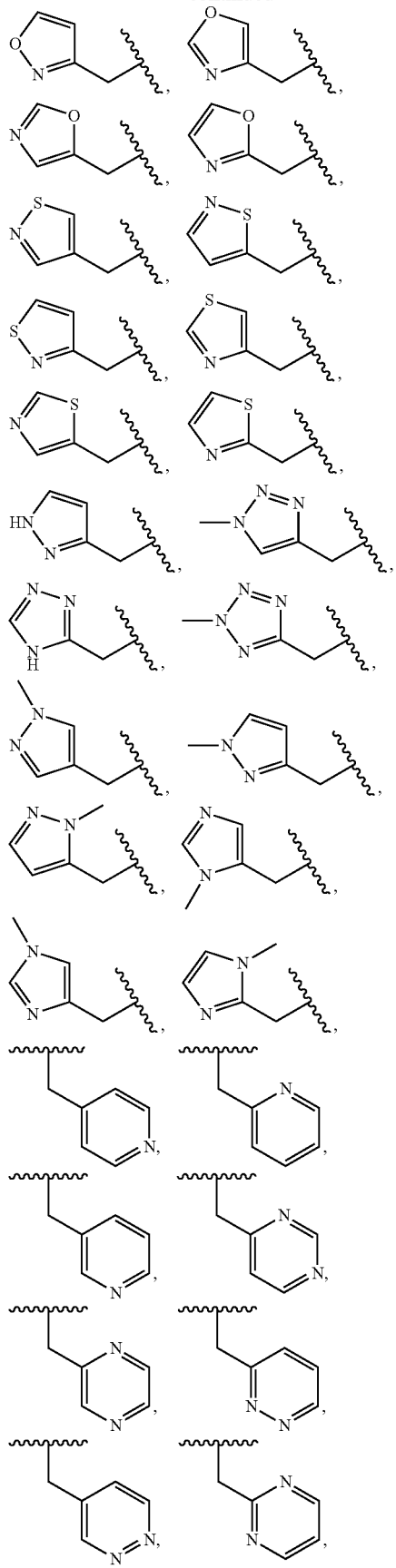
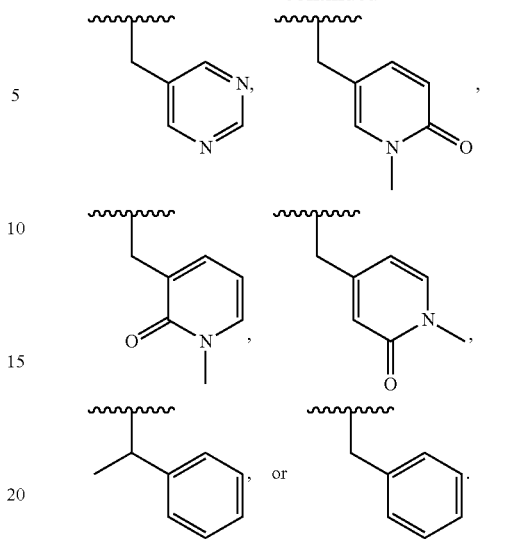
In another particular embodiment of the compound of Formula III, $R^4$ is
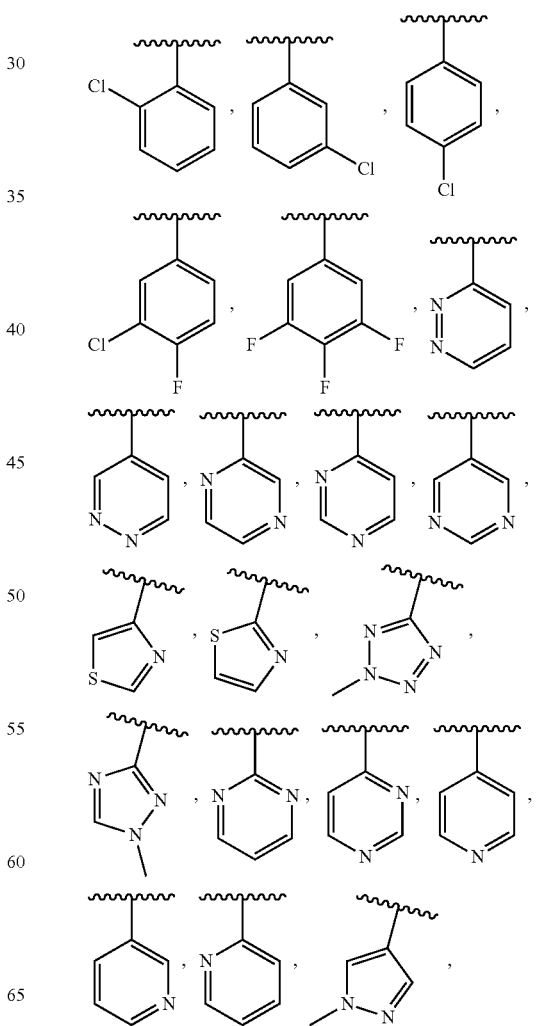

-continued
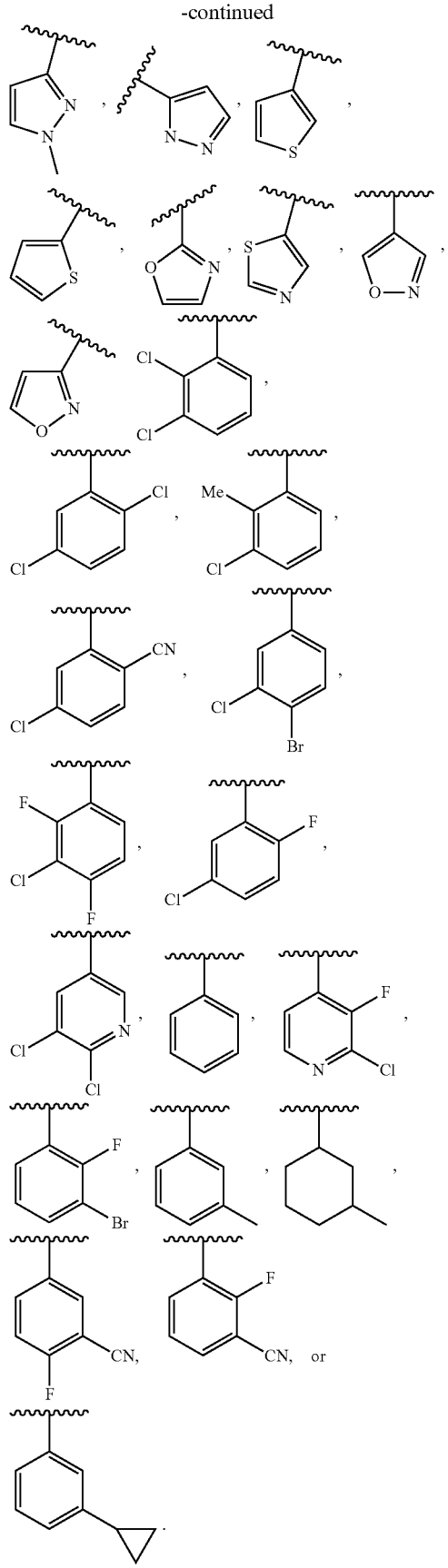
In another particular embodiment of the compound of Formula III, R⁴ is
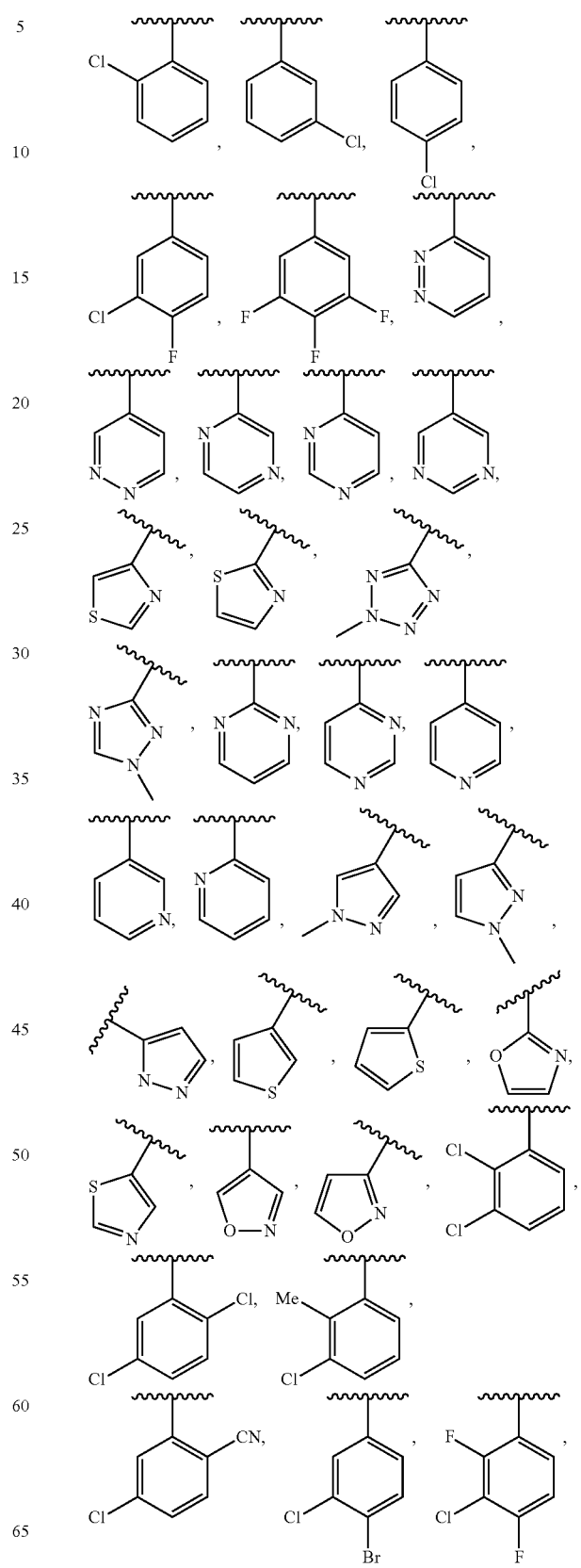

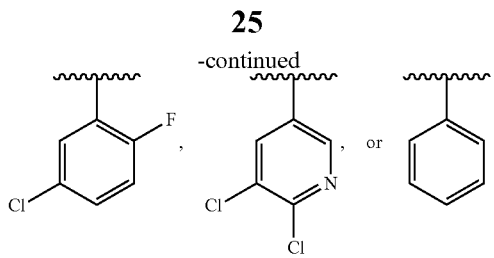

Also provided herein is a compound of Formula I, having the structure of Formula IV (also referred to as "a compound of Formula IV"):

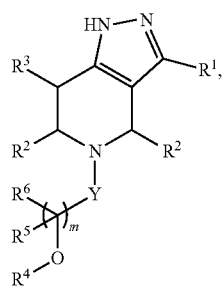

IV or a pharmaceutically acceptable salt thereof wherein,

Y is —C(O)— or —SO$_2$—; and m is 0, 1, or 2.

In an embodiment of the compound of Formula IV, Y is —C(O)—.

In an embodiment of the compound of Formula IV, R$^1$ is C(O)OR$^c$, C(O)R$^c$, C(O)NR$^d$R$^e$, —C(O)NR$^d$OR$^e$, or —C(O)NR$^d$N(R$^d$)$_2$.

In an embodiment of the compound of Formula IV, C(O)OR$^c$, C(O)R$^c$, or C(O)NR$^d$R$^e$, or —C(O)NR$^d$OR$^e$;

R$^c$ is C$_1$-C$_6$-alkyl; and

R$^d$ and R$^e$ are joined to form a heterocyclic ring.

In an embodiment of the compound of Formula IV, each R$^2$ is independently selected from H or C$_1$-C$_6$-alkyl. In a further embodiment of the compound of Formula IV, R$^2$ is H.

In an embodiment of the compound of Formula IV, R$^3$ is H.

In another embodiment of the compound of Formula IV, m is 1, R$^5$ is H or C$_1$-C$_6$-alkyl, R$^6$ is H or C$_1$-C$_6$-alkyl, and wherein R$^5$ and R$^4$ are optionally joined to form a ring. In another embodiment of the compound of Formula IV, m is 1; R$^5$ is C$_1$-C$_6$-alkyl; R$^6$ is H or C$_1$-C$_6$-alkyl; and R$^5$ and R$^4$ are optionally joined to form a ring. For example, in an embodiment,

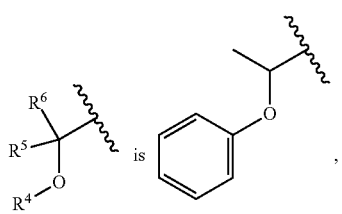

is

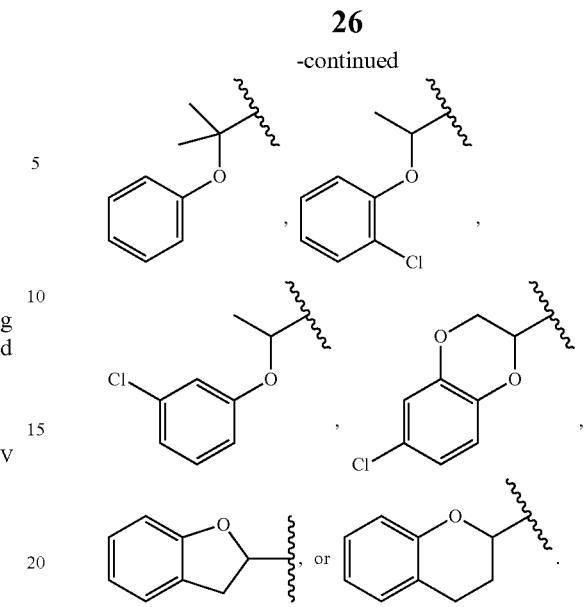

In another embodiment of the compound of Formula IV, R$^4$ is C$_1$-C$_6$-alkyl or (CR$^8$R$^9$)$_p$—C$_6$-C$_{12}$-aryl, wherein alkyl and aryl are optionally substituted with 1, 2, or 3, groups, each independently selected from —OH, halo, CN, C$_1$-C$_6$-alkyl, C$_1$-C$_6$-haloalkyl, —O—C$_1$-C$_6$-alkyl, C(O)N(R$^f$)$_2$, C(O)OR$^f$, —OCH$_2$C(O)OR$^f$, —SO$_2$R$^f$, and C$_1$-C$_6$-alkyl-OH.

In further embodiments of the compound of Formula IV, R$^4$ is

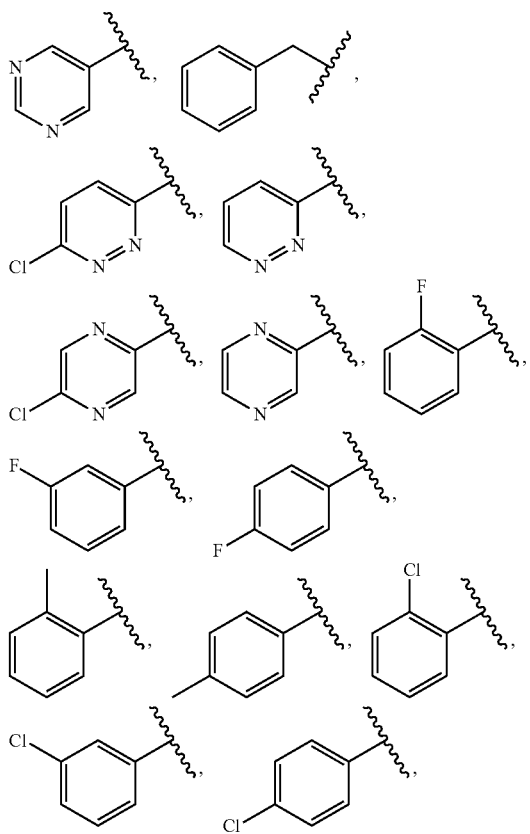

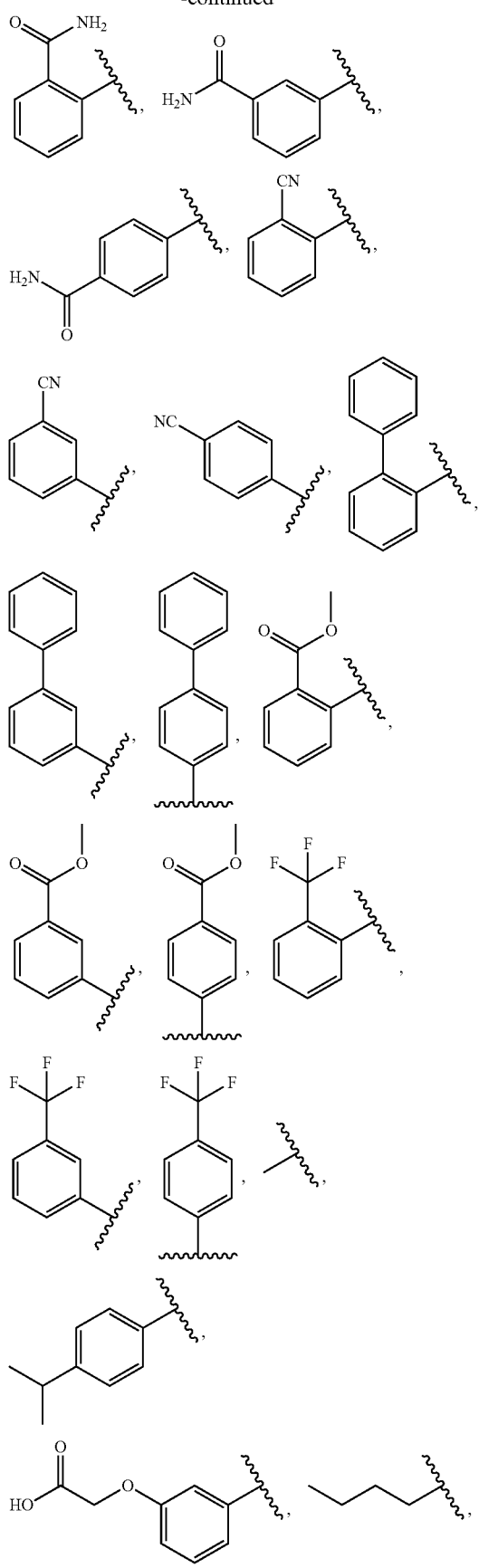
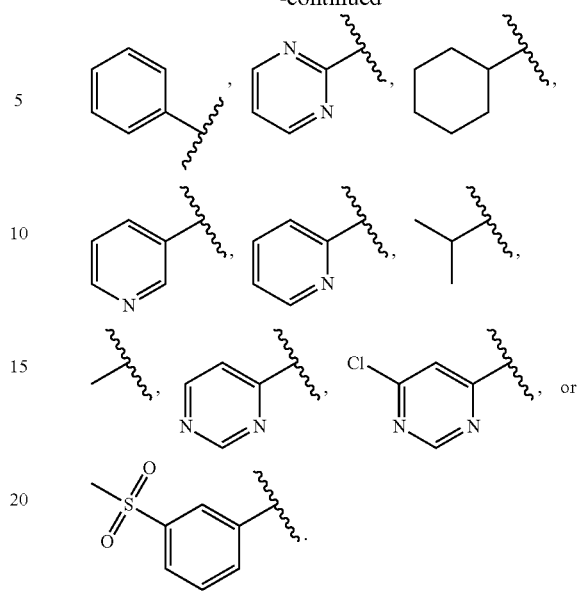
Certain embodiments of Formulas I-IV, including pharmaceutically acceptable salts thereof, are shown below in Table 1. All compounds of Formula I, II, III, and IV as well as pharmaceutically acceptable salts thereof, and the compounds of Table 1, as well as pharmaceutically acceptable salts thereof, are considered to be "compounds of the invention."
TABLE 1
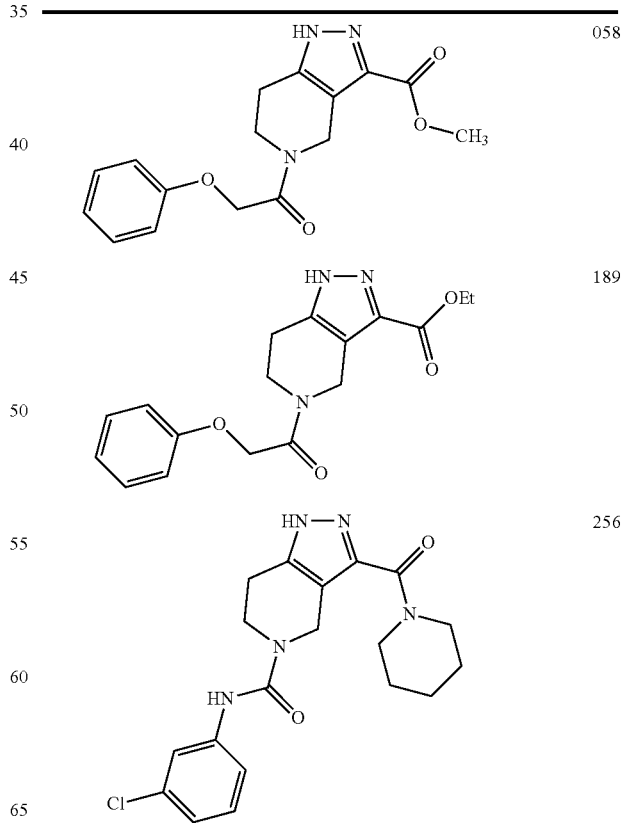

TABLE 1-continued
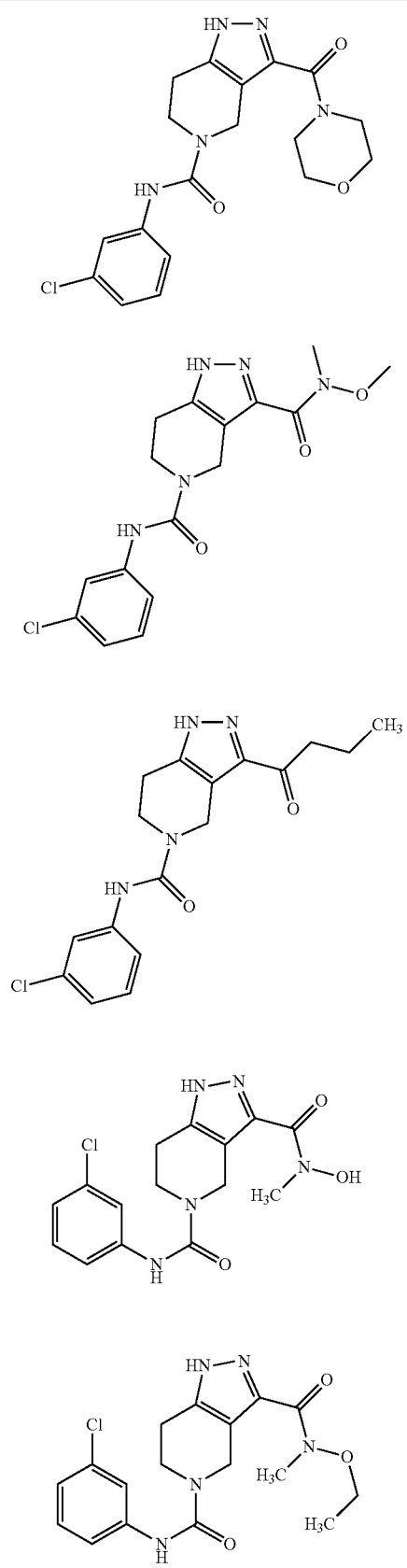
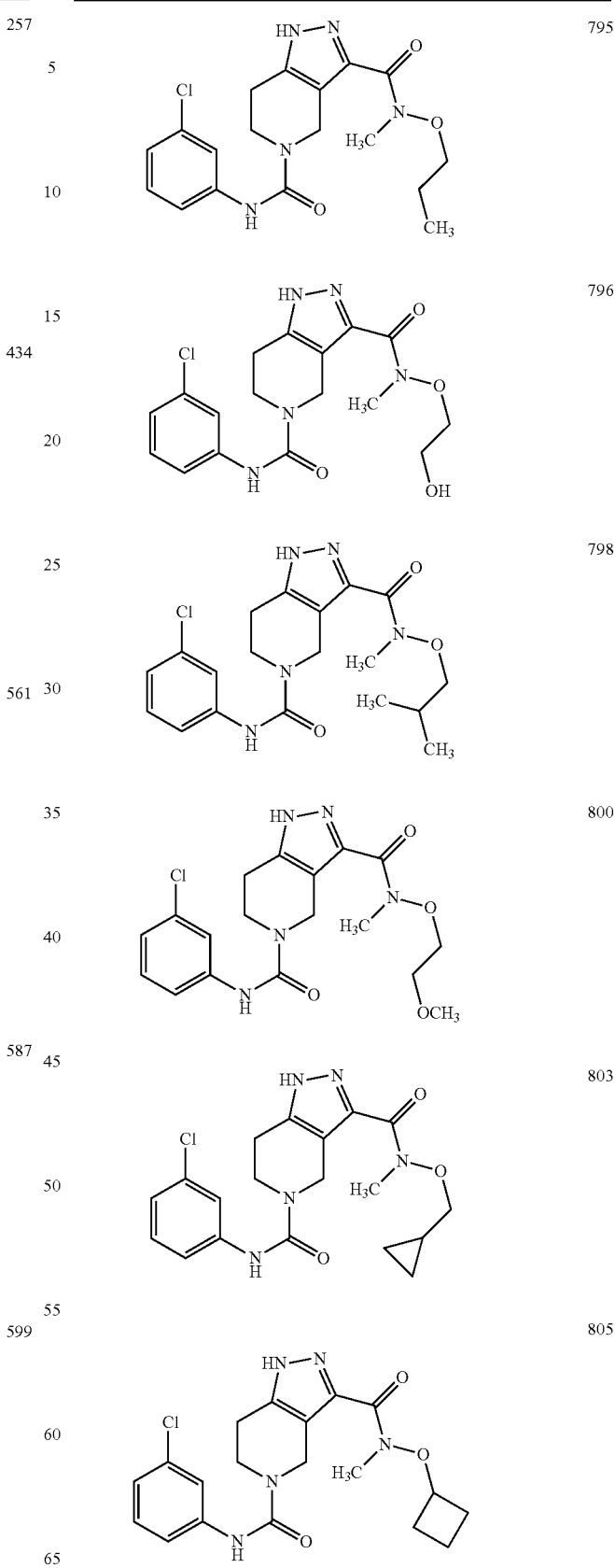

TABLE 1-continued
| | |
|---|---|
| 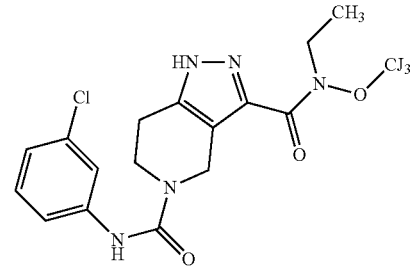 | 594 |
| 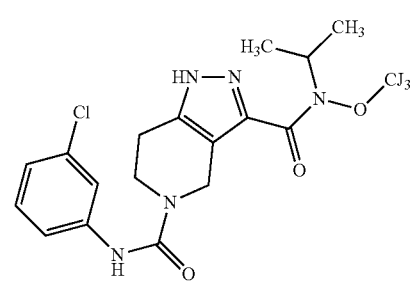 | 595 |
| 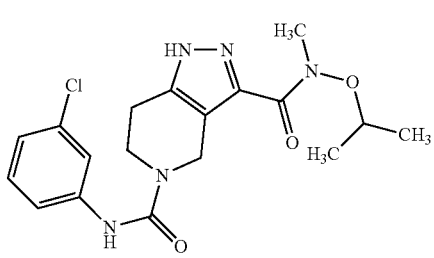 [SMILES: CC(C)ON(C)C(=O)c1n[nH]c2c1CN(C(=O)Nc1cccc(Cl)c1)CC2] | 600 |
| 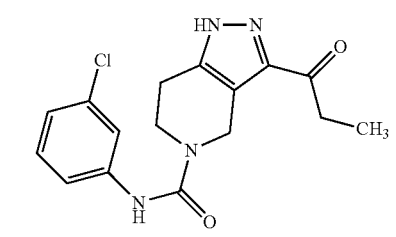 [SMILES: CCC(=O)c1n[nH]c2c1CN(C(=O)Nc1cccc(Cl)c1)CC2] | 695 |
| 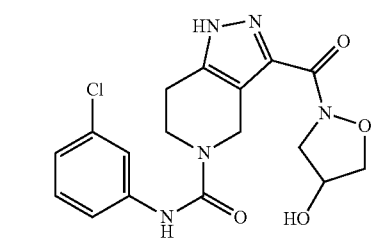 [SMILES: O=C(Nc1cccc(Cl)c1)N1CCc2[nH]nc(C(=O)N3CC(O)CO3)c2C1] | 697 |
| 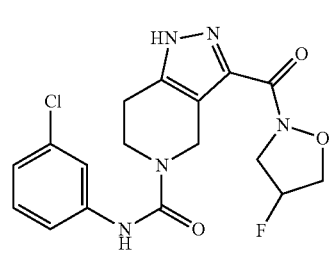 [SMILES: O=C(Nc1cccc(Cl)c1)N1CCc2[nH]nc(C(=O)N3CC(F)CO3)c2C1] | 698 |
TABLE 1-continued
| | |
|---|---|
| 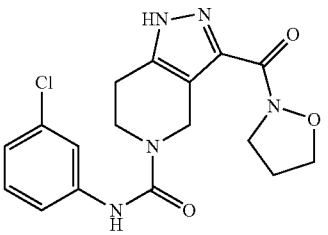 [SMILES: O=C(Nc1cccc(Cl)c1)N1CCc2[nH]nc(C(=O)N3CCCO3)c2C1] | 699 |
| 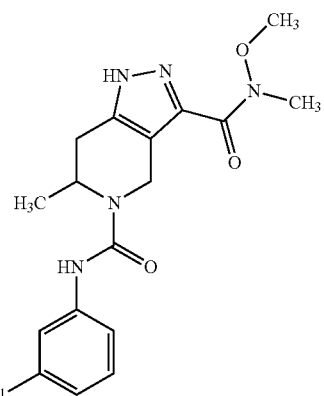 | 828 |
| 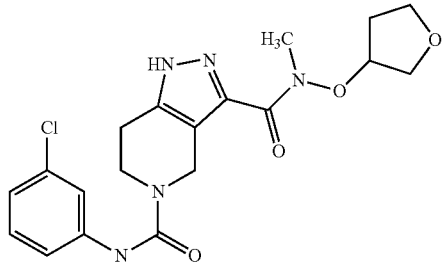 | 910 |
| 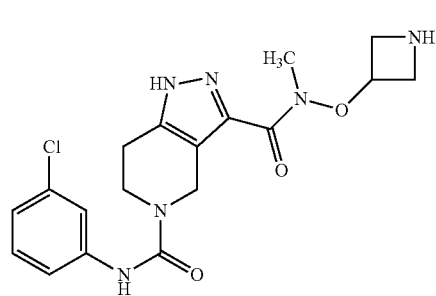 [SMILES: CN(OC1CNC1)C(=O)c1n[nH]c2c1CN(C(=O)Nc1cccc(Cl)c1)CC2] | 911 |
| 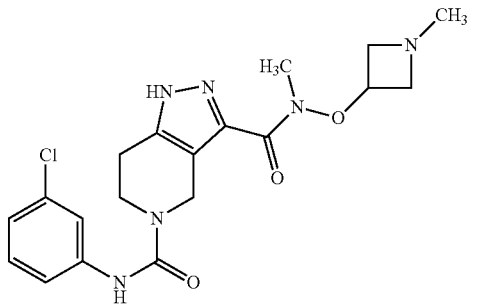 [SMILES: CN1CC(ON(C)C(=O)c2n[nH]c3c2CN(C(=O)Nc2cccc(Cl)c2)CC3)C1] | 912 |

TABLE 1-continued
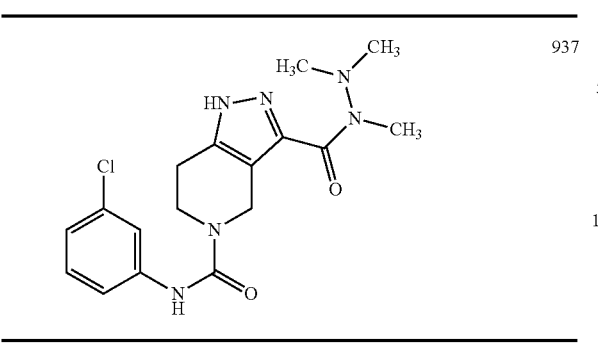
937
In yet another embodiment of Formula I provided herein, the compound of Formula III, or a pharmaceutically acceptable salt thereof, is selected from compounds shown in Table 2 and pharmaceutically acceptable salts thereof.
TABLE 2
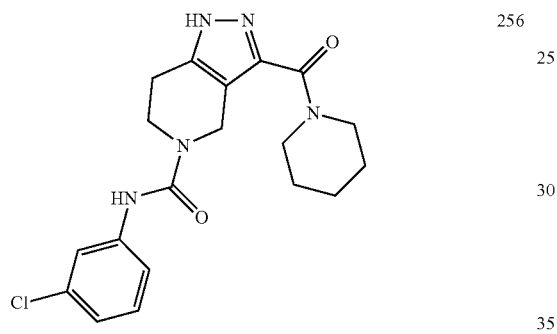
256
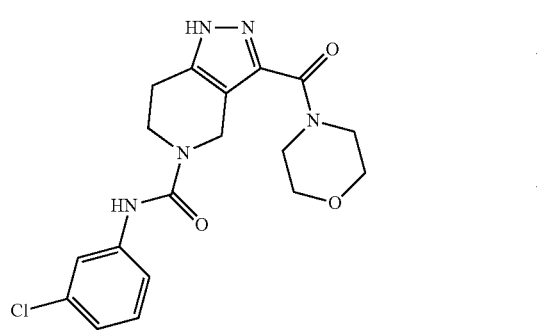
257
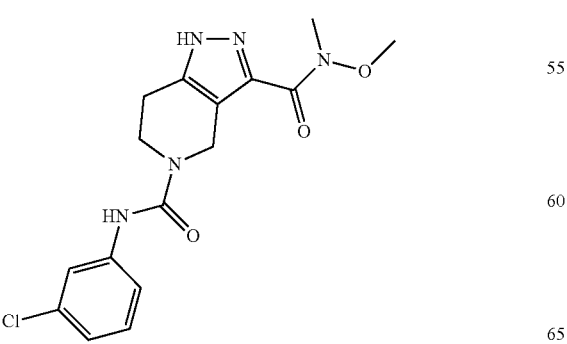
434
TABLE 2-continued
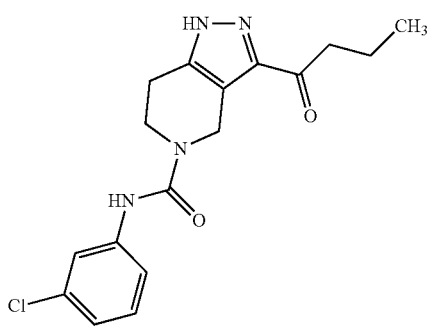 [SMILES: CCCC(=O)c1n[nH]c2c1CN(C(=O)Nc1cccc(Cl)c1)CC2]
561
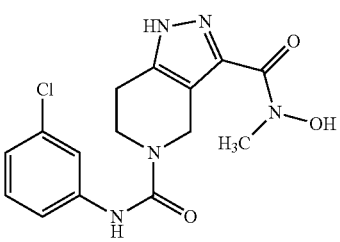 [SMILES: CN(O)C(=O)c1n[nH]c2c1CN(C(=O)Nc1cccc(Cl)c1)CC2]
587
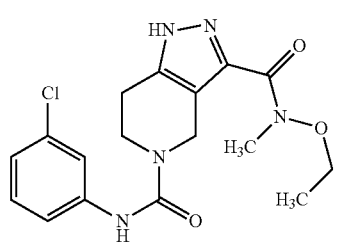 [SMILES: CCON(C)C(=O)c1n[nH]c2c1CN(C(=O)Nc1cccc(Cl)c1)CC2]
599
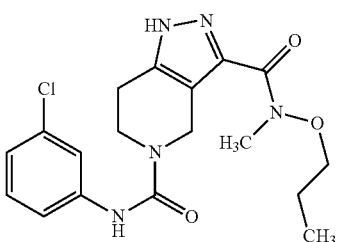
795
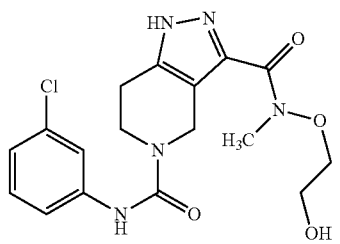
796
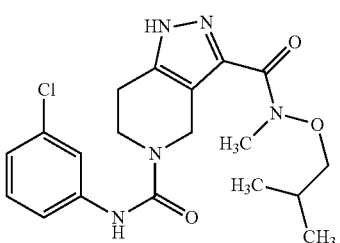
798

TABLE 2-continued
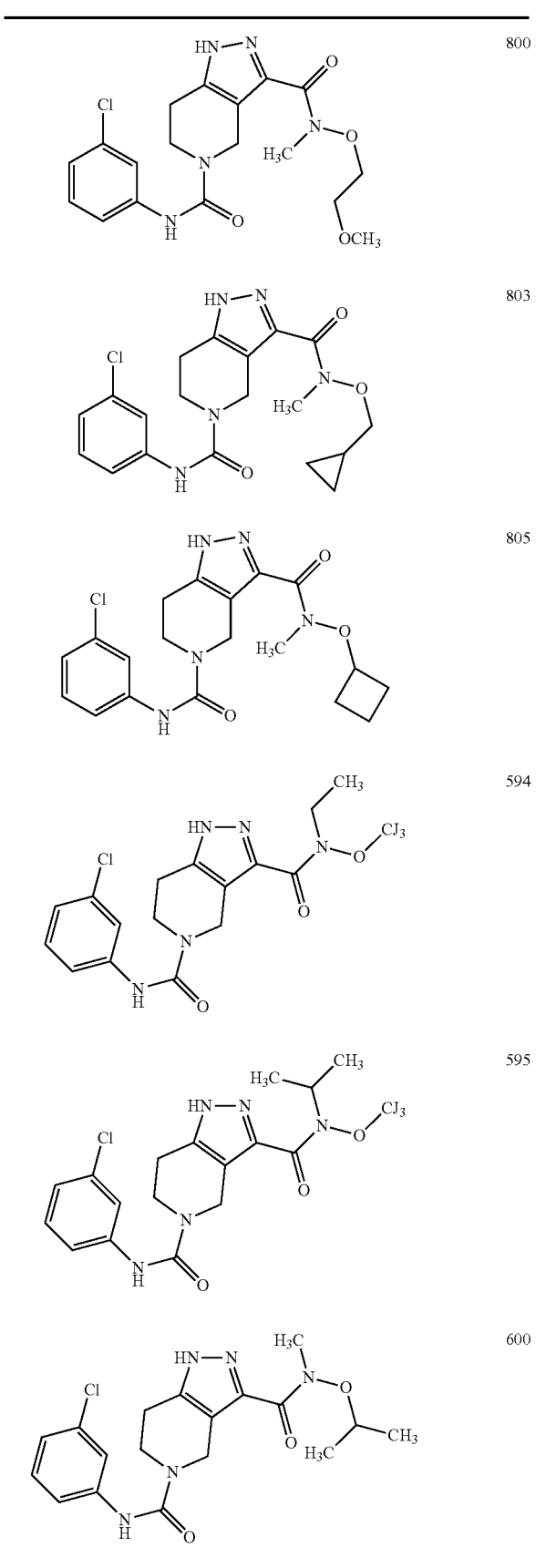
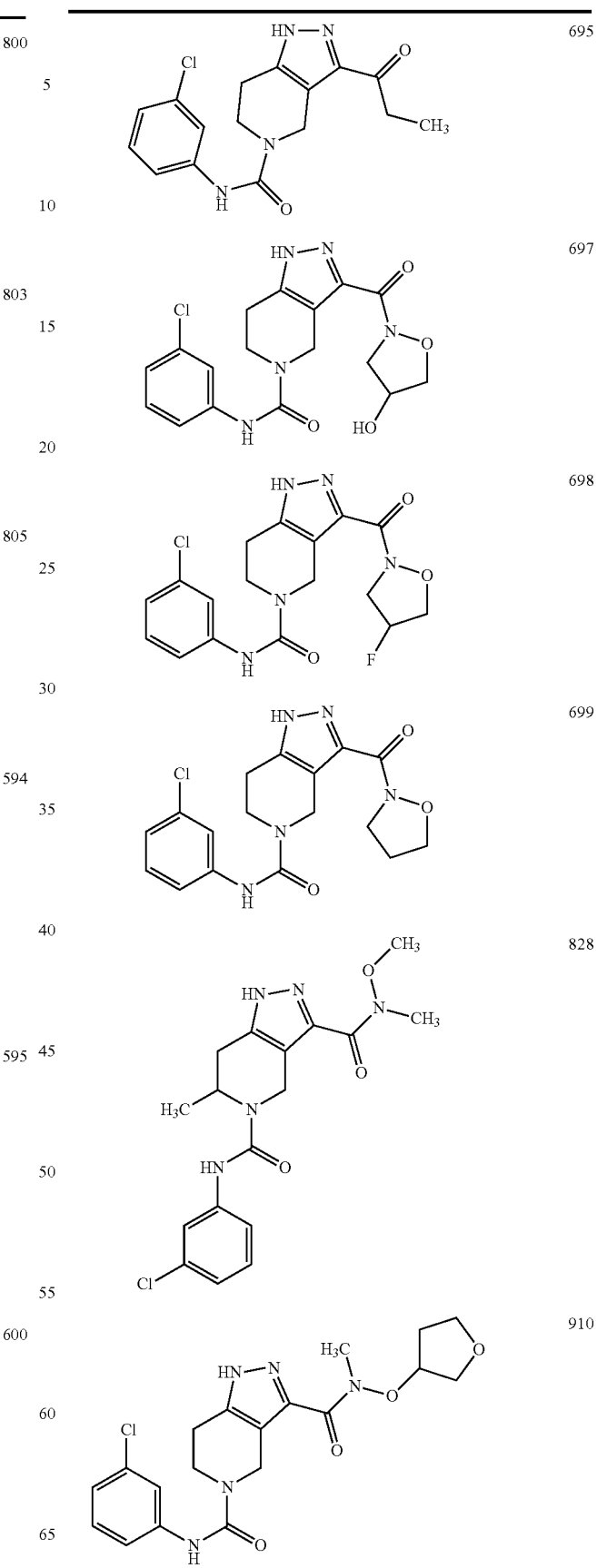

TABLE 2-continued

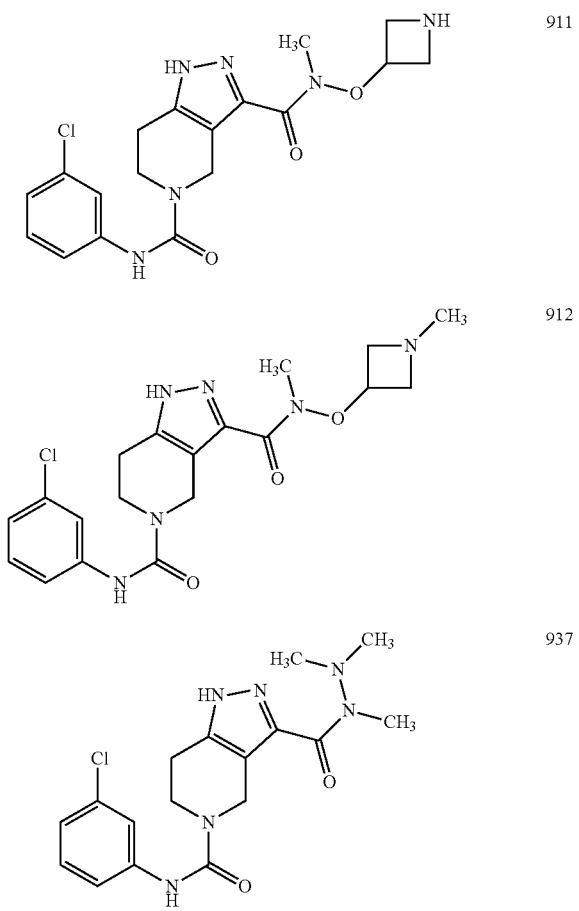

and pharmaceutically acceptable salts thereof

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

Methods of the Invention

The invention provides a method of treating an HBV infection in an individual in need thereof, comprising administering to the individual a therapeutically effective amount of a compound of the invention.

The invention also provides a method of eradicating an HBV infection in an individual in need thereof, comprising administering to the individual a therapeutically effective amount of a compound of the invention.

The invention also provides a method of reducing viral load associated with an HBV infection in an individual in need thereof, comprising administering to the individual a therapeutically effective amount of a compound of the invention.

The invention further provides a method of reducing reoccurrence of an HBV infection in an individual in need thereof, comprising administering to the individual a therapeutically effective amount of a compound of the invention.

The invention further provides a method of inhibiting or reducing the formation or presence of HBV DNA-containing particles or HBV RNA-containing particles in an individual in need thereof, comprising administering to the individual a therapeutically effective amount of a compound of the invention.

The invention also provides a method of reducing an adverse physiological impact of an HBV infection in an individual in need thereof, comprising administering to the individual a therapeutically effective amount of a compound of the invention.

The invention further provides a method of reducing, slowing, or inhibiting an HBV infection in an individual in need thereof, comprising administering to the individual a therapeutically effective amount of a compound of the invention.

The invention also provides a method of inducing remission of hepatic injury from an HBV infection in an individual in need thereof, comprising administering to the individual a therapeutically effective amount of a compound of the invention.

The invention further provides a method of reducing the physiological impact of long-term antiviral therapy for HBV infection in an individual in need thereof, comprising administering to the individual a therapeutically effective amount of a compound of the invention.

The invention further provides a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms. In another embodiment, the compound of the invention and the at least one additional therapeutic agent are co-formulated. In yet another embodiment, the compound of the invention and the at least one additional therapeutic agent are co-administered.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent or at a faster rate compared to the extent that other therapeutic classes of HBV drugs reduce viral load in the individual.

In one embodiment, the administering of a compound of the invention, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a compound of the invention, or a pharmaceutically acceptable salt thereof, reduces the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation and/or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eliminates or decreases the number of HBV RNA particles that are released from HBV infected cells thus enhancing, prolonging, or increasing the therapeutic benefit of the compounds of the invention.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

In another embodiment, the method of the invention further comprises monitoring the HBV viral load of the subject, and wherein the method is carried out for a period of time such that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Formula II, or a pharmaceutically acceptable salt thereof.

In another embodiment, provided herein is a method of treating an HBV infection in an individual in need thereof, comprising administering to the individual a therapeutically effective amount of a compound of Formula III, or a pharmaceutically acceptable salt thereof.

In another embodiment, provided herein is a method of treating an HBV infection in an individual in need thereof, comprising administering to the individual a therapeutically effective amount of a compound of Formula IV, or a pharmaceutically acceptable salt thereof.

In another embodiment, provided herein is a method of treating an HBV infection in an individual in need thereof, comprising administering to the individual a therapeutically effective amount of a compound of Table 1, or a pharmaceutically acceptable salt thereof.

In another embodiment, provided herein is a method of treating an HBV infection in an individual in need thereof, comprising administering to the individual a therapeutically effective amount of a compound of Table 2, or a pharmaceutically acceptable salt thereof.

In an embodiment of any of the methods provided herein, the method can further comprise monitoring the HBV viral load of the subject, wherein the method is carried out for a period of time such that the HBV virus is undetectable.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, reverse transcriptase inhibitor, immunomodulatory agents, a TLR-agonist, and other agents with distinct or unknown mechanisms that affect the HBV life cycle and/or affect the consequences of HBV infection.

In non-limiting examples, the compounds of the invention may be used in combination with one or more drugs (or a salt thereof) selected from the group consisting of HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon beta (IFN-β), interferon lambda (IFN-λ), and interferon gamma (IFN-γ);

viral entry inhibitors;

viral maturation inhibitors;

literature-described capsid assembly modulators, such as, but not limited to BAY 41-4109;

reverse transcriptase inhibitor;

an immunomodulatory agent such as a TLR-agonist; and agents of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferson alpha-2b.

Accordingly, in one embodiment, the compounds of Formula I, II, III, or IV, can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor and/or DNA and/or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In another aspect, provided herein is method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring the HBV viral load of the subject, wherein the method is carried out for a period of time such that the HBV virus is undetectable.

Administration/Dosage/Formulations

In another aspect, provided herein is pharmaceutical composition comprising a compound of the invention, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Procedure for the Preparation of Compounds 189 and 058

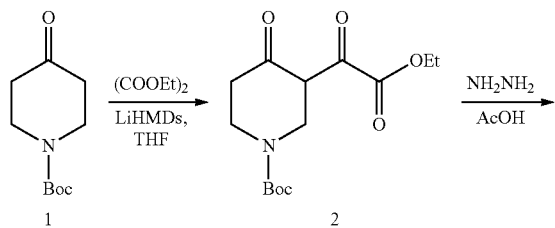

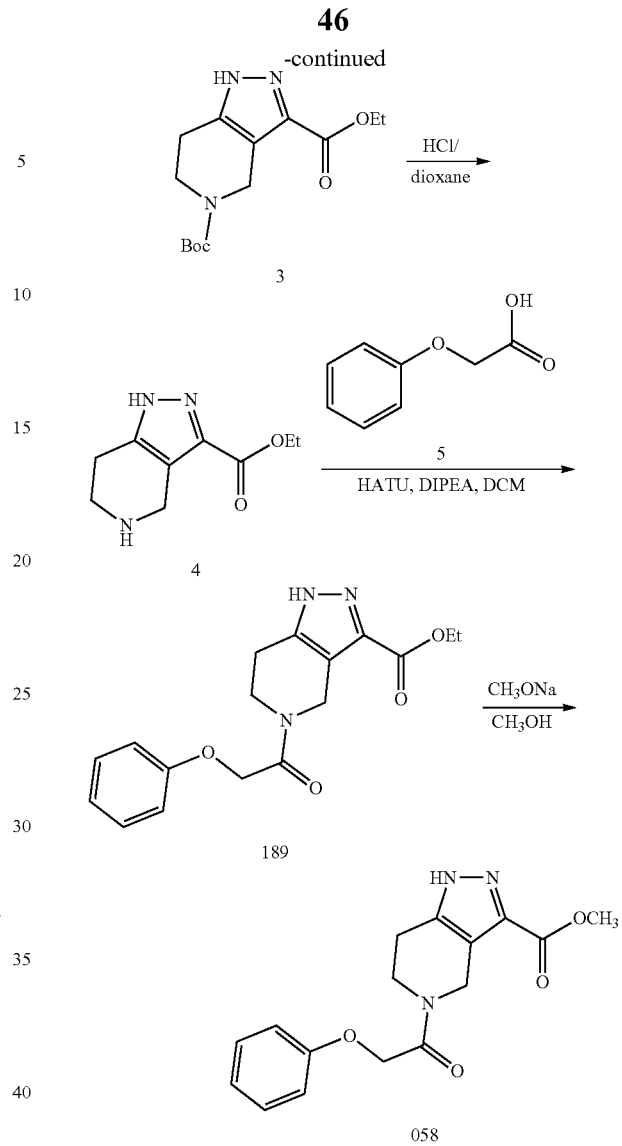

Step 1: Preparation of Compound 2

A three-necked round bottom flask was cooled to −78° C., LiHMDS (1 M, 13.05 mL, 1.30 eq) was added under $N_2$, then a solution of tert-butyl 4-oxopiperidine-1-carboxylate (2.00 g, 10.04 mmol, 1.00 eq) in THF (10.00 mL) was added dropwise, the reaction mixture was stirred at −78° C. for 30 minutes under $N_2$, to the mixture was added diethyl oxalate (1.91 g, 13.05 mmol, 1.30 eq) dropwise. After addition, the reaction mixture was warmed to 25° C. over a period of 30 minutes and stirred at 25° C. for another 7 hours. Several new peaks were shown on LCMS and 30% of desired compound was detected. The reaction was quenched with aqueous solution of $NH_4Cl$ (20 mL) and then neutralized by dilute hydrochloric acid, the aqueous layer was extracted with EA (20 mL*3), the combined organic phase was dried over anhydrous $Na_2SO_4$, filtered and concentrated in vacuum. Tert-butyl 3-(2-ethoxy-2-oxo-acetyl)-4-oxo-piperidine-1-carboxylate (1.77 g, 5.91 mmol, 58.90% yield) was obtained as yellow oil. The crude product was used into the next step directly without further purification. LCMS: 322 [M+23].

Step 2: Preparation of Compound 3

To a solution of tert-butyl 3-(2-ethoxy-2-oxo-acetyl)-4-oxo-piperidine-1-carboxylate (1.45 g, 4.84 mmol, 1.00 eq)

in AcOH (10.00 mL) was added NH₂NH₂—H₂O (370.56 mg, 6.29 mmol, 1.30 eq) dropwise, the reaction mixture was stirred at 80° C. for 5 hours. TLC (100% Ethyl acetate) showed starting material was consumed completely and one main peak with desired MS was detected by LCMS. When the reaction mixture was cooled to room temperature, the solvent was removed in vacuum. The residue was diluted with EA (50 mL) and washed with water (20 mL*2). The combined organic phase was dried over anhydrous Na₂SO₄, filtered and concentrated in vacuum. The residue was purified by silica gel chromatography (100-200 mesh silica gel, Petroleum ether/Ethyl acetate=5/1 to 0/1). 5-tert-butyl 3-ethyl 1,4,6,7-tetrahydropyrazolo[4,3-c]pyridine-3,5-dicarboxylate (780.00 mg, 2.64 mmol, 54.57% yield) was obtained as yellow oil. LCMS: 296 [M+1]

Step 3: Preparation of Compound 4

To a mixture of 5-tert-butyl 3-ethyl 1,4,6,7-tetrahydropyrazolo[4,3-c]pyridine-3,5-dicarboxylate (890.00 mg, 3.01 mmol, 1.00 eq) in dioxane (5.00 mL) was added HCl/dioxane (3.00 mL) in one portion. The reaction mixture was stirred at 20° C. for 2 hours, and a lot of solid was precipitate out. TLC (100% ethyl acetate) showed the reaction was completed. Evaporated the solution on a water bath under reduced pressure using a rotary evaporator. Ethyl 4,5,6,7-tetrahydro-1 H-pyrazolo[4,3-c]pyridine-3-carboxylate (580.00 mg, 2.97 mmol, 98.70% yield) was obtained as yellow solid. The crude product was used into next step directly without further purification.

Preparation of Compound 189

To a mixture of 2-phenoxyacetic acid (52.54 mg, 345.30 umol, 1.00 eq) and HATU (131.29 mg, 345.30 umol, 1.00 eq) in DCM (3.00 mL) was added DIPEA (66.94 mg, 517.96 umol, 1.50 eq) and ethyl 4,5,6,7-tetrahydro-1 H-pyrazolo[4,3-c]pyridine-3-carboxylate (80.00 mg, 345.30 umol, 1.00 eq) in one portion, the mixture was stirred at 20° C. for one hour. LCMS showed the desired compound was obtained. The mixture was extracted with DCM (10 mL*3) and water (10 mL), the organic phase was dried over anhydrous Na₂SO₄, filtered and concentrated in vacuum. Further purification by prep-HPLC (FA) to afford Compound 0189 (68.00 mg, 206.47 umol, 59.79% yield) as white solid. ¹H NMR (400 MHz, METHANOL-d₄) 7.25-7.30 (m, 2 H) 6.95-6.99 (m, 3 H) 4.86 (s, 2 H) 4.78 (br. s., 2 H) 4.31-4.38 (m, 2 H) 3.84-3.92 (m, 2 H) 2.79-2.89 (m, 2 H) 1.29-1.40 (m, 3 H). LCMS: 330 [M+1].

Preparation of Compound 058

To a solution of ethyl 5-(2-phenoxyacetyl)-1,4,6,7-tetrahydropyrazolo[4,3-c]pyridine-3-carboxylate (100.00 mg, 303.63 umol, 1.00 eq) in CH₃OH (3.00 mL) was added CH₃ONa (32.80 mg, 607.26 umol, 2.00 eq) under N₂, the reaction mixture was stirred at 20° C. for 16 hours. TLC (100% Ethyl acetate) showed starting material was consumed completely and one main peak with desired MS was detected by LCMS. The pH of the reaction mixture was adjusted to around 6 by adding diluted hydrochloride acid and extracted with EA (10 mL*4) and water (10 mL), the organic phase was dried over anhydrous Na₂SO₄, filtered and concentrated in vacuum. Further purification by prep-HPLC (FA) to afford Compound 058 (25.00 mg, 79.28 umol, 26.11% yield) as white solid. ¹H NMR (400 MHz, DMSO-d₄) 7.25-7.29 (m, 2 H) 6.90-6.95 (m, 3 H) 4.90-4.92 (m, 2 H) 4.62-4.64 (br. s., 2 H) 3.69-3.81 (m, 5 H) 2.66-2.83 (m, 2 H). LCMS: 316 [M+1].

Example 2

Procedure for the Preparation of Compound 256 and 257

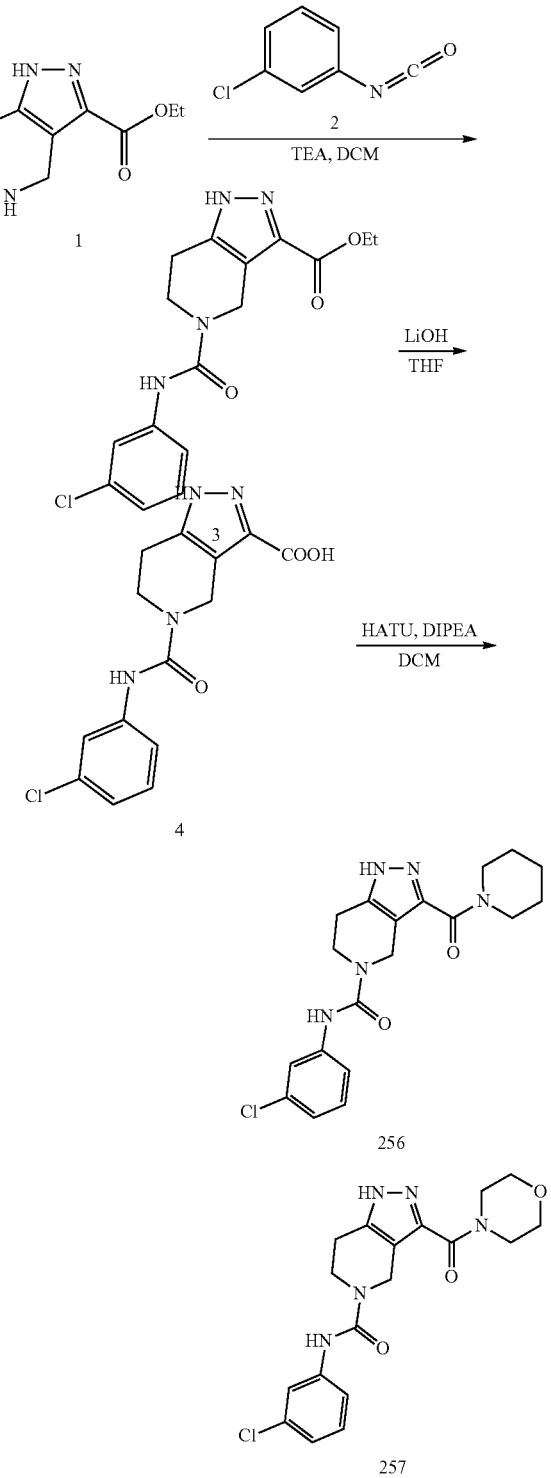

Step 1: Preparation of Compound 3

To a mixture of ethyl 4,5,6,7-tetrahydro-1H-pyrazolo[4,3-c]pyridine-3-carboxylate (1.00 g, 4.32 mmol, 1.00 eq, HCl) in DCM (10.00 mL) was added TEA (1.31 g, 12.95 mmol, 3.00 eq) at 0° C., followed by 1-chloro-3-isocyanato-benzene (662.85 mg, 4.32 mmol, 1.00 eq), the reaction mixture was stirred at 0° C. for 30 minutes. LCMS showed that 40% of desired product was detected. The mixture was extracted with DCM (15 mL*3) and water (15 mL), the organic phase was dried over anhydrous $Na_2SO_4$, filtered and concentrated in vacuum. The residue was purified by silica gel chromatography (100-200 mesh silica gel, Petroleum ether/Ethyl acetate=10/1, 1/1). Compound ethyl 5-[(3-chlorophenyl)carbamoyl]-1,4,6,7-tetrahydropyrazolo[4,3-c] pyridine-3-carboxylate (1.00 g, 2.87 mmol, 66.49% yield) was obtained as yellow solid. LCMS: 349 [M+1].

Step 2: Preparation of Compound 4

To a solution of ethyl 5-[(3-chlorophenyl)carbamoyl]-1, 4,6,7-tetrahydropyrazolo[4,3-c]pyridine-3-carboxylate (500.00 mg, 1.43 mmol, 1.00 eq) in THF (5.00 mL) was added a solution of LiOH (102.75 mg, 4.29 mmol, 3.00 eq) in $H_2O$ (1.00 mL), the reaction mixture was stirred at 30° C. for 16 hours. TLC (Petroleum ether:Ethyl acetate=0:1) showed the reaction was completed. The pH of the reaction mixture was adjusted to around 6 by adding diluted hydrochloride acid, then extracted with EA (20 mL*4), the organic phase was dried over anhydrous $Na_2SO_4$, filtered and concentrated in vacuum. 5-[(3-chlorophenyl)carbamoyl]-1,4,6,7-tetrahydropyrazolo[4,3-c]pyridine-3-carboxylic acid (400.00 mg, 1.18 mmol, 82.59% yield, 94.7% purity) was obtained as white solid. The crude product was used into next step directly without further purification. LCMS: 321 [M+1].

Preparation of Compound 256

To a mixture of 5-[(3-chlorophenyl)carbamoyl]-1,4,6,7-tetrahydropyrazolo[4,3-c]pyridine-3-carboxylic acid (50.00 mg, 155.89 umol, 1.00 eq) and HATU (59.28 mg, 155.89 umol, 1.00 eq) in DCM (5.00 mL) was added DIPEA (30.22 mg, 233.84 umol, 1.50 eq) and piperidine (13.27 mg, 109.13 umol, 0.70 eq, HCl) in one portion, the reaction mixture was stirred at 10° C. for 16 hours. Only 12% of desired compound was detected by LCMS. The mixture was extracted with DCM (15 mL*3) and water (15 mL). The organic phase was dried over anhydrous $Na_2SO_4$, filtered and concentrated in vacuum. Further purification by pre-HPLC (FA) to afford Compound 256 (10.00 mg, 25.60 umol, 16.42% yield, 99.3% purity) as white solid. $^1$H NMR (400 MHz, METHANOL-$d_4$) 7.51-7.52 (t, J=2.01 Hz, 1 H) 7.20-7.27 (m, 2 H) 6.99-7.01 (m, 1 H) 4.62 (s, 2 H) 3.69-3.88 (m, 6 H) 2.83-2.86 (t, J=5.71 Hz, 2 H) 1.63-1.72 (m, 6 H). LCMS: 388 [M+1].

Preparation of Compound 257

To a mixture of 5-[(3-chlorophenyl)carbamoyl]-1,4,6,7-tetrahydropyrazolo[4,3-c]pyridine-3-carboxylic acid (85.00 mg, 265.02 umol, 1.00 eq) and HATU (100.77 mg, 265.02 umol, 1.00 eq) in DCM (5.00 mL) was added DIPEA (51.38 mg, 397.53 umol, 1.50 eq) and morpholine (23.09 mg, 265.02 umol, 1.00 eq), the reaction mixture was stirred at 15° C. for 16 hours. The desired product was detected by LCMS. The mixture was extracted with DCM (10 mL*3) and water (10 mL), the organic phase was dried with anhydrous $Na_2SO_4$, filtered and concentrated in vacuum. Further purification by pre-HPLC (FA) to afford Compound 257 (20.00 mg, 51.05 umol, 19.26% yield, 99.5% purity) as white solid. $^1$H NMR (400 MHz, METHANOL-$d_4$) 7.51-7.52 (t, J=2.01 Hz, 1 H) 7.20-7.27 (m, 2 H) 6.99-7.01 (m, 1 H) 4.66 (s, 2 H) 4.09 (br. s., 2 H) 3.74-3.83 (m, 8 H) 2.82-2.85 (t, J=5.71 Hz, 2 H). LCMS: 390 [M+1].

Example 3

Preparation of Compound 434

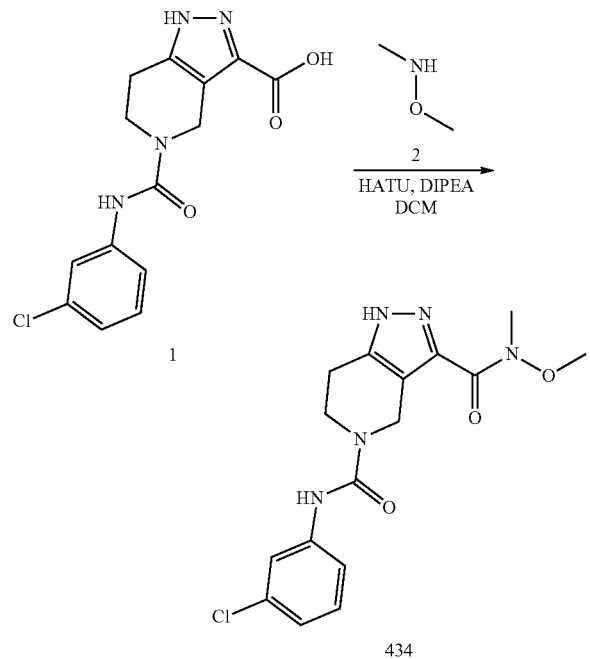

To a mixture of 5-[(3-chlorophenyl)carbamoyl]-1,4,6,7-tetrahydropyrazolo[4,3-c]pyridine-3-carboxylic acid (100.00 mg, 311.79 umol, 1.00 eq) in DCM (3.00 mL) was added HATU (118.55 mg, 311.79 umol, 1.00 eq) at 10° C., followed by DIPEA (60.44 mg, 467.69 umol, 1.50 eq) and N-methoxymethanamine (19.04 mg, 195.20 umol, 0.63 eq, HCl), the reaction mixture was stirred at 10° C. for 2 hours. LCMS showed compound 1 was consumed completely and one main peak with desired MS was detected. The mixture was extracted with DCM (10 mL*3) and water (10 mL), the organic phase was dried with anhydrous $Na_2SO_4$, filtered and concentrated in vacuum. Further purification by prep-HPLC (FA) to afford Compound 434 (30.00 mg, 82.13 umol, 26.34% yield, 99.6% purity) as white solid. $^1$H NMR (400 MHz, METHANOL-$d_4$) 7.51-7.52 (t, J=2.01 Hz, 1 H) 7.27-7.29 (m, 1 H) 7.20-7.24 (m, 1 H) 6.98-7.00 (m, 1 H) 4.71 (s, 2 H) 3.80-3.83 (t, J=5.77 Hz, 2 H) 3.75 (s, 3 H) 3.46 (br. s., 3 H) 2.83-2.86 (t, J=5.71 Hz, 2 H). LCMS: 364 [M+1].

Example 4

Preparation of Compound 561

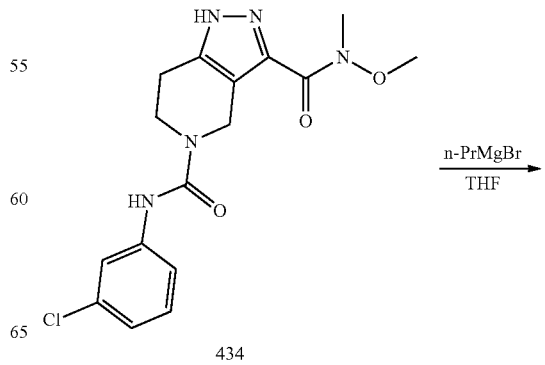

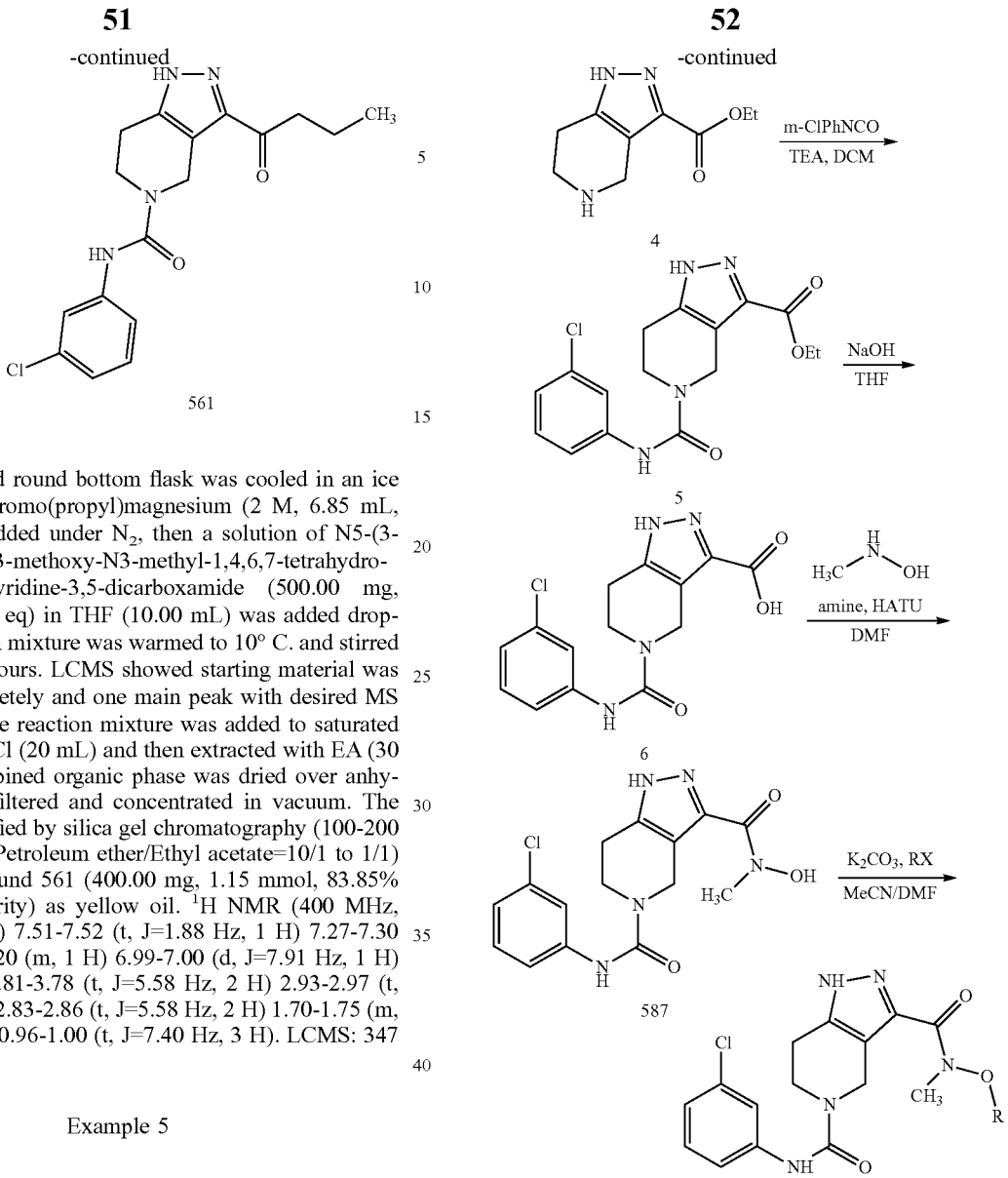

561

A three-necked round bottom flask was cooled in an ice bath to 0° C., bromo(propyl)magnesium (2 M, 6.85 mL, 10.00 eq) was added under $N_2$, then a solution of N5-(3-chlorophenyl)-N3-methoxy-N3-methyl-1,4,6,7-tetrahydro-pyrazolo[4,3-c]pyridine-3,5-dicarboxamide (500.00 mg, 1.37 mmol, 1.00 eq) in THF (10.00 mL) was added dropwise, the reaction mixture was warmed to 10° C. and stirred at 10° C. for 2 hours. LCMS showed starting material was consumed completely and one main peak with desired MS was detected. The reaction mixture was added to saturated aqueous of $NH_4Cl$ (20 mL) and then extracted with EA (30 mL*3), the combined organic phase was dried over anhydrous $Na_2SO_4$, filtered and concentrated in vacuum. The residue was purified by silica gel chromatography (100-200 mesh silica gel, Petroleum ether/Ethyl acetate=10/1 to 1/1) to afford Compound 561 (400.00 mg, 1.15 mmol, 83.85% yield, 99.6% purity) as yellow oil. $^1$H NMR (400 MHz, METHANOL-$d_4$) 7.51-7.52 (t, J=1.88 Hz, 1 H) 7.27-7.30 (m, 1 H) 7.24-7.20 (m, 1 H) 6.99-7.00 (d, J=7.91 Hz, 1 H) 4.743 (s, 2 H) 3.81-3.78 (t, J=5.58 Hz, 2 H) 2.93-2.97 (t, J=7.22 Hz, 2 H) 2.83-2.86 (t, J=5.58 Hz, 2 H) 1.70-1.75 (m, J=7.35 Hz, 2 H) 0.96-1.00 (t, J=7.40 Hz, 3 H). LCMS: 347 [M+1].

Example 5

Preparation of Compounds 587, 599, 795, 796, 798, 800, 803, and 805

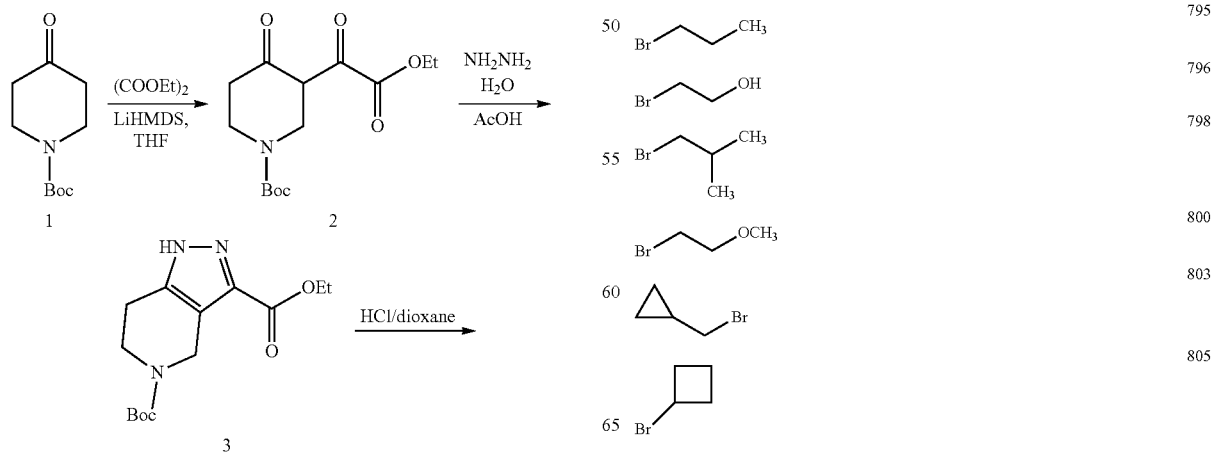

Step 1: Preparation of Compound 2

A three-necked round bottom flask was cooled to −78° C., LiHMDS (1 M, 652.44 mL, 1.30 eq) was added under $N_2$, then a solution of tert-butyl 4-oxopiperidine-1-carboxylate (100.00 g, 501.88 mmol, 1.00 eq) in THF (1.00 L) was added dropwise. The reaction mixture was stirred at −78° C. for 30 minutes under $N_2$. Diethyl oxalate (95.35 g, 652.44 mmol, 1.30 eq) was added dropwise. After addition, the reaction mixture was warmed to 15° C. over a period of 30 minutes and stirred at 15° C. for another 2 hours. TLC showed the reaction was completed. The reaction was quenched by aqueous solution of $NH_4Cl$ (1.5 L) and then neutralised by dilute hydrochloric acid. The aqueous layer was extracted with EA (800 mL*3), the combined organic phase was dried over anhydrous $Na_2SO_4$, filtered and concentrated in vacuum to give tert-butyl 3-(2-ethoxy-2-oxo-acetyl)-4-oxo-piperidine-1-carboxylate (165.00 g, crude) as a yellow oil and used directly for next step.

Step 2: Preparation of Compound 3

A mixture of tert-butyl 3-(2-ethoxy-2-oxo-acetyl)-4-oxo-piperidine-1-carboxylate (165.00 g, 551.25 mmol, 1.00 eq) and $NH_2NH_2 \cdot H_2O$ (35.71 g, 606.37 mmol, 1.10 eq) in AcOH (1.00 L) was degassed and purged with $N_2$ for 3 times, and then the mixture was stirred at 80° C. for 1 hour under $N_2$ atmosphere. TLC and LCMS showed the reaction was completed. The mixture was concentrated under reduced pressure to give a residue. The residue was dissolved in EA (800 mL) and washed with $Na_2CO_3$ (1 N, 1.2 L). The aqueous phase was extracted with ethyl acetate (800 mL*2). The combined organic phase was washed with brine (1 L*2), dried with anhydrous $Na_2SO_4$, filtered and concentrated in vacuum to give 5-tert-butyl 3-ethyl 1,4,6,7-tetrahydropyrazolo[4,3-c]pyridine-3,5-dicarboxylate (130.00 g, 440.19 mmol, 79.85% yield) as a yellow solid. LCMS: 296 [M+1]. $^1$H NMR (400 MHz, METHANOL-$d_4$) ppm δ 4.57-4.65 (m, 2H), 4.36 (d, J=7.03 Hz, 2H), 3.67-3.74 (m, 2H), 2.75 (t, J=5.65 Hz, 2H), 1.49 (s, 9H), 1.36-1.40 (m, 3H).

Step 3: Preparation of Compound 4

To a solution of 5-tert-butyl-3-ethyl-1,4,6,7-tetrahydropyrazolo[4,3-c]pyridine-3,5-dicarboxylate (50.00 g, 169.30 mmol, 1.00 eq) in dioxane (200.00 mL) was added HCl/dioxane (4 M, 300.00 mL, 7.09 eq) at 15° C. The reaction mixture was stirred at 15° C. for one hour, and the solid was precipitated out. TLC showed the reaction was complete. The solution was evaporated on a water bath under reduced pressure using a rotary evaporator to afford ethyl 4,5,6,7-tetrahydro-1H-pyrazolo[4,3-c]pyridine-3-carboxylate (37.00 g, 159.70 mmol, 94.33% yield, HCl) as a yellow solid.

Step 4: Preparation of Compound 5

To a mixture of ethyl-4,5,6,7-tetrahydro-1H-pyrazolo[4,3-c]pyridine-3-carboxylate (37.00 g, 159.70 mmol, 1.00 eq, HCl) in DCM (300.00 mL) was added TEA (48.48 g, 479.11 mmol, 3.00 eq) at −10° C., 1-chloro-3-isocyanato-benzene (19.62 g, 127.76 mmol, 0.80 eq) was added dropwise during 30 minutes. The reaction mixture was stirred at −10° C. for another 30 minutes. TLC indicated ~5% of compound 4 was remained, and one major new spot with lower polarity was detected. The mixture was extracted with DCM (800 mL*3) and water (300 mL*2), the organic phase was dried with anhydrous $Na_2SO_4$, filtered and concentrated in vacuum to afford ethyl 5-[(3-chlorophenyl)carbamoyl]-1,4,6,7-tetrahydropyrazolo[4,3-c]pyridine-3-carboxylate (52.00 g, crude) as yellow solid. The crude product was used in the next step directly without further purification.

Step 5: Preparation of Compound 6

To a solution of ethyl 5-[(3-chlorophenyl)carbamoyl]-1,4,6,7-tetrahydropyrazolo[4,3-c]pyridine-3-carboxylate (30.00 g, 86.01 mmol, 1.00 eq) in THF (300.00 mL) was added a solution of NaOH (6.88 g, 172.02 mmol, 2.00 eq) in $H_2O$ (60.00 mL), the reaction mixture was warmed to 40° C. and stirred at 40° C. for 16 hours. TLC showed the reaction was complete. The pH of the reaction mixture was adjusted to around 5 by adding diluted hydrochloride acid (1 N), then extracted with EA (500 mL*4) and water (300 mL). The organic phase was dried over anhydrous $Na_2SO_4$, filtered and concentrated in vacuum to afford 5-[(3-chlorophenyl)carbamoyl]-1,4,6,7-tetrahydropyrazolo[4,3-c]pyridine-3-carboxylic acid (23.00 g, crude) as light yellow solid. LCMS: 321/323 [M+1]. $^1$H NMR (400 MHz, METHANOL-$d_4$) ppm δ 11.48 (t, J=1.94 Hz, 1 H) 11.23-11.28 (m, 1 H) 11.14-11.21 (m, 1 H) 10.92-10.98 (m, 1 H) 8.71 (s, 2 H) 7.78 (t, J=5.71 Hz, 2 H) 6.80 (t, J=5.65 Hz, 2 H).

Preparation of Compound 587

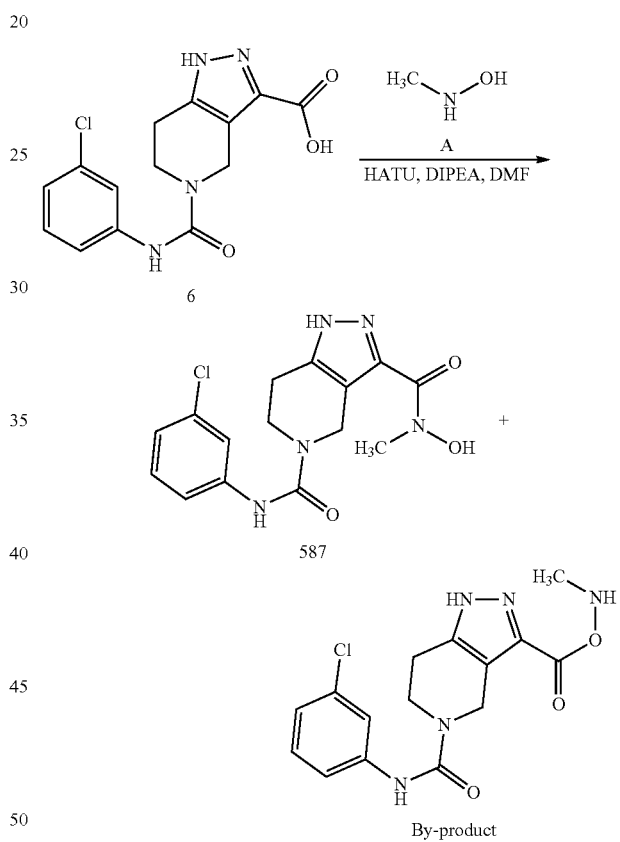

A mixture of 5-[(3-chlorophenyl)carbamoyl]-1,4,6,7-tetrahydropyrazolo[4,3-c]pyridine-3-carboxylic acid (50.00 mg, 155.89 umol, 1.00 eq), N-methylhydroxylamine (13.02 mg, 155.89 umol, 1.00 eq, HCl), DIPEA (50.37 mg, 389.72 umol, 2.50 eq), and HATU (59.27 mg, 155.89 umol, 1.00 eq) in DMF (2.00 mL) was degassed and purged with $N_2$ for 3 times, and then the mixture was stirred at 15° C. for 16 hours under $N_2$ atmosphere. LCMS showed the reaction was completed. The mixture was poured into water (10 mL) and stirred at 5 min. The aqueous phase was extracted with DCM (5 mL*3). The combined organic phase was washed with brine (10 mL*2), dried with anhydrous $Na_2SO_4$, filtered and concentrated in vacuum. The residue was purified by prep-HPLC (FA) to give N5-(3-chlorophenyl)-N3-hydroxy-N3-methyl-6,7-dihydro-1H-pyrazolo[4,3-c]pyridine-3,5(4H)- dicarboxamide (15.00 mg, 41.60 umol, 26.68% yield, 97% purity) as white solid and by-product (12.00 mg). LCMS: 350/351 [M+1]. $^1$H NMR (400 MHz, METHANOL-$d_4$) ppm δ 7.50-7.55 (m, 1H), 7.28 (s, 1H), 7.24 (d, J=7.91 Hz, 1H), 7.01 (s, 1H), 4.71-4.78 (m, 2H), 3.82 (s, 2H), 3.33-3.58 (m, 3H), 2.85 (s, 2H).

Preparation of Compound iiii (Compounds 599, 795, 796, 798, 800, 803, and 805)

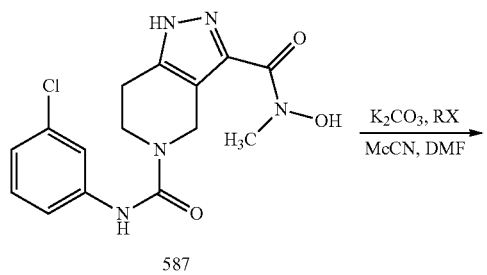

General Procedure: A mixture of N5-(3-chlorophenyl)-N3-hydroxy-N3-methyl-1,4,6,7-tetrahydropyrazolo[4,3-c]pyridine-3,5-dicarboxamide (1.00 eq.), RX (1.50 eq.), $K_2CO_3$ (1.50 eq.) in MeCN or DMF (2.00 mL) was stirred at 25° C. for 20 hours. LCMS showed reaction completed. The reaction mixture was filtered and diluted with MeOH (1 mL). The residue was purified by prep-HPLC (FA) to afford the desired product.

| Comp. ID | Analytical Data |
|---|---|
| 599 | LCMS (M + 1): 378/380 |
| | $^1$H NMR (400 MHz, CHLOROFORM-d) ppm δ 7.54 (s, 1H), 7.16-7.26 (m, 2H), 7.01 (d, J = 7.65 Hz, 1H), 6.67 (s, 1H), 4.77 (s, 2H), 4.06 (q, J = 7.07 Hz, 2H), 3.88 (t, J = 5.71 Hz, 2H), 3.43 (s, 3H), 2.89 (t, J = 5.71 Hz, 2H), 1.35 (t, J = 7.09 Hz, 3H). |
| 795 | LCMS (M + 1): 392/394 |
| 796 | LCMS (M + 1): 394/396 |
| 798 | LCMS (M + 1): 406/408 |
| | $^1$H NMR (400 MHz, MeOD-$d_4$) ppm δ 7.51 (s, 1 H) 7.30-7.21 (m, 2 H) 7.00 (d, J = 8.00 Hz, 1 H) 4.70 (d, J = 12.00 Hz, 2 H) 3.82 (s, 2 H) 3.72-3.39 (m, 5 H) 2.85 (t, J = 4.00 Hz, 2 H) 1.89 (s, 1 H) 0.91 (d, J = 4.00 Hz, 6 H) |
| 800 | LCMS (M + 1): 408/410 |
| 803 | LCMS (M + 1): 404/406 |
| 805 | LCMS (M + 1): 404/406 |

Example 6

Preparation of Compounds 594, 595, 600

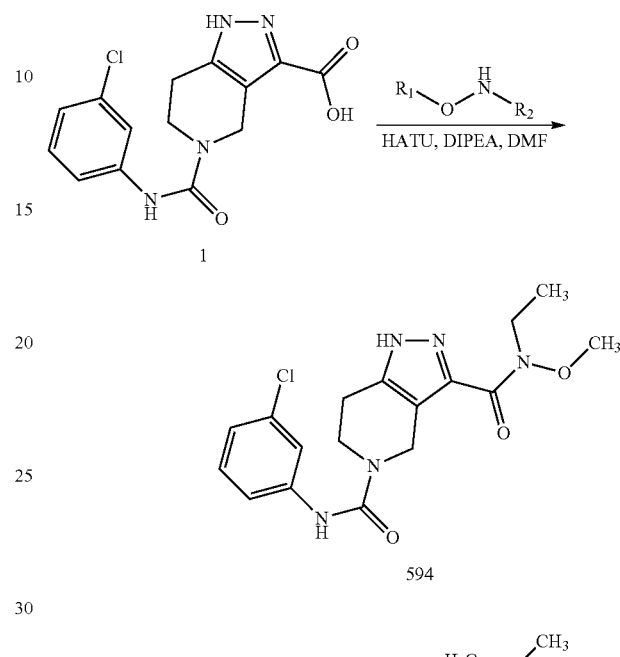

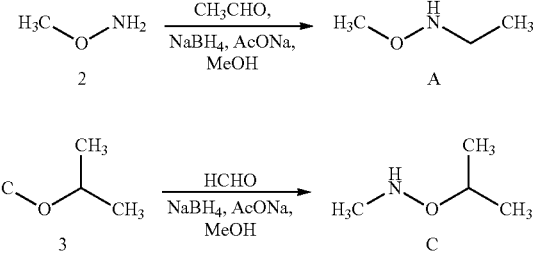

Step 1: Preparation of Compound A

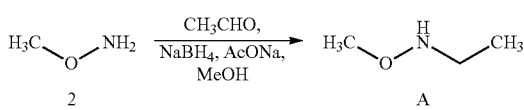

A mixture of O-methylhydroxylamine (1.00 g, 11.97 mmol, 1.00 eq, HCl salt), AcONa (981.94 mg, 11.97 mmol, 1.00 eq) in MeOH (10.00 mL) was added acetaldehyde (3.96 g, 35.92 mmol, 3.00 eq) under $N_2$, and then the mixture was stirred at 15° C. for 2 hr under $N_2$ atmosphere. NaBH$_4$ (1.36 g, 35.92 mmol, 3.00 eq) was added at 0° C. The resulting mixture was stirred at 15° C. for 14 hr under $N_2$ atmosphere. TLC showed the reaction was completed. The mixture was poured into ice-water (20 mL) and stirred for 5 min. The aqueous phase was extracted with DCM (10 mL*3). The combined organic phase was washed with brine (20 mL*2), dried with anhydrous Na$_2$SO$_4$, filtered and then HCl/EA (50 mL) was added, the mixture was concentrated in vacuum to give N-methoxyethanamine (264.00 mg, 2.37 mmol, 19.77% yield, HCl) as a white oil. $^1$H NMR (400 MHz, METHANOL-d$_4$) ppm δ 3.94 (s, 3H), 3.35 (q, J=7.28 Hz, 2H), 1.32 (t, J=7.28 Hz, 3H).

Preparation of Compound 594

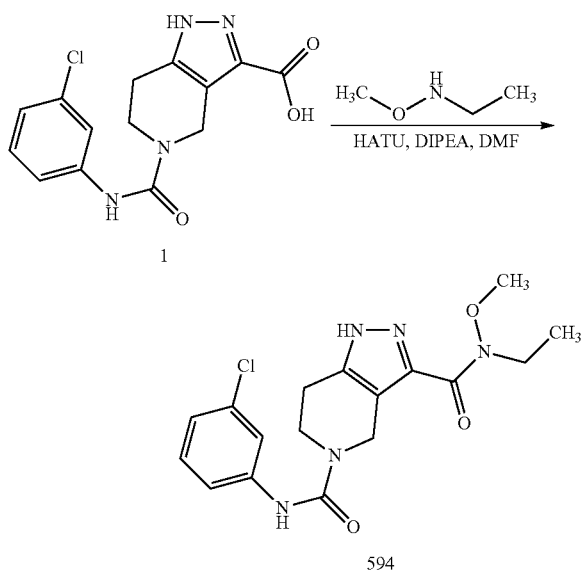

A mixture of 5-[(3-chlorophenyl)carbamoyl]-1,4,6,7-tetrahydropyrazolo [4,3-c]pyridine-3-carboxylic acid (50.00 mg, 155.89 umol, 1.00 eq), N-methoxyethanamine (14.05 mg, 125.93 umol, 0.81 eq, HCl), HATU (59.28 mg, 155.89 umol, 1.00 eq), and DIPEA (50.37 mg, 389.74 umol, 2.50 eq) in DMF (2.00 mL) was degassed and purged with $N_2$ for 3 times, and then the mixture was stirred at 15° C. for 16 hours under $N_2$ atmosphere. LCMS showed the reaction was completed. The mixture was poured into water (5 mL) and stirred at 5 min. The aqueous phase was extracted with ethyl acetate (3 mL*3). The combined organic phase was washed with brine (5 mL*2), dried with anhydrous Na$_2$SO$_4$, filtered and concentrated in vacuum. The residue was purified by prep-HPLC (FA) to give N5-(3-chlorophenyl)-N3-ethyl-N3-methoxy-1,4,6,7-tetrahydropyrazolo[4,3-c]pyridine-3,5-dicarboxamide (15.00 mg, 39.11 umol, 25.09% yield, 98.5% purity) as a white solid. LCMS: 378/380 [M+1]. $^1$H NMR (400 MHz, METHANOL-d$_4$) ppm δ 7.50-7.53 (m, 1H), 7.27-7.32 (m, 1H), 7.20-7.25 (m, 1H), 6.97-7.02 (m, 1H), 4.71 (br. s., 2H), 3.82 (t, J=5.77 Hz, 2H), 3.76 (s, 3H), 3.31-3.32 (m, 2H), 2.85 (s, 2H), 1.29 (t, J=7.03 Hz, 3H).

Preparation of Compound 595

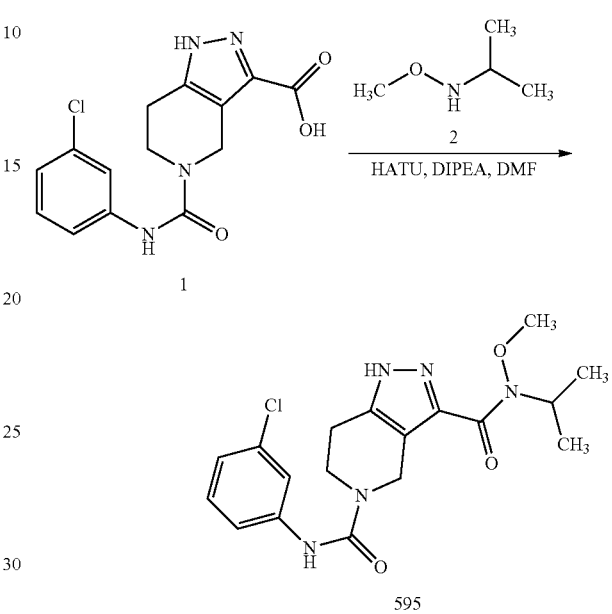

A mixture of 5-[(3-chlorophenyl)carbamoyl]-1,4,6,7-tetrahydropyrazolo [4,3-c]pyridine-3-carboxylic acid (50.00 mg, 155.89 umol, 1.00 eq), N-methoxypropan-2-amine (23.50 mg, 187.07 umol, 1.20 eq, HCl), DIPEA (50.37 mg, 389.72 umol, 2.50 eq), HATU (59.27 mg, 155.89 umol, 1.00 eq) in DMF (2.00 mL) was degassed and purged with $N_2$ for 3 times, and then the mixture was stirred at 15° C. for 16 hours under $N_2$ atmosphere. LCMS showed the reaction was completed. The mixture was poured into water (5 mL) and stirred at 5 min. The aqueous phase was extracted with ethyl acetate (3 mL*3). The combined organic phase was washed with brine (5 mL*2), dried with anhydrous Na$_2$SO$_4$, filtered and concentrated in vacuum. The residue was purified by prep-HPLC (FA) to give N5-(3-chlorophenyl)-N3-isopropyl-N3-methoxy-1,4,6,7-tetrahydropyrazolo[4,3-c]pyridine-3,5-dicarboxamide (10.00 mg, 25.44 umol, 16.32% yield, 99.7% purity) as a white solid. LCMS: 392/394 [M+1]. $^1$H NMR (400 MHz, METHANOL-d$_4$) ppm δ 7.52 (t, J=1.94 Hz, 1H), 7.26-7.32 (m, 1H), 7.19-7.26 (m, 1H), 7.00 (d, J=8.53 Hz, 1H), 4.70 (br. s., 2H), 3.73-3.88 (m, 5H), 3.32 (br. s., 1H), 2.85 (t, J=5.65 Hz, 2H), 1.32 (br. s., 6H).

Preparation of Compound C

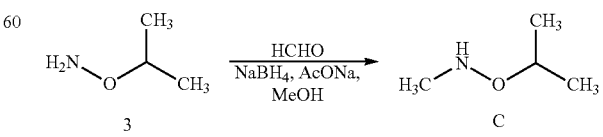

A mixture of O-isopropylhydroxylamine (400.00 mg, 3.59 mmol, 1.00 eq, HCl), AcONa (294.50 mg, 3.59 mmol, 1.00 eq) in MeOH (5.00 mL) was added formaldehyde (874.12 mg, 10.77 mmol, 3.00 eq), and the mixture was stirred at 15° C. for 14 hr under $N_2$. Then $NaBH_4$ (407.43 mg, 10.77 mmol, 3.00 eq) was added at 0° C., the mixture was stirred at 15° C. for 2 hr under $N_2$ atmosphere. TLC showed the reaction was completed. The mixture was poured into ice-water (10 mL) and stirred at 5 min. The aqueous phase was extracted with DCM (5 mL*3). The combined organic phase was washed with brine (10 mL*2), dried with anhydrous $Na_2SO_4$, filtered and then HCl/EA (10 mL) was added, the mixture was concentrated in vacuum to give N-isopropoxymethanamine (56.00 mg, 445.86 umol, 12.42% yield, HCl) as a white oil. $^1$H NMR (400 MHz, METHANOL-$d_4$) ppm δ 4.41-4.50 (m, 1H), 3.16 (s, 2H), 2.97 (s, 2H), 1.33 (d, J=6.15 Hz, 6H).

Preparation of Compound 600

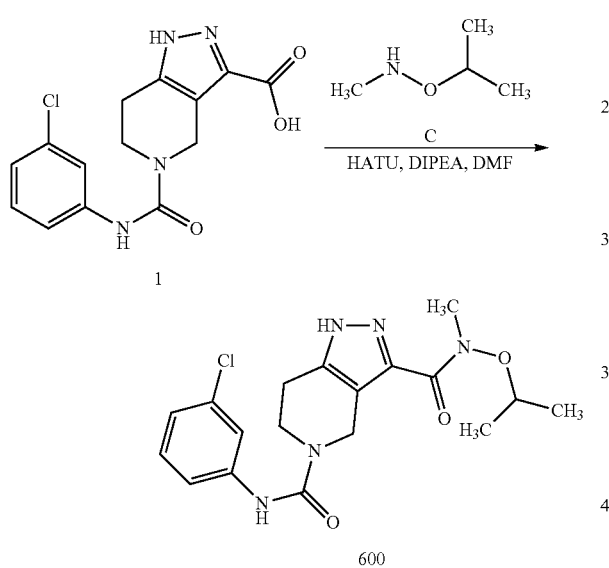

A mixture of 5-[(3-chlorophenyl)carbamoyl]-1,4,6,7-tetrahydropyrazolo [4,3-c]pyridine-3-carboxylic acid (50.00 mg, 155.89 umol, 1.00 eq), N-isopropoxymethanamine (23.50 mg, 187.07 umol, 1.20 eq, HCl), HATU (59.27 mg, 155.89 umol, 1.00 eq), and DIPEA (50.37 mg, 389.72 umol, 2.50 eq) in DMF (2.00 mL) was degassed and purged with $N_2$ for 3 times, and then the mixture was stirred at 15° C. for 16 hours under $N_2$ atmosphere. LCMS showed the reaction was completed. The mixture was poured into water (5 mL) and stirred at 5 min. The aqueous phase was extracted with ethyl acetate (3 mL*3). The combined organic phase was washed with brine (5 mL*2), dried with anhydrous $Na_2SO_4$, filtered and concentrated in vacuum. The residue was purified by prep-HPLC (FA) to give N5-(3-chlorophenyl)-N3-isopropoxy-N3-methyl-1,4,6,7-tetrahydropyrazolo[4,3-c]pyridine-3,5-dicarboxamide (20.00 mg, 50.89 umol, 32.64% yield, 99.7% purity) as a white solid. LCMS: 392/394 [M+1]. $^1$H NMR (300 MHz, METHANOL-$d_4$) ppm δ 7.51 (t, J=1.88 Hz, 1H), 7.26-7.32 (m, 1H), 7.24 (d, J=7.91 Hz, 1H), 7.00 (d, J=7.72 Hz, 1H), 4.70 (br. s., 2H), 4.29 (br. s., 1H), 3.82 (t, J=5.84 Hz, 2H), 3.36-3.60 (m, 3H), 2.85 (t, J=5.75 Hz, 2H), 1.18 (br. s., 6H).

Example 7

Preparation of Compounds 697 and 698

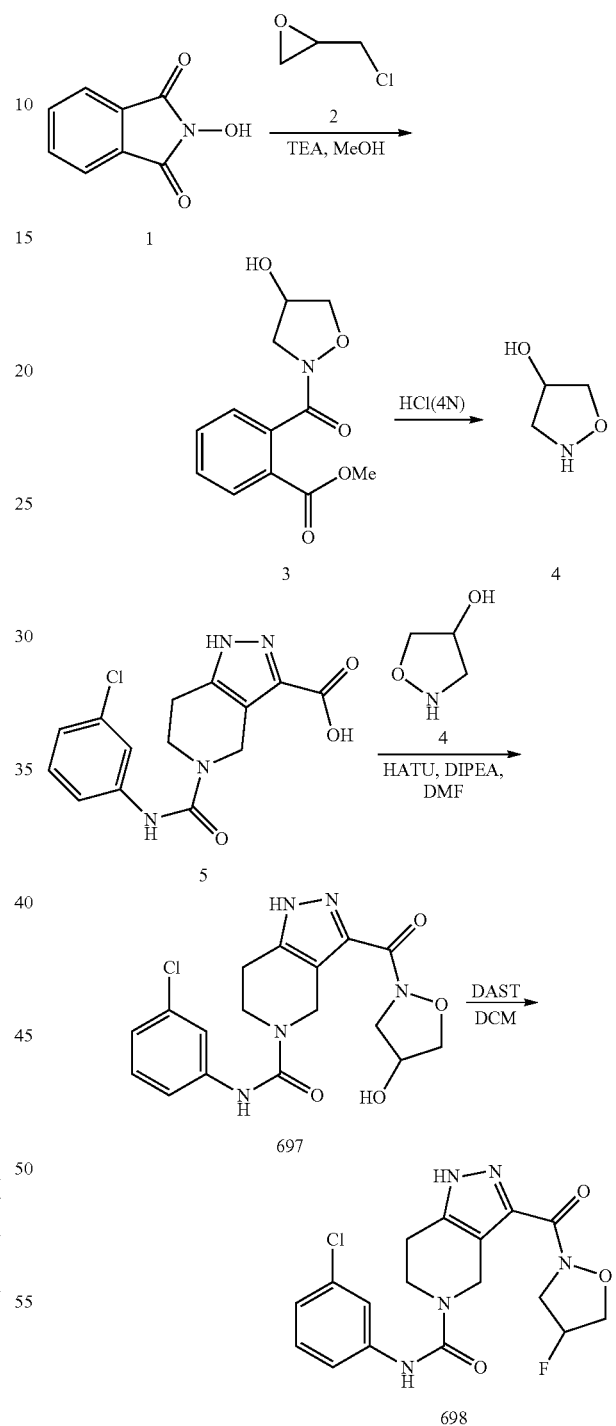

Step 1: Preparation of Compound 3

A mixture of 2-hydroxyisoindoline-1,3-dione (5.06 g, 31.00 mmol, 1.00 eq), 2-(chloromethyl)oxirane (3.15 g, 34.10 mmol, 1.10 eq), and TEA (3.45 g, 34.10 mmol, 1.10 eq) in MeOH (20.00 mL) was degassed and purged with $N_2$ for 3 times, and then the mixture was stirred at 50° C. for 12 hours under N₂ atmosphere. LCMS showed that the starting material 1 was consumed, and the desired product formed. The mixture was concentrated in vacuo. The residue was dissolved with EA (30 mL) and water (10 mL). The aqueous phase was extracted with EA (30 mL). The combined organic phase was washed with 1N HCl (20 mL), dried over Na₂SO₄ and concentrated in vacuo to give an oil. 5 mL of EA was added to resolve the oil, and the mixture stood at 19° C. for 16 hours. A white solid formed. The solid was collected by filtration, washed by EA, and dried in high vacuo to afford methyl 2-(4-hydroxyisoxazolidine-2-carbonyl)benzoate (3.60 g, 14.33 mmol, 46.22% yield) as white solid. LCMS: 252 [M+1]. ¹H NMR (400 MHz, METHANOL-d₄) ppm δ 7.99-8.00 (m, 1H), 7.66-769 (m, 1H), 7.55-7.59 (m, 1H), 7.46-7.48 (m, 1H), 4.87-4.88 (m, 1H), 4.14-4.17 (m, 1H), 3.68-3.93 (m, 5H), 3.32-3.33 (m, 1H).

Step 4: Preparation of Compound 4

A mixture of methyl 2-(4-hydroxyisoxazolidine-2-carbonyl)benzoate (2.30 g, 9.15 mmol, 1.00 eq) in 4N of aqueous HCl (20.00 mL) solution was heated to reflux (100° C.) for 6 hours. Lots of white solid was formed when the reaction was cooled to room temperature 20° C. TLC showed the reaction was completed. The reaction mixture was filtrated and the filtrate was concentrated in vacuo. The resulting solid was rinsed with i-PrOH (50 mL). The solid was dried in vacuo to afford isoxazolidin-4-ol (680.00 mg, 5.42 mmol, 59.19% yield, HCl) as white solid. The organic phase was concentrated in vacuo to give desired product (75 mg) as an off-white solid. ¹H NMR (300 MHz, METHANOL-d₄) ppm δ 4.95-4.96 (m, 1H), 4.21-4.27 (m, 2H), 3.58-3.66 (m, 2H).

Preparation of Compound 697

A mixture of 5-[(3-chlorophenyl)carbamoyl]-1,4,6,7-tetrahydropyrazolo[4,3-c]pyridine-3-carboxylic acid (100.00 mg, 311.79 umol, 1.00 eq), isoxazolidin-4-ol (27.78 mg, 311.79 umol, 1.00 eq), HATU (142.26 mg, 374.15 umol, 1.20 eq), and DIPEA (100.74 mg, 779.47 umol, 136.14 uL, 2.50 eq) in DMF (2.00 mL) was degassed and purged with N₂ for 3 times. Then the mixture was stirred at 15° C. for 3 hr under N₂ atmosphere. LCMS showed the reaction was completed. The mixture was poured into water (5 mL) and stirred at 5 min. The aqueous phase was extracted with ethyl acetate (3 mL*3). The combined organic phase was washed with brine (5 mL*2), dried with anhydrous Na₂SO₄, filtered and concentrated in vacuum. The residue was purified by prep-HPLC (FA) to give N-(3-chlorophenyl)-3-(4-hydroxy-isoxazolidine-2-carbonyl)-1,4,6,7-tetrahydropyrazolo[4,3-c]pyridine-5-carboxamide (45.00 mg, 114.28 umol, 36.65% yield, 99.5% purity) as a white solid. LCMS: 392/394 [M+1]. ¹H NMR (400 MHz, METHANOL-d₄) ppm δ 7.50-7.53 (m, 1H), 7.28 (s, 1H), 7.19-7.25 (m, 1H), 7.00 (d, J=7.91 Hz, 1H), 4.80 (br. s., 1H), 4.75 (s, 2H), 4.07 (d, J=3.39 Hz, 4H), 3.82 (d, J=5.40 Hz, 2H), 2.85 (t, J=5.71 Hz, 2H).

Preparation of Compound 698

A mixture of N-(3-chlorophenyl)-3-(4-hydroxyisoxazolidine-2-carbonyl)-1,4,6,7-tetrahydropyrazolo[4,3-c]pyridine-5-carboxamide (62.00 mg, 158.24 umol, 1.00 eq) in DCM (3.00 mL) was added DAST (51.01 mg, 316.48 umol, 41.81 uL, 2.00 eq) at −78° C. under N₂. Then the mixture was stirred at 15° C. for 16 hours under N₂ atmosphere. LCMS showed the reaction was completed. The mixture was poured into water (5 mL) and stirred at 5 min. The aqueous phase was extracted with DCM (3 mL*3). The combined organic phase was washed with brine (5 mL), dried with anhydrous Na₂SO₄, filtered and concentrated in vacuum. The residue was purified by prep-HPLC (FA) to give N-(3-chlorophenyl)-3-(4-fluoroisoxazolidine-2-carbonyl)-1,4,6,7-tetrahydropyrazolo[4,3-c]pyridine-5-carboxamide (10.00 mg, 24.38 umol, 15.41% yield, 96% purity) as a white solid. LCMS: 394/396 [M+1]. ¹H NMR (400 MHz, METHANOL-d₄) ppm δ 7.52 (t, J=1.94 Hz, 1H), 7.26-7.31 (m, 1H), 7.20-7.25 (m, 1H), 6.98-7.02 (m, 1H), 5.58-5.77 (m, 1H), 4.75 (s, 2H), 4.20-4.48 (m, 3H), 4.01-4.16 (m, 1H), 3.79-3.86 (m, 2H), 2.85 (t, J=5.65 Hz, 2H).

Example 8

Preparation of Compound 699

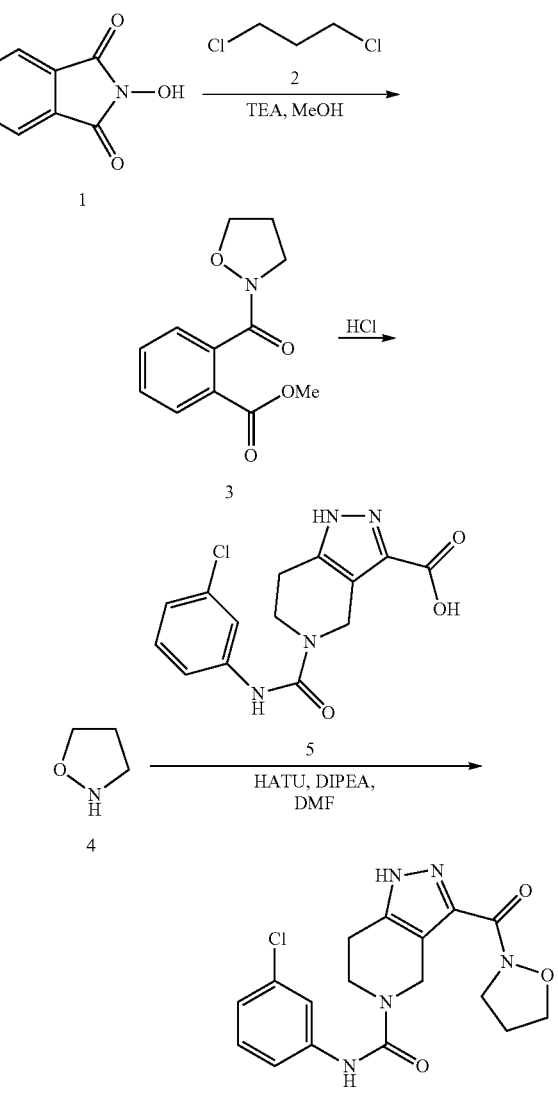

Step 1: Preparation of Compound 3

A mixture of 2-hydroxyisoindoline-1,3-dione (5.00 g, 30.65 mmol, 1.00 eq), TEA (9.30 g, 91.95 mmol, 12.74 mL, 3.00 eq), 1,3-dichloropropane (4.16 g, 36.78 mmol, 1.20 eq) in MeOH (50.00 mL) was degassed and purged with N₂ for 3 times, and then the mixture was stirred at 15° C. for 16 hours under N₂ atmosphere. LCMS showed the starting material was major. The mixture was stirred at 60° C. for 16 hr under N₂ atmosphere. LCMS showed the reaction was completed. The mixture was poured into ice Na₂CO₃ (50 mL) and stirred at 5 min. The aqueous phase was extracted with ethyl acetate (25 mL*2). The combined organic phase was washed with brine (50 mL*1), dried with anhydrous Na₂SO₄, filtered and concentrated in vacuum. The residue was purified by column chromatography (SiO2, Petroleum ether/Ethyl acetate=100/1 to 1/1) (TLC: DCM/MeOH=10/1). But the desired product and the starting material was not separated, and the mixture was washed by Na₂CO₃ (50 mL*3). Then the organic phase was dried with anhydrous Na₂SO₄, filtered and concentrated in vacuum to give methyl-2-(isoxazolidine-2-carbonyl) benzoate (3.20 g, 13.60 mmol, 44.38% yield) as a white oil. LCMS: 236 [M+1].

Step 2: Preparation of Compound 4

A mixture of methyl 2-(isoxazolidine-2-carbonyl)benzoate (1.50 g, 6.38 mmol, 1.00 eq) in HCl (4 M, 12.00 mL, 7.53 eq), and then the mixture was stirred at 100° C. for 16 hours under N₂ atmosphere. TLC showed the reaction was completed. The mixture was filtered and the aqueous phase was concentrated in vacuum to give isoxazolidine (523.00 mg, 4.77 mmol, 74.83% yield, HCl) as a white solid. ¹H NMR (300 MHz, METHANOL-d₄) ppm δ 2.59 (t, J=6.78 Hz, 2H), 1.95 (t, J=7.25 Hz, 2H), 0.84 (quin, J=6.97 Hz, 2H).

Preparation of Compound 699

A mixture of 5-[(3-chlorophenyl)carbamoyl]-1,4,6,7-tetrahydropyrazolo-[4,3-c]pyridine-3-carboxylic acid (80.00 mg, 249.43 umol, 1.00 eq), isoxazolidine (40.99 mg, 374.15 umol, 1.50 eq, HCl), DIPEA (80.59 mg, 623.58 umol, 108.91 uL, 2.50 eq), HATU (142.26 mg, 374.15 umol, 1.50 eq) in DMF (2.00 mL) was degassed and purged with N₂ for 3 times, and then the mixture was stirred at 15° C. for 16 hours under N₂ atmosphere. LCMS showed the reaction was completed. The mixture was poured into water (5 mL) and stirred at 5 min. The aqueous phase was extracted with ethyl acetate (3 mL*3). The combined organic phase was washed with brine (5 mL*2), dried with anhydrous Na₂SO₄, filtered and concentrated in vacuum. The residue was purified by prep-HPLC (FA) to give N-(3-chlorophenyl)-3-(isoxazolidine-2-carbonyl)-1,4,6,7-tetrahydropyrazolo[4,3-c]pyridine-5-carboxamide (35.00 mg, 93.13 umol, 37.34% yield) as a white solid. LCMS: 376/378 [M+1]. ¹H NMR (400 MHz, METHANOL-d₄) ppm δ 7.50-7.53 (m, 1H), 7.27-7.31 (m, 1H), 7.20-7.25 (m, 1H), 6.97-7.02 (m, 1H), 4.75 (s, 2H), 4.12 (t, J=6.59 Hz, 4H), 3.82 (t, J=5.77 Hz, 2H), 2.85 (t, J=5.71 Hz, 2H), 2.42 (quin, J=7.09 Hz, 2H).

Example 9

Preparation of Compound 695

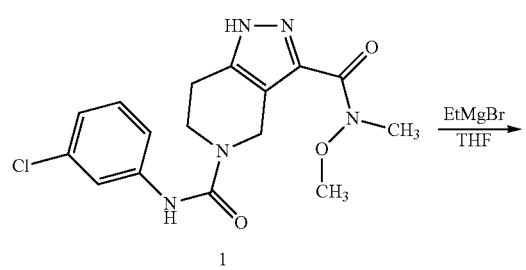

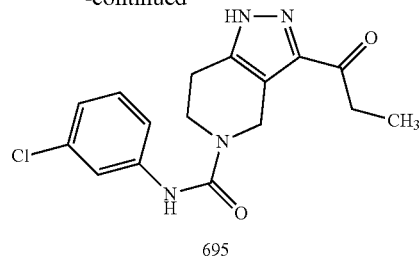

Preparation of Compound 695

To a solution of EtMgBr (1 M, 4.12 mL, 5.00 eq) was added a solution of N⁵-(3-chlorophenyl)-N³-methoxy-N³-methyl-1,4,6,7-tetrahydropyrazolo[4,3-c]pyridine-3,5-dicarboxamide (300.00 mg, 824.63 umol, 1.00 eq) in THF (5.00 mL) at −10° C. The mixture was stirred at 15° C. for 3 hr. TLC (PE:EA=0:1) showed starting material was remained. EtMgBr (1 M, 4.12 mL, 5.00 eq) was added at −10° C. The mixture was stirred at 15° C. for 2 hr. The mixture was quenched by saturated with NH₄Cl (10 mL) and extracted with EA (20 mL*2). The combined organic layer was dried over Na₂SO₄, filtrated, and concentrated in vacumm. The residue was purified by prep-TLC (PE:EA=0:1) to afford N-(3-chlorophenyl)-3-propanoyl-1,4,6,7-tetrahydropyrazolo[4,3-c]pyridine-5-carboxamide (100.00 mg, 287.88 umol, 34.91% yield, 95.8% purity) as white solid. ¹H NMR (400 MHz, METHANOL-d4) δ=7.54 (t, J=1.9 Hz, 1 H), 7.29-7.33 (m, 1 H), 7.22-7.27 (m, 1 H), 7.02 (d, J=7.9 Hz, 1 H), 4.76 (s, 2 H), 3.82 (t, J=5.6 Hz, 2 H), 3.03 (q, J=7.4 Hz, 2 H), 2.87 (t, J=5.7 Hz, 2 H), 1.12-1.23 (m, 3 H). LCMS: 333/335[M+1].

Example 10

Preparation of Compounds 911 and 912

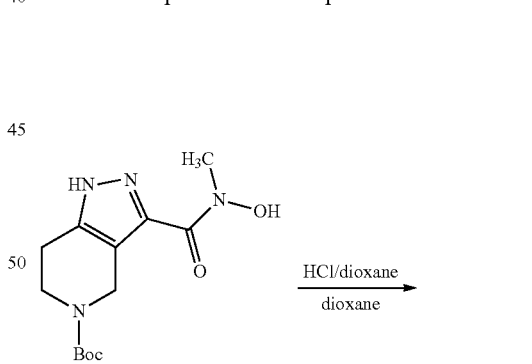

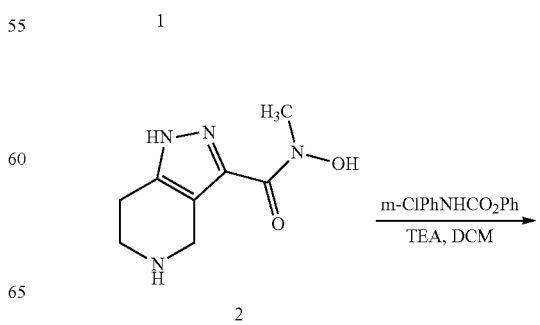

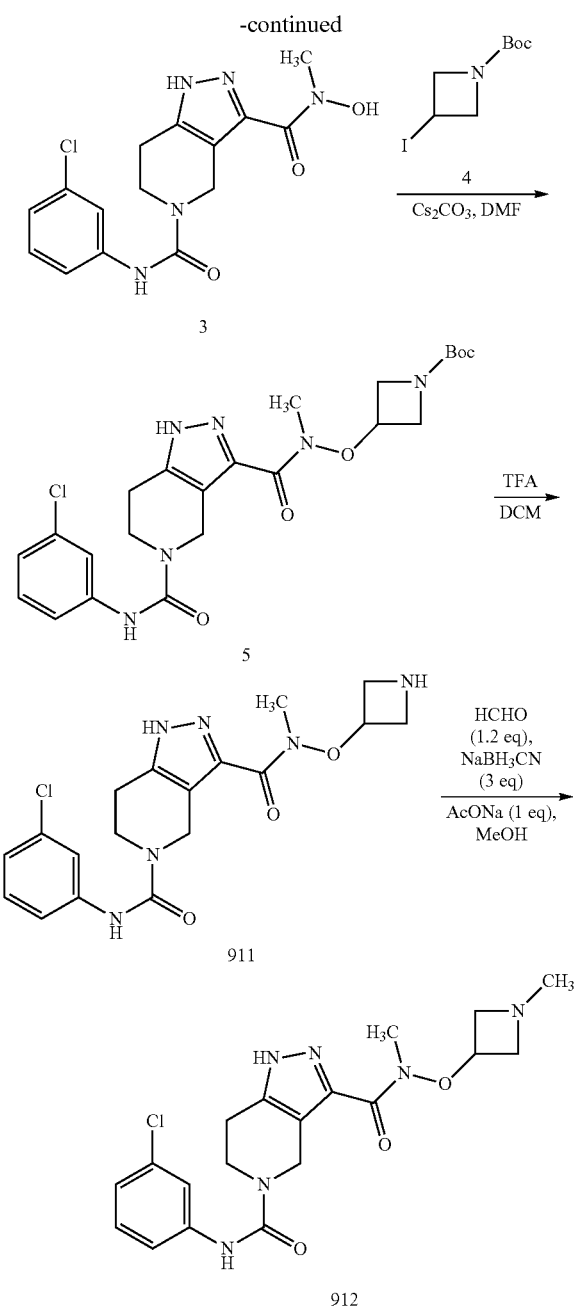

Step 1: Preparation of Compound 2

A mixture of tert-butyl3-[hydroxy(methyl)carbamoyl]-1,4,6,7-tetrahydropyrazolo [4,3-c]pyridine-5-carboxylate (300.00 mg, 1.01 mmol, 1.00 eq) in dioxane (3.00 mL) was added HCl/dioxane (1.01 mmol, 5.00 mL, 1.00 eq), and then the mixture was stirred at 25° C. for 1 hour. LCMS and TLC showed the reaction was completed. The mixture was concentrated in vacuum to give N-hydroxy-N-methyl-4,5,6,7-tetrahydro-1H-pyrazolo[4,3-c]pyridine-3-carboxamide (235.00 mg, 1.01 mmol, 100.00% yield, HCl) as a white solid, which was used directly for next step. LCMS: 233 [M+1]

Step 2: Preparation of Compound 3

A mixture of N-hydroxy-N-methyl-4,5,6,7-tetrahydro-1H-pyrazolo[4,3-c]pyridine-3-carboxamide (235.00 mg, 1.20 mmol, 1.00 eq), phenyl N-(3-chlorophenyl) carbamate (297.22 mg, 1.20 mmol, 1.00 eq), TEA (303.57 mg, 3.00 mmol, 415.85 uL, 2.50 eq) in DCM (5.00 mL) was degassed and purged with $N_2$ for 3 times, and then the mixture was stirred at 30° C. for 16 hour under N2 atmosphere. LCMS showed the reaction was completed. The mixture was poured into water (10 mL) and stirred at 5 min. The aqueous phase was extracted with DCM (5 mL*3). The combined organic phase was washed with brine (10 mL), dried with anhydrous $Na_2SO_4$, filtered and concentrated in vacuum. The residue was purified by column chromatography ($SiO_2$, Petroleum ether/Ethyl acetate=100/1 to 1/1) to give N5-(3-chlorophenyl)-N3-hydroxy-N3-methyl-1,4,6,7-tetrahydro-pyrazolo[4,3-c]pyridine-3,5-dicarboxamide (352.00 mg, 966.12 umol, 80.51% yield, 96% purity) as a white solid. LCMS: 350/352 [M+1].

Step 3: Preparation of Compound 5

A mixture of N5-(3-chlorophenyl)-N3-hydroxy-N3-methyl-1,4,6,7-tetrahydropyrazolo[4,3-c]pyridine-3,5-dicarboxamide (225.00 mg, 643.28 umol, 1.00 eq), tert-butyl 3-iodoazetidine-1-carboxylate (200.33 mg, 707.61 umol, 1.10 eq), $Cs_2CO_3$ (314.39 mg, 964.92 umol, 1.50 eq) in DMF (3.00 mL) was degassed and purged with $N_2$ for 3 times, and then the mixture was stirred at 30° C. for 16 hour under $N_2$ atmosphere. LCMS showed the starting material was consumed completely. The mixture was poured into water (10 mL) and stirred for 5 min. The aqueous phase was extracted with ethyl acetate (5 mL*3). The combined organic phase was washed with brine (10 mL*2), dried with anhydrous $Na_2SO_4$, filtered and concentrated in vacuum. The residue was purified by Prep-TLC to give tert-butyl 3-[[5-[(3-chlorophenyl)carbamoyl]-1,4,6,7-tetrahydropyrazolo[4,3-c]pyridine-3-carbonyl]-methyl-amino]oxyazetidine-1-carboxylate (192.00 mg, 349.80 umol, 54.38% yield, 92% purity) as a white solid. LCMS: 505/507 [M+1].

Preparation of Compound 911

To a mixture of tert-butyl 3-[[5-[(3-chlorophenyl) carbamoyl]-1,4,6,7-tetrahydropyrazolo[4,3-c]pyridine-3-carbonyl]-methyl-amino]oxyazetidine-1-carboxylate (50.00 mg, 99.02 umol, 1.00 eq) in DCM (2.00 mL) was added TFA (3.85 g, 33.76 mmol, 2.50 mL, 340.98 eq), and then the mixture was stirred at 15° C. for 1 hour. LCMS showed the reaction was completed. The mixture was concentrated in vacuum to give 51 mg of crude product. 21 mg was purified by Prep-HPLC (FA) to give pure N3-(azetidin-3-yloxy)-N5-(3-chlorophenyl)-N3-methyl-1,4,6,7-tetrahydro pyrazolo[4,3-c]pyridine-3,5-dicarboxamide (12.00 mg, 22.20 umol, 22.42% yield, 96% purity, TFA) as a white solid. $^1$H NMR (400 MHz, METHANOL-d4) δ ppm 7.51 (t, J=1.88 Hz, 1 H) 7.26-7.31 (m, 1 H) 7.20-7.26 (m, 1 H) 7.01 (d, J=7.91 Hz, 1 H) 5.01 (s, 1 H) 4.71 (s, 2 H) 4.31-4.41 (m, 2 H) 4.18-4.28 (m, 2 H) 3.82 (t, J=5.65 Hz, 2 H) 3.61 (s, 3 H) 2.86 (t, J=5.71 Hz, 2 H). LCMS: 405/407 [M+1].

Preparation of Compound 912

A mixture of N3-(azetidin-3-yloxy)-N5-(3-chlorophenyl)-N3-methyl-1,4,6,7-tetrahydropyrazolo[4,3-c]pyridine-3,5-dicarboxamide (30.00 mg, 57.82 umol, 1.00 eq, TFA), HCHO (4.69 mg, 57.82 umol, 4.31 uL, 37% purity, 1.00 eq), NaBH3CN (10.90 mg, 173.45 umol, 3.00 eq) and AcONa (4.74 mg, 57.82 umol, 1.00 eq) in MeOH (2.00 mL) was degassed and purged with $N_2$ for 3 times, and then the mixture was stirred at 15° C. for 16 hour under $N_2$ atmosphere. LCMS showed the reaction was completed. The mixture was poured into water (5 mL) and stirred at 5 min. The aqueous phase was extracted with ethyl acetate (3 mL*3). The combined organic phase was washed with brine (5 mL), dried with anhydrous $Na_2SO_4$, filtered and concentrated in vacuum. The residue was purified by Prep-HPLC (FA) to give N5-(3-chlorophenyl)-N3-methyl-N3-(1-methylazetidin-3-yl)oxy-1,4,6,7-tetrahydropyrazolo[4,3-c]pyridine-3,5-dicarboxamide (11.00 mg, 26.00 umol, 44.96% yield, 99% purity) as a white solid. $^1$H NMR (400 MHz, METHANOL-d4) δ ppm 7.52 (t, J=1.88 Hz, 1 H) 7.28 (s, 1 H) 7.24 (d, J=7.91 Hz, 1 H) 7.00 (d, J=7.78 Hz, 1 H) 4.92-4.95 (m, 1 H) 4.71 (s, 2 H) 4.20-4.32 (m, 2 H) 3.99-4.11 (m, 2 H) 3.82 (s, 2 H) 3.57 (s, 3 H) 2.80-2.90 (m, 5 H). LCMS: 419/421 [M+1].

Example 11

Preparation of Compound 937

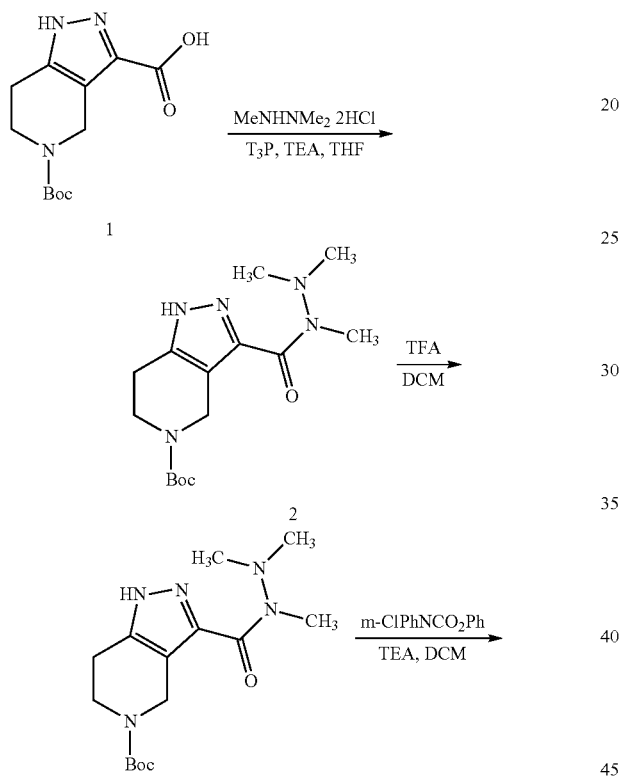

Step 1: Preparation of Compound 2

To a mixture of 5-tert-butoxycarbonyl-1,4,6,7-tetrahydropyrazolo[4,3-c]pyridine-3-carboxylic acid (150.00 mg, 561.21 umol, 1.00 eq) and 1,1,2-trimethylhydrazine (165.05 mg, 1.12 mmol, 2.00 eq, 2HCl) in THF (5.00 mL) was added T$_3$P (1.79 g, 2.81 mmol, 1.67 mL, 50% purity, 5.01 eq) and TEA (170.37 mg, 1.68 mmol, 233.38 uL, 3.00 eq), the reaction mixture was stirred at 75° C. for 16 hours. TLC indicated compound 1 was consumed completely and one major new spot with lower polarity was detected. The mixture was extracted with EA (100 mL*3) and washed with water (80 mL*2), the organic phase was dried with anhydrous Na$_2$SO$_4$, filtered and concentrated in vacuum. The residue was purified by silica gel chromatography to afford tert-butyl-3-[dimethylamino(methyl) carbamoyl]-1,4,6,7-tetrahydropyrazolo[4,3-c]pyridine-5-carboxylate (135.00 mg, 404.93 umol, 72.15% yield, 97% purity) as red solid.

Step 2: Preparation of Compound 3

To a solution of tert-butyl 3-[dimethylamino(methyl)carbamoyl]-1,4,6,7-tetrahydropyrazolo[4,3-c]pyridine-5-carboxylate (60.00 mg, 185.53 umol, 1.00 eq) in DCM (1.00 mL) was added TFA (1.54 g, 13.51 mmol, 1.00 mL, 72.80 eq), the reaction mixture was stirred at 20° C. for one hour. LCMS showed starting material was consumed completely and one main peak with desired MS was detected. Removed the solvent on a rotary evaporator to afford N,N',N'-trimethyl-4,5,6,7-tetrahydro-1H-pyrazolo[4,3-c]pyridine-3-carbohydrazide (50.00 mg, crude, TFA) as red solid. The crude product was used in the next step directly without purification.

Preparation of Compound 937

To a mixture of N,N',N'-trimethyl-4,5,6,7-tetrahydro-1H-pyrazolo[4,3-c]pyridine-3-carbohydrazide (50.00 mg, 148.24 umol, 1.00 eq, TFA) in DCM (5.00 mL) was added TEA (45.00 mg, 444.71 umol, 61.64 uL, 3.00 eq), followed by phenyl N-(3-chlorophenyl)carbamate (36.72 mg, 148.24 umol, 1.00 eq), the reaction mixture was stirred at 20° C. for 16 hours. LCMS showed phenyl N-(3-chlorophenyl) carbamate was consumed completely and 40% of desired compound was detected. The mixture was extracted with DCM (80 mL*3) and washed with water (50 mL*2), the organic phase was dried with anhydrous Na$_2$SO$_4$, filtered and concentrated in vacuum. Further purification by prep-HPLC (FA) to afford Compound 937 (23.00 mg, 61.03 umol, 41.17% yield, 100% purity) as white solid. $^1$H NMR (400 MHz, METHANOL-d4) δ ppm 7.52-7.53 (t, J=1.88 Hz, 1 H) 7.28-7.30 (m, 1 H) 7.20-7.24 (m, 1 H) 6.98-7.00 (d, J=7.91 Hz, 1 H) 4.76 (s, 2 H) 3.80-3.82 (t, J=5.77 Hz, 2 H) 3.05 (s, 3 H) 2.83-2.85 (m, 2 H) 2.65 (s, 6 H). LCMS: 377/379 [M+1].

Example 12

Preparation of Compound 910

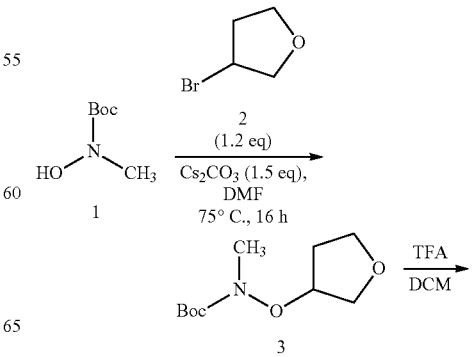

-continued

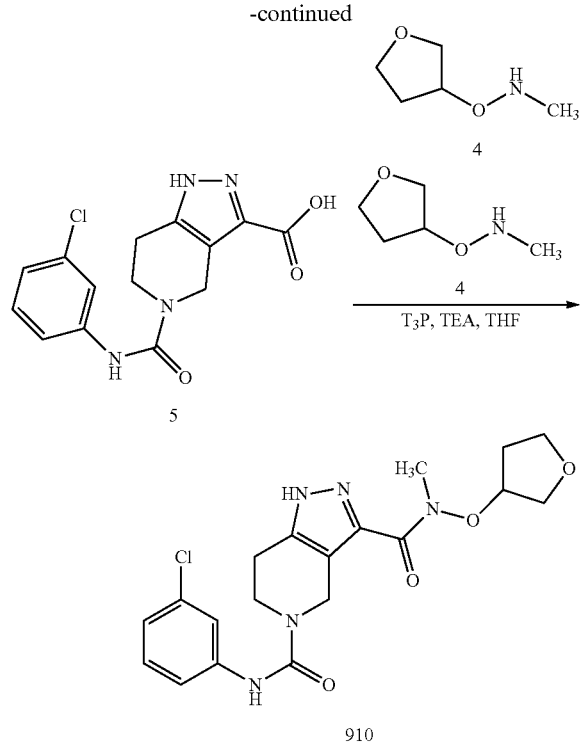

Step 1: Preparation of Compound 3

A mixture of tert-butyl N-hydroxy-N-methyl-carbamate (1.00 g, 6.79 mmol, 1.00 eq), 3-bromotetrahydrofuran (1.23 g, 8.15 mmol, 1.20 eq), $Cs_2CO_3$ (3.32 g, 10.18 mmol, 1.50 eq) in DMF (10.00 mL) was degassed and purged with $N_2$ for 3 times, and then the mixture was stirred at 70° C. for 16 hour under $N_2$ atmosphere. TLC showed the reaction was completed. The mixture was poured into water (20 mL) and stirred at 5 min. The aqueous phase was extracted with ethyl acetate (15 mL*2). The combined organic phase was washed with brine (20 mL), dried with anhydrous $Na_2SO_4$, filtered and concentrated in vacuum. The residue was purified by column chromatography ($SiO_2$, Petroleum ether/Ethyl acetate=100/1 to 50/1) to give tert-butyl N-methyl-N-tetrahydrofuran-3-yloxy-carbamate (905.00 mg, 4.17 mmol, 61.35% yield) as a colorless oil. $^1$H NMR (400 MHz, CHLOROFORM-d) δ ppm 4.62-4.71 (m, 1 H) 3.89-4.01 (m, 2 H) 3.81-3.88 (m, 1 H) 3.75 (dd, J=10.54, 4.39 Hz, 1 H) 3.10 (s, 3 H) 2.13 (dtdd, J=12.23, 5.32, 5.32, 2.54, 1.32 Hz, 1 H) 1.92-2.05 (m, 1 H) 1.47-1.53 (m, 9 H).

Step 2: Preparation of Compound 4

A mixture of tert-butyl N-methyl-N-tetrahydrofuran-3-yloxy-carbamate (100.00 mg, 460.28 umol, 1.00 eq) in DCM (4.00 mL) was added TFA (3.08 g, 27.01 mmol, 2.00 mL, 58.69 eq), and then the mixture was stirred at 15° C. for 0.5 hour. TLC showed the reaction was completed. The mixture was concentrated in vacuum to give N-tetrahydrofuran-3-yloxymethanamine (106.40 mg, 460.27 umol, 100.00% yield, TFA) as a yellow oil, which was used directly for next step.

Preparation of Compound 910

A mixture of 5-[(3-chlorophenyl)carbamoyl]-1,4,6,7-tetrahydropyrazolo[4,3-c]pyridine-3-carboxylic acid (80.00 mg, 249.43 umol, 1.00 eq), N-tetrahydrofuran-3-yloxymethanamine (103.79 mg, 448.97 umol, 1.80 eq, TFA), $T_3P$ (476.18 mg, 748.29 umol, 445.03 uL, 50% purity, 3.00 eq), TEA (113.58 mg, 1.12 mmol, 155.59 uL, 4.50 eq) in DCM (3.00 mL) was degassed and purged with $N_2$ for 3 times, and then the mixture was stirred at 15° C. for 16 hour under $N_2$ atmosphere. LCMS showed the reaction was completed. The mixture was poured into water (10 mL) and stirred at 5 min. The aqueous phase was extracted with DCM (5 mL*3). The combined organic phase was washed with brine (10 mL), dried with anhydrous $Na_2SO_4$, filtered and concentrated in vacuum. The residue was purified by Prep-HPLC (FA) to give N5-(3-chlorophenyl)-N3-methyl-N3-tetrahydrofuran-3-yloxy-1,4,6,7-tetrahydropyrazolo[4,3-c]pyridine-3,5-dicarboxamide (40.00 mg, 94.32 umol, 37.81% yield, 99% purity) as a white solid. $^1$H NMR (400 MHz, METHANOL-d4) δ ppm 7.52 (t, J=2.01 Hz, 1 H) 7.27-7.31 (m, 1 H) 7.20-7.26 (m, 1 H) 6.97-7.03 (m, 1 H) 4.71 (br. s., 2 H) 3.97 (d, J=9.16 Hz, 1 H) 3.73-3.85 (m, 4 H) 3.58 (br. s., 2 H) 3.32 (br. s., 3 H) 2.85 (t, J=5.71 Hz, 2 H) 2.00-2.19 (m, 2 H). LCMS: 420/422 [M+1].

Example 13

Preparation of Compound 828

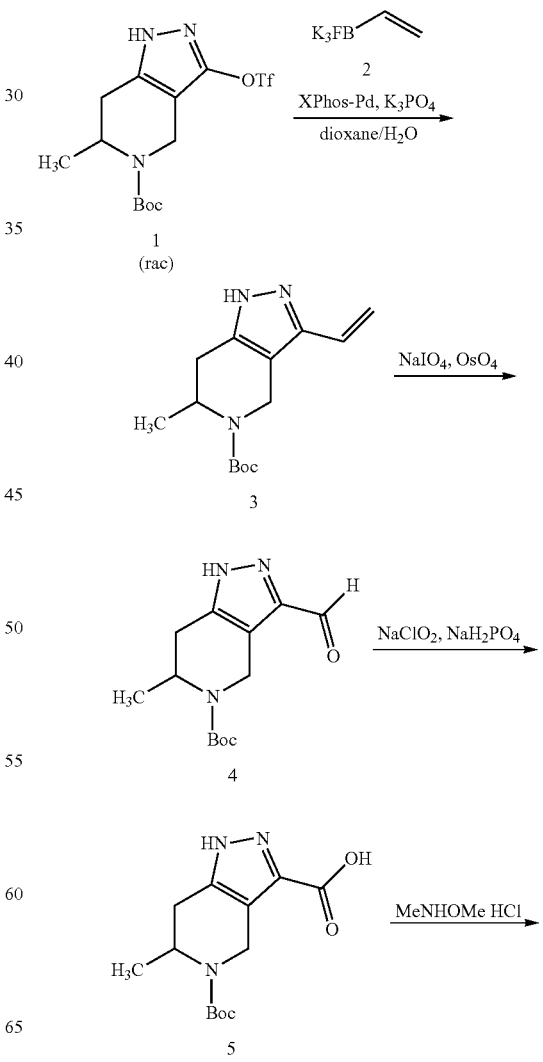

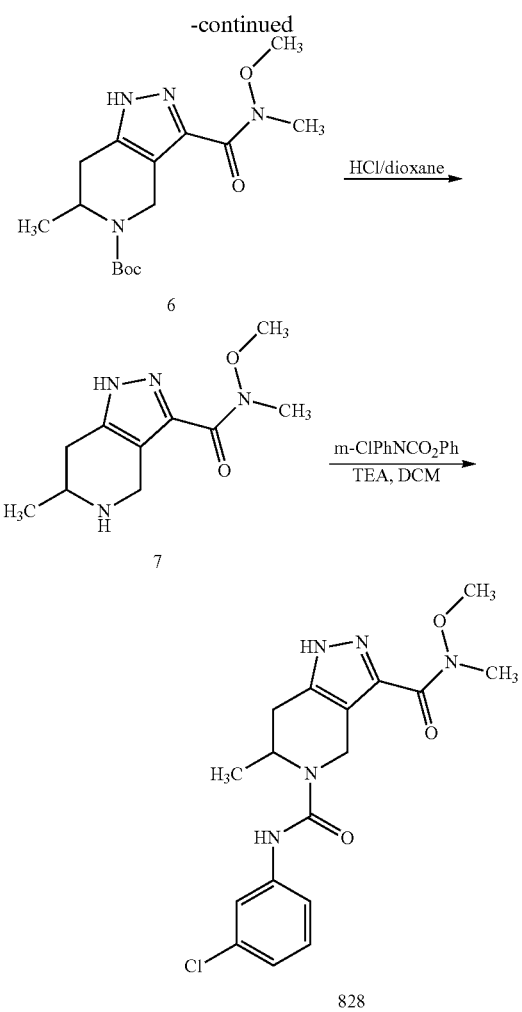

Step 1: Preparation of Compound 3

To a mixture of tert-butyl 6-methyl-3-(trifluoromethylsulfonyloxy)-1,4,6,7-tetrahydro pyrazolo[4,3-c]pyridine-5-carboxylate (100.00 mg, 259.50 umol, 1.00 eq) and [trifluoro(vinyl)-boranyl]potassium(1+) (52.14 mg, 389.25 umol, 1.50 eq) in dioxane (2.00 mL) was added XPhos-Pd-G2 (20.42 mg, 25.95 umol, 0.10 eq) and $K_3PO_4$ (165.25 mg, 778.49 umol, 3.00 eq) in one portion under $N_2$. The mixture was stirred at 110° C. for 12 hours. TLC (Petroleum ether: Ethyl acetate=2:1) showed the reaction was completed. The mixture was poured into water (15 mL) and stirred for 2 min. The aqueous phase was extracted with ethyl acetate (15 mL*2). The combined organic phase was washed with brine (15 mL*2), dried with anhydrous $Na_2SO_4$, filtered and concentrated in vacuum. The residue was purified by prep-TLC (Petroleum ether/Ethyl acetate=2/1) to afford tert-butyl 6-methyl-3-vinyl-1,4,6,7-tetrahydropyrazolo[4,3-c]pyridine-5-carboxylate (35.00 mg, 132.91 umol, 51.22% yield) as yellow oil. LCMS: 264[M+1].

Step 2: Preparation of Compound 4

To a mixture of tert-butyl-6-methyl-3-vinyl-1,4,6,7-tetrahydropyrazolo[4,3-c]pyridine-5-carboxylate (90.00 mg, 341.78 umol, 1.00 eq) in THF (10.00 mL) and $H_2O$ (2.00 mL) was added $NaIO_4$ (146.21 mg, 683.55 umol, 37.88 uL, 2.00 eq) and $OsO_4$ (8.69 mg, 34.18 umol, 1.77 uL, 0.10 eq) in one portion at 20° C. The mixture was stirred at 20° C. for 3 hours. LCMS showed the reaction was completed. The mixture was quenched with saturated $Na_2SO_3$ (10 mL) and stirred for 5 min. The aqueous phase was extracted with ethyl acetate (10 mL*2). The combined organic phase was washed with brine (10 mL*2), dried with anhydrous $Na_2SO_4$, filtered and concentrated in vacuum to afford tert-butyl 3-formyl-6-methyl-1,4,6,7-tetrahydro pyrazolo[4,3-c]pyridine-5-carboxylate (90.00 mg, crude) as yellow oil. LCMS: 266[M+1].

Step 3: Preparation of Compound 5

To a mixture of tert-butyl 3-formyl-6-methyl-1,4,6,7-tetrahydropyrazolo[4,3-c]pyridine-5-carboxylate (90.00 mg, 339.23 umol, 1.00 eq) in t-BuOH (4.00 mL) was added 2-methylbut-2-ene (2.97 g, 42.35 mmol, 4.50 mL, 124.84 eq) drop-wise at 0° C., then $NaH_2PO_4$ (203.50 mg, 1.70 mmol, 5.00 eq) and sodium chlorite (306.80 mg, 3.39 mmol, 10.00 eq) in $H_2O$ (1.60 mL) was added to the mixture drop-wise at 0° C. The mixture was stirred at 0° C. for 2 hours. LCMS showed the reaction was completed. The mixture was adjusted to pH 9 with solid $NaHCO_3$, the aqueous phase was extracted with ethyl acetate (10 mL*2). The aqueous layer was acidified to pH 4 with 2N HCl, the aqueous phase was extracted with ethyl acetate (10 mL*2). The combined organic phase was washed with brine (10 mL*2), dried with anhydrous $Na_2SO_4$, filtered and concentrated in vacuum to afford 5-tert-butoxycarbonyl-6-methyl-1,4,6,7-tetrahydropyrazolo[4,3-c]pyridine-3-carboxylic acid (67.50 mg, 167.96 umol, 49.51% yield, 70% purity) as yellow solid. LCMS: 282[M+1].

Step 4: Preparation of Compound 6

To a mixture of 5-tert-butoxycarbonyl-6-methyl-1,4,6,7-tetrahydropyrazolo [4,3-c]pyridine-3-carboxylic acid (60.00 mg, 213.29 umol, 1.00 eq) and N-methoxymethanamine hydrochloride (83.22 mg, 853.16 umol, 4.00 eq) in THF (10.00 mL) was added $T_3P$ (407.19 mg, 639.87 umol, 380.55 uL, 50% purity, 3.00 eq) and TEA (64.75 mg, 639.87 umol, 88.70 uL, 3.00 eq) in one portion under $N_2$. The mixture was stirred at 75° C. for 24 hours. LCMS showed the reaction was completed. The mixture was poured into water (20 mL) and stirred for 2 min. The aqueous phase was extracted with ethyl acetate (20 mL*2). The combined organic phase was washed with brine (20 mL*2), dried with anhydrous $Na_2SO_4$, filtered and concentrated in vacuum. The residue was purified by silica gel chromatography (Petroleum ether/Ethyl acetate=3/1) to afford tert-butyl 3-[methoxy(methyl)carbamoyl]-6-methyl-1,4,6,7-tetrahydropyrazolo[4,3-c]pyridine-5-carboxylate (62.00 mg, 191.14 umol, 89.61% yield, 100% purity) as yellow oil. LCMS: 325 [M+1].

Step 5: Preparation of Compound 7

To a mixture of tert-butyl 3-[methoxy(methyl)carbamoyl]-6-methyl-1,4,6,7-tetrahydro pyrazolo[4,3-c]pyridine-5-carboxylate (62.00 mg, 191.14 umol, 1.00 eq) in dioxane (2.00 mL) was added HCl/dioxane (4 M, 9.54 mL, 199.60 eq) in one portion under $N_2$. The mixture was stirred at 20° C. for 2 hours. TLC (Petroleum ether:Ethyl acetate=1:1) showed the reaction was completed. The mixture was concentrated in vacuum to afford N-methoxy-N,6-dimethyl-4,5,6,7-tetrahydro-1H-pyrazolo[4,3-c]pyridine-3-carboxamide (49.83 mg, 191.12 umol, 100.00% yield, HCl) as yellow solid.

Preparation of Compound 828 (E1 & E2)

To a mixture of N-methoxy-N,6-dimethyl-4,5,6,7-tetrahydro-1H-pyrazolo[4,3-c]pyridine-3-carboxamide (49.83 mg, 191.12 umol, 1.00 eq, HCl) and phenyl N-(3-chlorophenyl)carbamate (47.34 mg, 191.12 umol, 1.00 eq) in DCM (5.00 mL) was added TEA (58.02 mg, 573.37 umol, 79.48 uL, 3.00 eq) in one portion under $N_2$. The mixture was stirred at 30° C. for 12 hours. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous Na$_2$SO$_4$, filtered and concentrated in vacuum. The residue was purified by silica gel chromatography (Dichloromethane:Methanol=60:1) to afford N5-(3-chlorophenyl)-N3-methoxy-N3,6-dimethyl-1,4,6,7-tetrahydropyrazolo [4,3-c]pyridine-3,5-dicarboxamide (62.00 mg, 164.10 umol, 85.86% yield) as white solid, which was separated by SFC (EW611-593-P1A_3, Column: OJ (250 mm*50 mm, 10 um) Condition: Base-ETOH gave two enantiomers (16.78 mg of Compound 828 (E1) and 20.42 mg of Compound 828 (E2).

Compound 828 (E1): $^1$H NMR (400 MHz, METHANOL-d4) δ 7.52 (s, 1H), 7.20-7.32 (m, 2H), 6.98-7.04 (m, 1H), 5.08-5.13 (m, 2H), 4.29-4.41 (m, 1H), 3.77 (s, 3H), 3.44-3.60 (m, 3H), 3.01-3.07 (m, 1H), 2.65-2.73 (m, 1H), 1.15-1.25 (m, 3H). LCMS: 378/380 [M+1].

Compound 828 (E2): $^1$H NMR (400 MHz, METHANOL-d4) δ 7.52 (s, 1H), 7.20-7.32 (m, 2H), 6.98-7.04 (m, 1H), 5.08-5.13 (m, 2H), 4.29-4.41 (m, 1H), 3.77 (s, 3H), 3.44-3.60 (m, 3H), 3.01-3.07 (m, 1H), 2.65-2.73 (m, 1H), 1.15-1.25 (m, 3H). LCMS: 378/380 [M+1].

Example 14

HBV Assembly Assay

The interference of compounds from this invention with HBV capsid assembly could be measured using an in vitro assembly assay based on fluorescence quenching, which was developed according to a method described by Zlotnick and coworkers (Nature Biotechnology 2006, 24:358). In a typical assay, a mutant HBV C150 protein (amino acids 1-150, C49A, C61A, C107A, 150C) is cloned into a T7 RNA-polymerase based expression vector, expressed in $E.$ $coli$ and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature. The changes in fluorescence between DMSO treated and compound treated samples are recorded and analyzed for assembly modulation.

Example 15

HBV Replication Inhibition Assay

HBV replication inhibition by the compounds of this invention could be determined in cells infected or transfected with HBV, or cells with stably integrated HBV, such as HepG2.2.15 cells (Sells et al. 1987). In this example, HepG2.2.15 cells were maintained in cell culture medium containing 10% fetal bovine serum (FBS), Geneticin, L-glutamine, penicillin and streptomycin. HepG2.2.15 cells could be seeded in 96-well plates at a density of 40,000 cells/well and be treated with serially diluted compounds at a final DMSO concentration of 0.5% either alone or in combination by adding drugs in a checker box format. Cells were incubated with compounds for three days, after which medium was removed and fresh medium containing compounds was added to cells and incubated for another three days. At day 6, supernatant was removed and treated with DNase at 37° C. for 60 minutes, followed by enzyme inactivation at 75° C. for 15 minutes. Encapsidated HBV DNA was released from the virions and covalently linked HBV polymerase by incubating in lysis buffer (Affymetrix QS0010) containing 2.5 μg proteinase K at 50° C. for 40 minutes. HBV DNA was denatured by addition of 0.2 M NaOH and detected using a branched DNA (BDNA) QuantiGene assay kit according to manufacturer recommendation (Affymetrix). HBV DNA levels could also be quantified using qPCR, based on amplification of encapsidated HBV DNA extraction with QuickExtraction Solution (Epicentre Biotechnologies) and amplification of HBV DNA using HBV specific PCR probes that can hybridize to HBV DNA and a fluorescently labeled probe for quantitation. In addition, cell viability of HepG2.2.15 cells incubated with test compounds alone or in combination was determined by using CellTitre-Glo reagent according to the manufacturer protocol (Promega). The mean background signal from wells containing only culture medium was subtracted from all other samples, and percent inhibition at each compound concentration was calculated by normalizing to signals from HepG2.2.15 cells treated with 0.5% DMSO using equation E1.

% inhibition=(DMSOave−Xi)/DMSOave×100%   E1:

where DMSOave is the mean signal calculated from the wells that were treated with DMSO control (0% inhibition control) and Xi is the signal measured from the individual wells. EC50 values, effective concentrations that achieved 50% inhibitory effect, were determined by non-linear fitting using Graphpad Prism software (San Diego, Calif.) and equation E2

$$Y=Y\mathrm{min}+(Y\mathrm{max}-Y\mathrm{min})/(1+10(\mathrm{Log}\ \mathrm{EC}50-X)\times \mathrm{Hill\text{-}Slope})$$   E2:

where Y represents percent inhibition values and X represents the logarithm of compound concentrations.

Selected compounds of the invention were assayed in the HBV replication assay (BDNA assay), as described above and a representative group of these active compounds is shown in Table 3. Table 3 shows EC$_{50}$ values obtained by the BDNA assay for a group of select compounds. In Table 3, "A" represents 0.01<EC$_{50}$<0.10; "B" represents 0.10<EC$_{50}$<0.50; and "C" represents 0.50<EC$_{50}$<1.0.

TABLE 3

| Activity in BDNA-assay (EC$_{50}$) | |
|---|---|
| Compound | EC$_{50}$ (μM) |
| 434 | A |
| 561 | A |
| 587 | C |
| 599 | A |
| 795 | B |
| 796 | B |
| 798 | B |
| 800 | B |
| 803 | B |
| 805 | A |
| 594 | A |
| 595 | B |
| 600 | A |
| 695 | B |
| 697 | C |
| 698 | A |
| 699 | B |
| 828 E1 | A |
| 828 E2 | B |
| 910 | B |

TABLE 3-continued

Activity in BDNA-assay (EC$_{50}$)

| Compound | EC$_{50}$ (µM) |
| --- | --- |
| 912 | B |
| 937 | A |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula III:

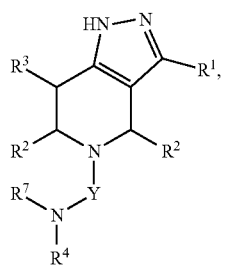

or a pharmaceutically acceptable salt thereof, wherein
Y is —C(O)—;
$R^1$ is —C(O)NR$^d$R$^e$, —C(O)NR$^d$OR$^e$, or —C(O)NR$^d$-NR$^d$;
$R^2$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
$R^3$ is selected from H, —OH, halo, C$_1$-C$_6$-alkyl, C$_1$-C$_6$-haloalkyl, —O—C$_1$-C$_6$-alkyl, and C$_1$-C6-alkyl-OH;
$R^4$ is selected from (CR$^8$R$^9$)$_p$-C$_1$-C$_9$-heteroaryl and (CR$^8$R$^9$)$_p$-C$_6$-C$_{12}$-aryl, wherein heteroaryl and aryl are optionally substituted with 1, 2, or 3 groups, each independently selected from —OH, halo, CN, C$_1$-C$_6$-alkyl, C$_1$-C$_6$-haloalkyl, —O—C$_1$-C$_6$-alkyl, and C$_1$-C$_6$-alkyl-OH;
$R^7$ is selected from H, C$_1$-C$_6$-alkyl, and C$_1$-C$_6$-alkyl-OH;
$R^8$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
$R^9$ is, at each occurrence, independently selected from H and C$_1$-C$_6$-alkyl;
$R^d$ is selected from H, C$_1$-C$_6$-alkyl, and C$_1$-C$_6$-alkyl-OH;
$R^e$ is selected from H, C$_1$-C$_6$-alkyl, C$_1$-C$_6$-alkyl-OH, C$_1$-C$_6$-alkyl-OC$_1$-C$_6$-alkyl, C$_0$-C$_6$-alkyl-C$_3$-C$_8$-cycloalkyl, C$_2$-C$_8$-heterocyclyl, C$_6$-C$_{12}$-aryl, and C$_1$-C$_9$-heteroaryl, wherein cycloalkyl, heterocyclyl, aryl, and heteroaryl are optionally substituted with 1, 2, or 3 groups, each independently selected from —OH, halo, CN, C$_1$-C$_6$-alkyl, C$_1$-C$_6$-haloalkyl, and —O—C$_1$-C$_6$-alkyl;
alternatively, R$^d$ and R$^e$ are optionally joined to form a heterocyclic ring, which is optionally substituted with 1, 2, or 3 groups, each independently selected from —OH, halo, CN, C$_1$-C$_6$-alkyl, C$_1$-C$_6$-haloalkyl, and —O—C$_1$-C$_6$-alkyl; and
p is 0, 1, 2, 3, or 4.

2. The compound of claim 1, wherein $R^1$ is —C(O)NR$^d$R$^e$, wherein
$R^d$ is selected from the group consisting of H, C$_1$-C$_6$-alkyl, and C$_1$-C$_6$-alkyl-OH,
$R^e$ is selected from the group consisting of H, C$_1$-C$_6$-alkyl, C$_1$-C$_6$-alkyl-OH, C$_3$-C$_8$-cycloalkyl, C$_2$-C$_8$-heterocyclyl, C$_6$-C$_{12}$-aryl, C$_1$-C$_9$-heteroaryl, and —O—C$_1$-C$_6$-alkyl,
or R$^d$ and R$^e$ optionally form a heterocyclic ring; or
$R^1$ is —C(O)NR$^d$OR$^e$, wherein R$^e$ is selected from the group consisting of C$_1$-C$_6$-alkyl-OC$_1$-C$_6$-alkyl, C$_0$-C$_6$-alkyl-C$_3$-C$_8$-cycloalkyl, C$_2$-C$_8$-heterocyclyl, C$_6$-C$_{12}$-aryl, and C$_1$-C$_9$-heteroaryl, wherein cycloalkyl, heterocyclyl, aryl, and heteroaryl are optionally substituted with 1, 2, or 3 groups, each independently selected from the group consisting of —OH, halo, CN, C$_1$-C6-alkyl, C$_1$-C$_6$-haloalkyl, and —O—C$_1$-C$_6$-alkyl.

3. The compound of claim 1, wherein each R$^2$ is independently H or C$_1$-C$_4$-alkyl; and R$^3$ is H.

4. The compound of claim 1, wherein R$^4$ is (CR$^8$R$^9$)$_p$-C$_1$-C$_5$-heteroaryl or (CR$^8$R$^9$)$_p$-C$_6$-aryl, wherein heteroaryl and aryl are optionally substituted with 1, 2, or 3 groups, each independently selected from —OH, halo, CN, and C$_1$-C$_6$-alkyl;
$R^8$ is H or C$_1$-C$_6$-alkyl;
$R^9$ is H or C$_1$-C$_6$-alkyl; and
p is 0 or 1.

5. The compound of claim 1, wherein R$^4$ is C$_1$-C$_5$-heteroaryl or C$_6$-aryl, wherein heteroaryl and aryl are optionally substituted with 1, 2, or 3 groups, each independently selected from —OH, halo, CN, and C$_1$-C$_6$-alkyl.

6. The compound of claim 1, wherein R$^4$ is:

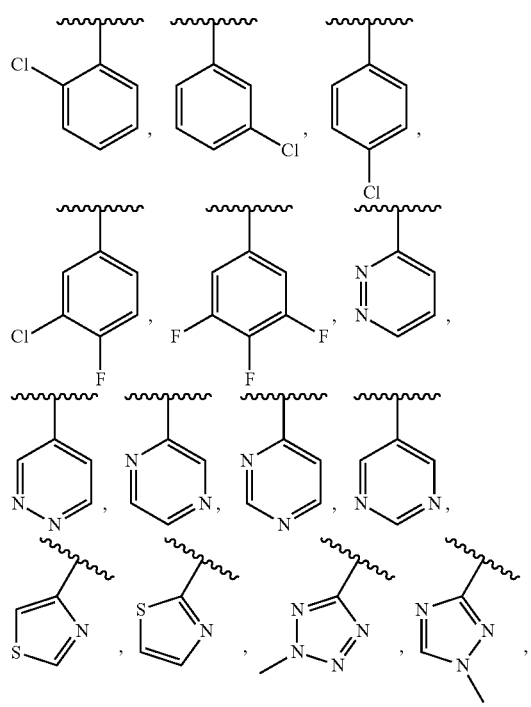

-continued
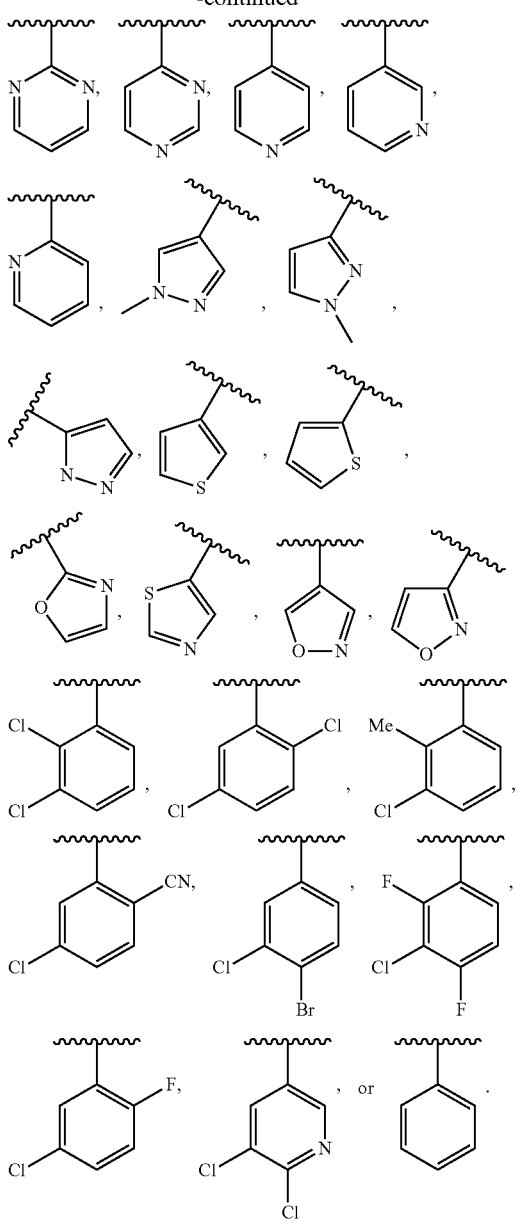
7. The compound of claim 1, wherein R⁷ is H.
8. The compound of claim 1 selected from:
256
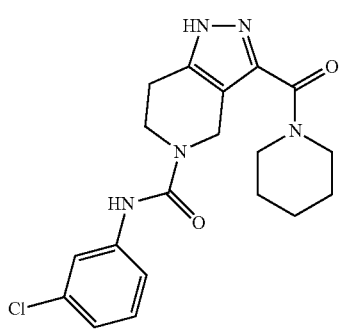
-continued
257
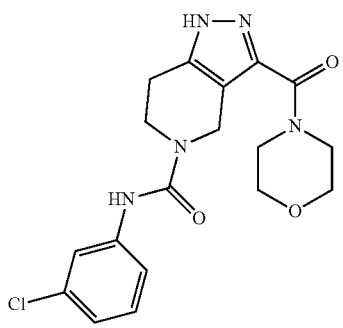
434
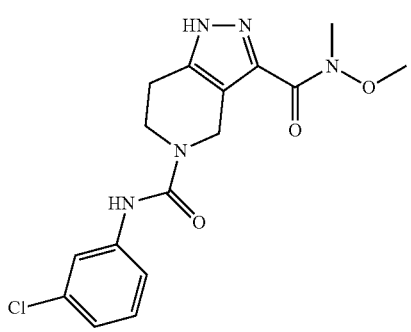
587
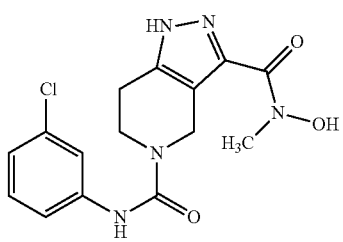
599
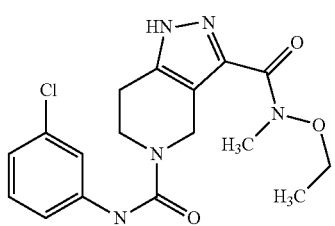
795
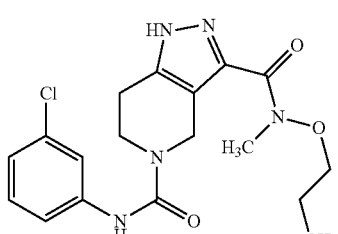
796
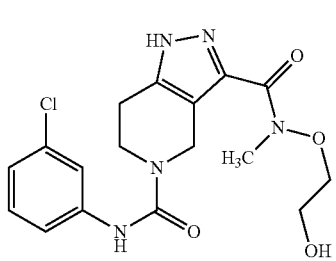 [SMILES: CN(OCCO)C(=O)c1n[nH]c2c1CN(C(=O)Nc1cccc(Cl)c1)CC2]

798
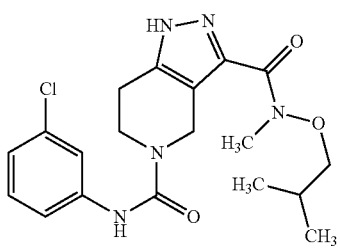 [SMILES: CC(C)CON(C)C(=O)c1n[nH]c2c1CN(C(=O)Nc1cccc(Cl)c1)CC2]
800
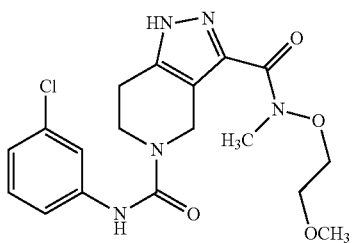 [SMILES: COCCON(C)C(=O)c1n[nH]c2c1CN(C(=O)Nc1cccc(Cl)c1)CC2]
803
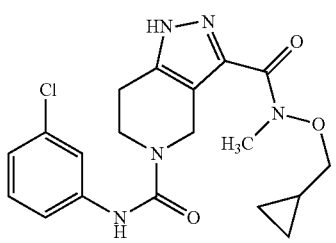 [SMILES: CN(OCC1CC1)C(=O)c1n[nH]c2c1CN(C(=O)Nc1cccc(Cl)c1)CC2]
805
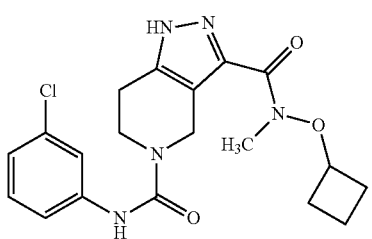 [SMILES: CN(OC1CCC1)C(=O)c1n[nH]c2c1CN(C(=O)Nc1cccc(Cl)c1)CC2]
594
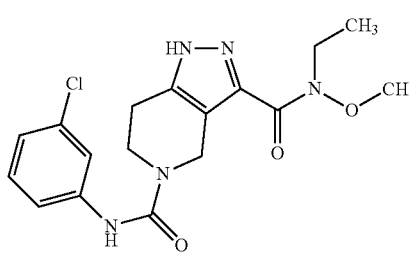
595
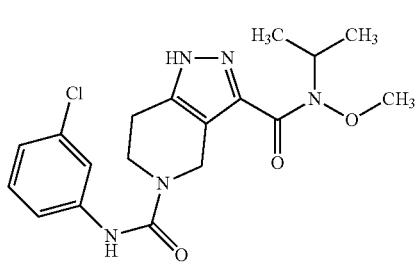
600
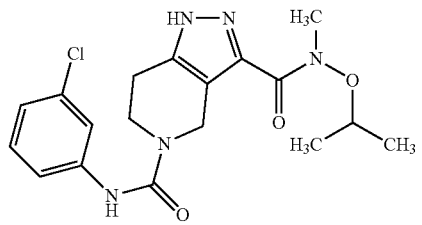
697
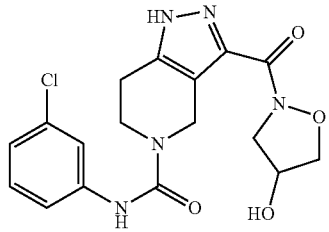 [SMILES: O=C(Nc1cccc(Cl)c1)N1CCc2[nH]nc(C(=O)N3CC(F)CO3)c2C1]
698
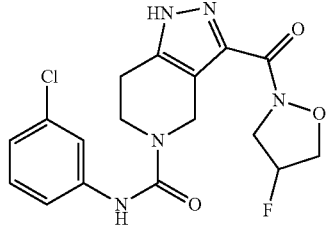 [SMILES: O=C(Nc1cccc(Cl)c1)N1CCc2[nH]nc(C(=O)N3CCCO3)c2C1]
699
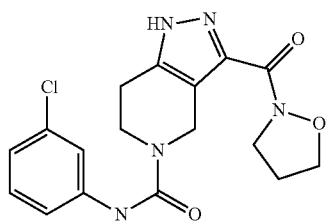
828
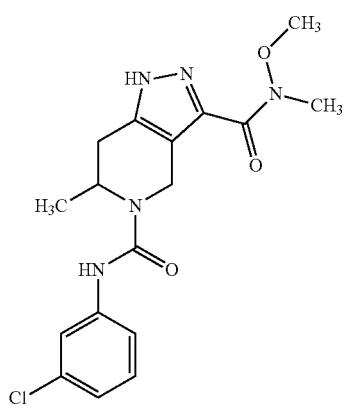 [SMILES: CON(C)C(=O)c1n[nH]c2c1CN(C(=O)Nc1cccc(Cl)c1)C(C)C2]
910
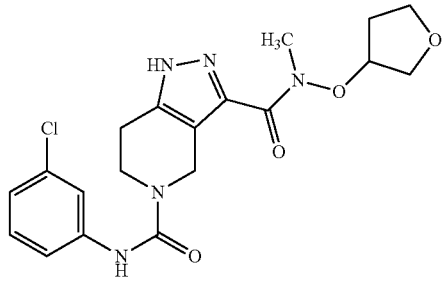 [SMILES: CN(OC1CCOC1)C(=O)c1n[nH]c2c1CN(C(=O)Nc1cccc(Cl)c1)CC2]

-continued

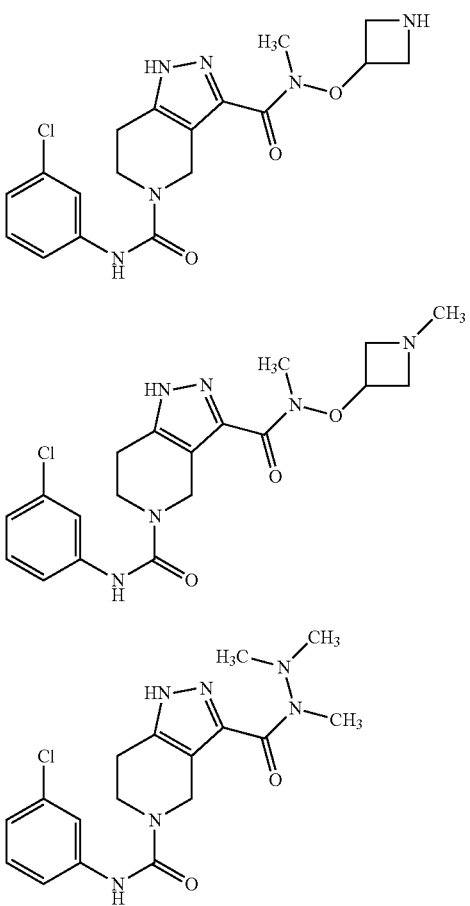

and pharmaceutically acceptable salts thereof.

9. A pharmaceutical composition comprising a compound of claim 1, or a pharmaceutically acceptable salt thereof, together with a pharmaceutically acceptable carrier.

10. A method of treating an HBV infection in an individual in need thereof, comprising administering to the individual a therapeutically effective amount of a compound according to claim 1.

11. A method of inhibiting and/or reducing the formation or presence of HBV DNA-containing particles and/or HBV RNA-containing particles in an individual in need thereof, comprising administering to the individual a therapeutically effective amount of a compound according to claim 1.

12. The method of claim 10, further comprising administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, a cyclophilin/TNF inhibitor, a TLR-agonist, an HBV vaccine, and a combination thereof.

13. The method of claim 12, wherein the therapeutic agent is a reverse transcriptase inhibitor, and is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, and Etravirine.

14. The method of claim 12, wherein the therapeutic agent is a TLR agonist, and wherein the TLR agonist is a TLR-7 agonist selected from the group consisting of SM360320 (9-benzyl-8-hydroxy-2-(2-methoxy-ethoxy) adenine)and AZD 8848 (methyl [3-({[3-(6-amino-2-butoxy-8-oxo-7,8-dihydro-9H-purin-9-yl)propyl][3-(4-morpholinyl)propyl]amino}methyl)phenyl]acetate).

15. The method of claim 12, wherein the therapeutic agent is an interferon selected from the group consisting of interferon alpha (IFN-α), interferon beta (IFN-β), interferon lambda (IFN-λ), and interferon gamma (IFN-γ).

16. The method of claim 15, wherein the interferon is interferon-alpha-2a, interferon-alpha-2b, or interferon-alpha-n1.

17. The method of claim 16, wherein the interferon-alpha-2a or interferon-alpha-2b is pegylated.

18. The method of claim 10, further comprising administering to the individual at least one HBV vaccine, a nucleoside HBV inhibitor, an interferon or any combination thereof.

19. The method of claim 18, wherein the HBV vaccine is selected from the group consisting of RECOMBIVAX HB, ENGERIX-B, ELOVAC B, GENEVAC-B, and SHANVAC B.

* * * * *